United States Patent [19]

Londesborough et al.

[11] Patent Number: 5,422,254
[45] Date of Patent: Jun. 6, 1995

[54] METHOD TO INCREASE THE TREHALOSE CONTENT OF ORGANISMS BY TRANSFORMING THEM WITH THE STRUCTURAL GENES FOR THE SHORT AND LONG CHAINS OF YEAST TREHALOSE SYNTHASE

[75] Inventors: John Londesborough; Outi Vuorio, both of Helsinki, Finland

[73] Assignee: Oy Alko Ab, Helsinki, Finland

[21] Appl. No.: 841,997

[22] Filed: Feb. 28, 1992

Related U.S. Application Data

[63] Continuation of Ser. No. 836,021, Feb. 14, 1992, abandoned.

[51] Int. Cl.$^6$ ............................................. C12P 19/18
[52] U.S. Cl. ................................. 435/97; 435/172.3; 435/193; 435/254.2; 435/254.21; 435/320.1; 435/942; 536/23.2; 536/23.74; 935/28; 935/29; 935/37
[58] Field of Search .................... 435/97, 172.3, 193, 435/320.1, 254.2, 254.21; 536/23.2, 23.74; 935/28, 29, 37

[56] References Cited

U.S. PATENT DOCUMENTS

| | | | |
|---|---|---|---|
| 4,615,974 | 10/1986 | Kingsman et al. | 935/28 |
| 4,794,175 | 12/1988 | Nunberg et al. | 935/14 |
| 4,876,197 | 10/1989 | Burke et al. | 435/69.9 |
| 5,312,909 | 5/1994 | Driessen et al. | 536/23.2 |

FOREIGN PATENT DOCUMENTS

| | | |
|---|---|---|
| 0415567A2 | 3/1991 | European Pat. Off. . |
| 0451896A1 | 10/1991 | European Pat. Off. . |
| WO87/00196 | 1/1987 | WIPO . |
| WO89/00012 | 1/1989 | WIPO . |
| WO89/06542 | 7/1989 | WIPO . |
| WO89/06976 | 8/1989 | WIPO . |

OTHER PUBLICATIONS

John Londesborough et al, "Trehalose-6-phosphate synthase/phosphatase complex from baker's yeast: purification of a proteolytically activated form", J. of Gen. Microbiology, vol. 137, pp. 323-330 (1991).

O. E. Vuorio et al, "Purification of Trehalose-6-phosphate Synthetase Phosphatase Complex from Baker's Yeast", Abstract, 20th FEBS Meeting, Aug. 1990, Budapest, Hungary. Abstract No. P-Tu 560.

Vania M. F. Paschoalin et al, "Identification of an ADPG-dependent trehalose synthase in Saccharomyces", Curr. Genet, vol. 16, pp. 81-87 (1989).

Anita D. Panek et al, "Metabolism and thermotolerance function of trehalose in Saccharomyces: a current perspective", J. of Biotech., vol. 14, pp. 229-238 (1990).

A. C. Panek et al, "Regulation of the trehalose-6-phosphate synthase in Saccharomyces", Curr. Genet, vol. 11, pp. 459-465 (1987).

Annick Vandercammen et al, "Characterization of trehalose-6-phosphate synthase and trehalose-6-phosphate phosphatase of Saccharomyces cerevisiae", Eur. J. Biochem., vol. 182, pp. 613-620 (1989).

Paul V. Attfield, "Trehalose accumulates in Saccharomyces cerevisiae during exposure to agents that induce heat shock response", Elsevier Science, Publishers (Biomed. Div.), vol. 225, Nos. 1,2, pp. 259-263 (1987).

Marcelino Banuelos et al, "Saccharomyces carsbergensis fdp Mutant and Futile Cycling of Fructose 6-Phosphate Molecular and Cellular Biology", vol. 2, No. 8, pp. 921-929 (1982).

E. Cabib et al, "The Biosynthesis of Trehalose Phosphate", J. Biol Chem., vol. 231, pp. 259-275 (1957).

(List continued on next page.)

*Primary Examiner*—Stephen G. Walsh
*Attorney, Agent, or Firm*—Adduci, Mastriani, Schaumberg & Schill

[57] ABSTRACT

Two nucleotide sequences encoding two different polypeptides found in yeast trehalose synthase have been isolated and cloned. The coding sequences can be inserted into suitable vectors and used to transform host cells. The transformed cells will produce increased amounts of trehalose compared to the untransformed wild types and have increased tolerance to a variety of stresses, in particular to decreased availability of water. The invention may be used to improve the stress tolerance of organisms, to increase the storage life of foodstuffs and to produce trehalose economically on an industrial scale in an organism (e.g, baker's yeast) that is a traditional and safe foodstuff.

24 Claims, 27 Drawing Sheets

OTHER PUBLICATIONS

John H. Crowe et al "Stabilization od dry phospholipid bilayers and proteins by sugars", Biochem. J., vol. 242, pp. 1–10 (1987).

Tony D'Amore et al, "The involvement of trehalose in yeast stress tolerance", J. of Indust. Microbiol., vol. 7, 191–196 (1991).

G. M. Gadd et al, "The role of trehalose in dehydration resistance of Saccharomyces cerevisiae", FEMS Microbiology Letters vol. 48, pp. 249–254 (1987).

Pierre Gelinas et al "Effect of Growth Conditions and Trehalose Content on Cryotolerance of Bakers' Yeast in Frozen Doughs", Applied and Environmental Microbiol., vol. 55, No. 10, pp. 2453–2459 (1989).

Akihiro Hino et al, "Trehalose Levels and Survival Ratio of Freeze-Tolerant versus Freeze-Sensitive Yeasts", Applied and Environmental Microbiol., vol. 55, No. 5, pp. 1386–1391 (1990).

Thomas Hottiger et al, "Rapid changes of heat and desiccation tolerance correlated with changes of trehalose content in Saccharomyces cerevisiae cells subjected to temperature shifts", FEBS Letters, vol. 220, No. 1, pp. 113–115 (1987).

Thomas Hottiger et al, "Correlatin of trenalose content and heat resistance in yeast mutants altered in the RAS-/adenylate cyclase pathway: is trehalose a thermoprotectant?", FEBS Letters, vol. 255, No. 2, pp. 431–434 (1989).

Rosario Lagunas et al, "Role of phosphate in the regulation of the Pasteur effect in Saccharomyces cerevisiae", Eur. J. Biochem, vol. 137, pp. 479–483 (1983).

U. K. Laemmli, "Cleavage of Structural Proteins during the Assembly of the Head of Bacteriophage T4", Nature, vol. 227, Aug. 15, 1970, pp. 680–685.

Gil Navon et al, "Phosphorus-31 Nuclear Magnetic Resonance Studies of Wild-Type and Glycolytic Pathway Mutants of Saccharomyces cerevisiae", Biochemistry, vol. 18, No. 21, pp. 4487–4499 (1979).

Maria José Neves et al, "Effects of heat shock on the level of trehalose and glycogen, and on the induction of thermotolerance in Neurospora crassa", FEBS Letters, vol. 283, No. 1, pp. 19–22 (1991).

Yuji Oda et al, "Selection of Yeasts for Breadmaking by the Frozen-Dough Method", Applied and Environmental Microbiology, vol. 56, No. 4, pp. 941–943 (1986).

G. R. Stewart, "Desiccation injury, anhydrobiosis and survival," in *Plants Under Stress,* Soc. Exper. Biol. Seminar, Series 39, Cambridge, UK (1989), pp. 115–130.

Patricia Tekamp-Olson et al, "The isolation, characterization and nucleotide sequence of the phosphoglucoisomerase gene of Saccharomyces cerevisiae", Gene, vol. 10, pp. 153–161 (1988).

K. W. van de Poll et al, "Characterization of a Regulatory Mutant of Frutose 1,6-Bisphosphatase in Saccharomyces carlsbergensis", MGG, pp. 61–66 (1977).

Andres Wiemken, "Trehalose in Yeast, Stress Protectant Rather Than Reserve Carbohydrate", Antonie van Leeuwenhoek, vol. 58, pp. 209–217 (1990).

Londesborough et al, Abstract, Gordon conference (on plant cold resistance) (1991).

Sankar Adhya et al, "Positive Control", J. Biolog. Chem., vol. 265, No. 19, pp. 10797–10800 (1990).

Emily C. Dale et al, "Gene transfer with subsequent removal of the selection gene from the host genome", Pro. Natl. Acad. Sci. USA, vol. 88, pp. 10558–10562, (1991).

David Pellman et al, "TATA-dependent and TATA-independent transcription at the HIS4 gene of yeast", Nature, vol. 348, pp. 82–85 (1990).

Gilbert Berben et al, "The YDp Plasmids: a Uniform Set of Vectors Bearing Versatile Gene Disruption Cassettes for Saccharomyces cerevisiae, Yeast", vol. 7, pp. 475–477 (1991).

Rodney J. Rothstein, "One-Step Gene Disruption in Yeast", Methods in Enzymology, vol. 101, pp. 203–243 (1983).

Patrick Russo et al, "Distinct cis-acting signals enhance 3′ endpoint formation of CYC1 mRNA in the yeast Saccharomyces cerevisiae", The Embo J., vol. 10, No. 3, pp. 563–571 (1991).

Pirkko L. Suominen, "Characterization and Application of the Yeast Mell Gene", Dissertation (1988).

Lillie and Pringle, J. Bacteriology, vol. 143, pp. 1384–1394 (1980).

Bhown et al, "High-Sensitivity Sequence Determination . . . " *An. Biochem.* 103:184–190 (1980).

Giaever et al. "Biochemical and Genetic Characterization of Osmoregulatory Trehalose Synthesis . . . ", *J. Bacteriol.* 170:2841–2849, Jun. 1988.

Nelson et al, "A Conserved Gene Encoding the 57-kDa Subunit . . . " *J. Biol. Chem.* 264:1775–1778, Jan. 25, 1989.

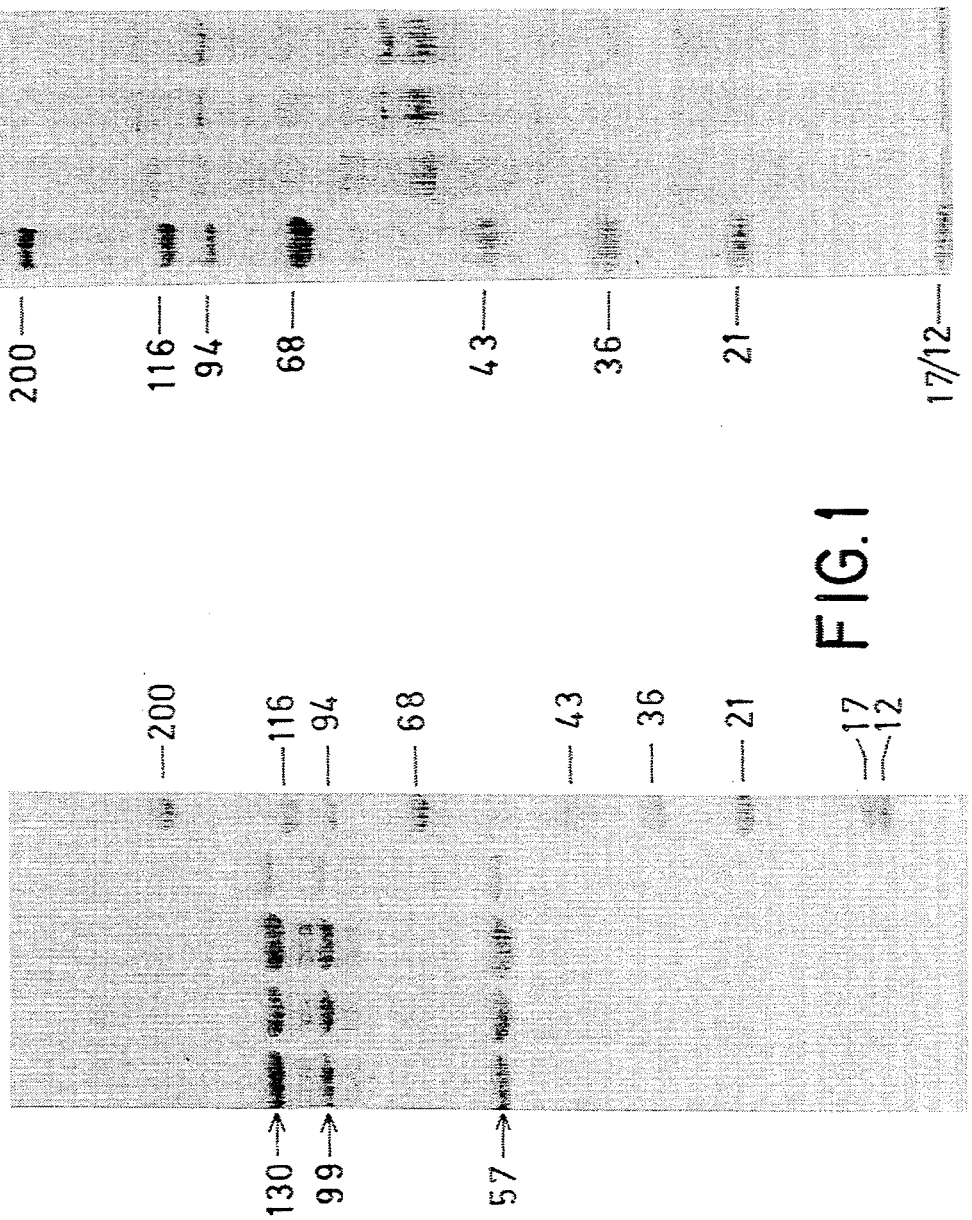

FIG.3A

```
         10         20         30         40         50         60
TTTTTAAACG TATATAGATG TCTACATGTG TGTTTTTGTT TTTTTACGTA CGTATACCCC
         70         80         90        100        110        120
ACTATATATG CATAATCCGT AATTGAAAAA AAAAAAAGTA AAGATCAAGG AACACATCAC
        130        140        150        160        170        180
CCTGGGCACA TCAAGCGTGA GGAATGCCGT CCAACTGGTG GAGACGCTTG ATTTGCTCTT
        190        200        210        220        230        240
TTTGTTCCTG GGTCCAACCC GGTCTCGAAG AACATCAGCA CCACGCCCGC AACGACAAAG
        250        260        270        280        290        300
AACATTGCAA TACACTTGCA TATGTGAGCA TAGTCGAGCG GTCCGTTCTG TGGTTGATGC
        310        320        330        340        350        360
TGTTGTTCTT TCTTCTGTTT GTCAGGGGTG ATAGCCATAT CTTCGTGCTC TTGTTGCGAT
        370        380        390        400        410        420
TGTTCTGTTC CATCTGCACC AGAACAAAGA ACAAAAGAAC AAGGAACAAA GTCCAAGCAC
        430        440        450        460        470        480
GTCAGGCGCTG TTTATAAGGG GATTGACGAG GGATCGGGCC TAGAGTGCCA GCGGCGCCAGG
        490        500        510        520        530        540
GAGAGGGAGC CCCCTGGGCC CTCATCCGCA GGCTGATAGG GGTCACCCCG CTGGGCAGGT
        550        560        570        580        590        600
CAGGGCAGGG GCTCTCAGGG GGGCGCCATG GACAAACTGC ACTGAGGTTC TAAGACACAT
```

FIG.3B

```
 610        620        630        640        650        660
GTATTATTGT GAGTATGTAT ATATAGAGAG AGATTAAGGC GTACACGCGT GGTTGGTAGA
 670        680        690        700        710        720
GATTGATTAA CTTGGTAGTC TTATCTTGTC AATTGAGTTT CTGTCAGTTT CCTTCTTGAA
 730        740        750        760        770        780
CAAGCACGCA GCTAAGTAAG CAACAAAGCA GGCTAACAAA CTAGGTACTC ACATACAGAC
 790        800        810        820        830        840
TTATTAAGAC ATAGAACTAT GACTACGGAT AACGCTAAGG CGCAACTGAC CTCGTCTTCA
 850        860        870        880        890        900
GGGGTAACA  TTATTGTGGT GTCCAACAGG CTTCCCGTGA CAATCACTAA AAACAGCAGT
 910        920        930        940        950        960
ACGGGACAGT ACGAGTACGC AATGTCGTCC GGAGGGCTGG TCACGGGCGTT GGAAGGGTTG
 970        980        990       1000       1010       1020
AAGAAGACAGT ACACTTTCAA GTGGTTCGGA TGGCCTGGGC TAGAGATTCC TGACGATGAG
1030       1040       1050       1060       1070       1080
AAGGATCAGG TGAGGAAGGA CTTGCTGGAA AAGTTTAATG CCGTACCCAT CTTCCTGAGC
1090       1100       1110       1120       1130       1140
GATGAAATCG CAGACTTACA CTACAACGGG TTCAGTAATT CTATTCTATG GCCGTTATTC
1150       1160       1170       1180       1190       1200
CATTACCATC CTGGTGAGAT CAATTTCGAC GAGAATGCGT GGTTCGGATA CAACGAGGCA
1210       1220       1230       1240       1250       1260
AACCAGACGT TCACCAACGA GATTGCTAAG ACTATGAACC ATAACGATTT AATCTGGGTG
```

FIG.3C

| | | | | |
|---|---|---|---|---|
| 1270 CATGATTACC | 1280 ATTTGATGTT | 1290 GGTTCCGGAA | 1300 ATGTTGAGAG | 1310 TCAAGATTCA | 1320 CGAGAAGCAA |
| 1330 CTGCAAAACG | 1340 TTAAGGTCGG | 1350 GTGGTTCCTG | 1360 CACACACCAT | 1370 TCCCTTCGAG | 1380 TGAAATTTAC |
| 1390 AGAATCTTAC | 1400 CTGTCAGACA | 1410 AGAGATTTTG | 1420 AAGGGTGTTT | 1430 TGAGTTGTGA | 1440 TTTAGTCGGG |
| 1450 TTCCACACAT | 1460 ACGATTATGC | 1470 AAGACATTTC | 1480 TTGTCTTCCG | 1490 TGCAAAGAGT | 1500 GCTTAACGTG |
| 1510 AACACATTGC | 1520 CTAATGGGGT | 1530 GGAATACCAG | 1540 GGCAGATTCG | 1550 TTAACGTAGG | 1560 GGCCTTCCCT |
| 1570 ATCGGTATCG | 1580 ACGTGGACAA | 1590 GTTCACCGAT | 1600 GGGTTGAAAA | 1610 AGGAATCCGT | 1620 ACAAAAGAGA |
| 1630 ATCCAACAAT | 1640 TGAAGGAAAC | 1650 TTTCAAGGGC | 1660 TGCAAGATCA | 1670 TAGTTGGTGT | 1680 CGACAGGCTG |
| 1690 GATTACATCA | 1700 AAGGTGTGCC | 1710 TCAGAAGTTG | 1720 CACGCCATGG | 1730 AAGTGTTTCT | 1740 GAACGAGCAT |
| 1750 CCAGAATGGA | 1760 GGGGCAAGGT | 1770 TGTTCTGGTA | 1780 CAGGTTGCAG | 1790 TGCCAAGTCG | 1800 TGGAGATGTG |
| 1810 GAAGAGTACC | 1820 AATATTTAAG | 1830 ATCTGTGGTC | 1840 AATGAGTTGG | 1850 TCGGTAGAAT | 1860 CAACGGTCAG |

```
1870       1880       1890       1900       1910       1920
TTCGGTACTG TGGAATTCGT CCCCATCCAT TTCATGCACA AGTCTATACC ATTTGAAGAG
1930       1940       1950       1960       1970       1980
CTGATTTCGT TATATGCTGT GAGCGATGTT TGTTTGGTCT CGTCCACCCG TGATGGTATG
1990       2000       2010       2020       2030       2040
AACTTGGTTT CCTACGAATA TATTGCTTGC CAAGAAGAAA AGAAAGGTTC CTTAATCCTG
2050       2060       2070       2080       2090       2100
AGTGAGTTCA CAGGTGCCGC ACAATCCTTG AATGGTGCTA TTATTGTAAA TCCTTGGAAC
2110       2120       2130       2140       2150       2160
ACCGATGATC TTTCTGATGC CATCAACGAG GCCTTGACTT TGCCCGATGT AAAGAAAGAA
2170       2180       2190       2200       2210       2220
GTTAACTGGG AAAAACTTTA CAAATACATC TCTAAATACA CTTCTGCCTT CTGGGGTGAA
2230       2240       2250       2260       2270       2280
AATTTCGTCC ATGAATTATA CAGTACATCA TCAAGCTCAA CAAGCTCCTC TGCCACCAAA
2290       2300       2310       2320       2330       2340
AACTGATGAA CCCGATGCAA ATGAGACGAT CGTCTATTCC TGGTCCGGTT TTCTCTGCCC
2350       2360       2370       2380       2390       2400
TCTCTTCTAT TCACTTTTTT TATACTTTAT ATAAAATTAT ATAAATGACA TAACTGAAAC
2410       2420       2430       2440       2450       2460
GCCACACGTC CTCTCCTATT CGTTAACGCC TGTCTGTAGC GCTGTTACTG AAGCTGCGCA
2470       2480
AGTAGTTTTT TCACCGTATA GGCC
```

```
        10                    20                    30
RGLQGSKFGAIHKSTKKYALLRSSQELFSR
        40                    50                    60
LPWSIVPSIKGNGAMKNAINTAVLENIIPH
        70                    80                    90
RHVKWVGTVGIPTDEIPENILANISDSLKD
       100                   110                   120
KYDSYPVLTDDDTFKAAYKNYCKQILWPTL
       130                   140                   150
HYQIPDNPNSKAFEDHSWKFYRNLNQRFAD
       160                   170                   180
AIVKIYKKGDTIWIHDYHLMLVPQMVRDVL
       190                   200                   210
PFAKIGFTLHVSFPSSEVFRCLAQREKILE
       220                   230                   240
GLTGADFVGFQTREYARHFLQTSNRLLMAD
       250                   260                   270
VVHDEELKYNGRVVSVRFTPVGIDAFDLQS
```

```
              280                        290                  300
      QLKDGSVMQWRQLIRERWQGKKLIVCRDQF
              310                        320                  330
      DRIRGIHKKLLAYEKFLVENPEYVEKSTLI
              340                        350                  360
      QICIGSSKDVELERQIMIVVDRINSLSTNI
              370                        380                  390
      SISQPVVFLHQDLDFSQYLALSSEADLFVV
              400                        410                  420
      SSLREGMNLTCHEFIVCSEDKNAPLLLSEF
              430                        440                  450
      TGSASLLNDGAIIINPWDTKNFSQAILKGL
              460                        470                  480
      EMPFDKRRPQWKKLMKDIINNDSTNWIKTS
              490                        500                  510
      LQDIHISWQFNQEGSKIFKLNTKTLMEDYQ
              520                        530                  540
      SSKKRMFVFNIAEPPSSRMISILNDMTSKG
```

```
       550                    560                570
NIVYIMNSFPKPILENLYSRVQNIGLIAEN
       580                    590                600
GAYVSLNGVWYNIVDQVDWRNDVAKILEDK
       610                    620                630
VERLPGSYYKINESMIKFHTENAEDQDRVA
       640                    650                660
SVIGDAITHINTVFDHRGIHAYVYKNVVSV
       670                    680                690
QQVGLSLSAAQFLFRFYNSASDPLDTSSGQ
       700                    710                720
ITNIQTPSQQNPGDQEQQPPASPTVSMNHI
       730                    740                750
DFACVSGSXSPVLEPLFKLVNDEASEGQVK
       760                    770                780
AGHAIVYGDATSTYAKEHVNGLNELFTIIS

RIIEDU
```

FIG.5A

| Pos | Sequence |
|---|---|
| 1 | MetThrThrAspAsnAlaLys   AlaGlnLeuThrSerSerGlyGlyAsnIle |
| 1 | ArgGlyLeuGluGlnGly SerLysPheGlyAlaAlaIleHisLysSerThrLysLysTyrAlaLeu |
| 19 | IleValValSer   AsnArgLeuProValThrIleThrLysAsnSerSer |
| 21 | LeuArgSerSerGlnGluLeuPheSerArgLeuProTrpSerIle  ValProSerIle |
| 35 | ThrGlyGlnTyrGlu TyrAlaMetSerSerGlyGlyLeuValThrAla  LeuGluGly |
| 40 | LysGly  AsnGlyAlaMet  LysAsnAlaIleAsnThrAlaValLeuGluAsn |
| 54 | LeuLysLysThrTyrThrPheLysTrp  PheGlyTrpProGlyLeuGluIle |
| 57 | IleIleProHisArgHisValLysTrpValGlyThrValGlyIleProThrAspGluIle |
| 71 | ProAspAspGluLysAspGlnValArgLysAspLeuLeuGluLysPheAsnAlaValPro |
| 77 | ProGluAsnIleLeuAlaAsnIleSerAspSerLeuLysAspLysTyrAspSerTyrPro |
| 91 | IlePheLeuSerAspGluIleAlaAspLeuHisTyrAsnGlyPheSerAsnSerIleLeu |
| 97 | ValLeuThrAspAspThrPheLysAlaAlaTyrLysAsnTyrCysLysGlnIleLeu |
| 111 | TrpProLeuPheHisTyr  HisProGlyGluIle Asn   PheAspGluAsn |
| 117 | TrpProThrLeuHisTyrGlnIleProAspAsnProAsnSerLysAlaPheGluAspHis |

FIG.5B

| | |
|---|---|
| 127 | AlaTrpPheGlyTyrAsnGluAlaAsnGlnThrPheThrAsnGluIleAlaLysThrMet |
| 137 | SerTrpLysPheTyrArgAsnLeuAsnGlnArgPheAlaAspAlaIleValLysIleTyr |
| 147 | AsnHisAsnAspLeuIleTrpValHisAspTyrHisLeuMetLeuValProGluMetLeu |
| 157 | LysLysGlyAspThrIleTrpIleHisAspTyrHisLeuMetLeuValProGlnMetVal |
| 167 | ArgValLysIleHisGluLysGlnLeuGlnAsnValLysValGlyTrpPheLeuHisThr |
| 177 | Arg AspValProPheAlaLysIleGlyPheThrLeuHisVal |
| 187 | ProPheProSerGluIleTyrArgIleLeuProValArgGlnGluIleLeuLeuLysGly |
| 192 | SerPheProSerGluValPheArgCysLeuAlaGlnArgGluLysIleLeuLeuGluGly |
| 207 | ValLeuSerCysAspLeuValGlyPheHisThrTyrAspTyrAlaArgHisPheLeuSer |
| 212 | LeuThrGlyAlaAspPheValGlyPheAlaGlyPheAlaArgHisPheLeuGln |
| 227 | SerValGlnArgValLeu AsnValAsnThrLeuProAsnGlyValGlyValGluTyrGlnGly |
| 232 | ThrSerAsnArgLeuLeuMetAlaAspValValHisAspGluGluLeuLysTyrAsnGly |
| 246 | ArgPheValAsnValGlyAlaAlaPheProIleGlyIleAspValAspLysPheThrAspGly |
| 252 | ArgValValSerValArgPheThrProValGlyIleAspAlaPheAspLeuGlnSerGln |
| 266 | LeuLysLysGluSerVal GlnLysArgIleGlnGlnLeuLysGluThrPheLysGly |
| 272 | LeuLysAspGlySerValMetGlnTrpArg GlnLeuIleArgGluArgTrpGlnGly |

FIG.5C

| | |
|---|---|
| 285 | CysLysIleIleValGlyGlyValAspArgLeuAspTyrIleLysGlyValProGlnLysLeu |
| 291 | LysLysLeuIleValCysArgAspGlnPheAspArgIleArgGlyIleHisLysLysLeu |
| 305 | HisAlaMetGluValPheLeuAsnGluHisProGluTrpArgGlyLysValValLeuVal |
| 311 | LeuAlaTyrGluLysPheLeuValGluAsnProGluTyrValGluLysSerThrLeuIle |
| 325 | GlnValAlaAlaValProSerArgGlyAspValGlu GluTyrGlnTyrLeuArgSerVal |
| 331 | GlnIleCysIleGlySerSerLysAspValGluLeuGluArgGln IleMetIleVal |
| 344 | ValAsnGluLeuValGlyArgIleAsn GlyGlnPheGlyThrValGluPheValPro |
| 350 | ValAspArgIleAsnSerLeuSerThrAsnIleSerIleSerGlnPro |
| 363 | IleHisPheMetHisLysSerIleProPheGluLeuIleSerLeuTyrAlaValSer |
| 366 | ValValPheLeuHisGlnAspLeuAspPheSerGlnTyrLeuAlaLeuSerSerGluAla |

FIG.5D

| | |
|---|---|
| 383 | AspValCysLeuValSerSerThrArgAspGlyMetAsnLeuValSerTyrGluTyrIle |
| 386 | AspLeuPheValValSerLeuArgGluGlyMetAsnLeuThrCysHisGluPheIle |
| 403 | AlaCysGlnGluGluLysLysGlySerLeuIleLeuSerGluPheThrGlyAlaAlaGln |
| 406 | ValCysSerGluAspLysAsnAlaProLeuLeuLeuSerGluPheThrGlySerAlaSer |
| 423 | SerLeuAsn   GlyAlaIleIleValAsnProTrpAsnThrAspAspLeuSerAspAla |
| 426 | LeuLeuAsnAspGlyAlaIleIleIleAsnProTrpAspThrLysAsnPheSerGlnAla |
| 442 | IleAsnGluAlaLeuThrLeuProAspValLysLysGluValAsnTrpGluLysLeuTyr |
| 446 | IleLeuLysGlyLeuGluMetProPheAspLysArgArgProGlnTrpLysLysLeuMet |
| 462 | LysTyrIleSerLysTyrThrSerAlaPheTrp   GlyGluAsnPheValHisGluLeu |
| 466 | LysAspIleIleAsnAsnAspSerThrAsnTrpIleLysThrSerLeuGlnAspIleHis |
| 481 | TyrSerThrSerSerSerThrSerSerSerAlaThrLys   AsnEnd |
| 486 | IleSerTrpGlnPheAsnGlnGluGlySerLysIlePheLysLeuAsnThr |

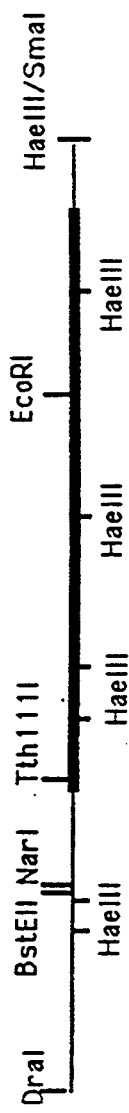
FIG. 6A
FIG. 6B

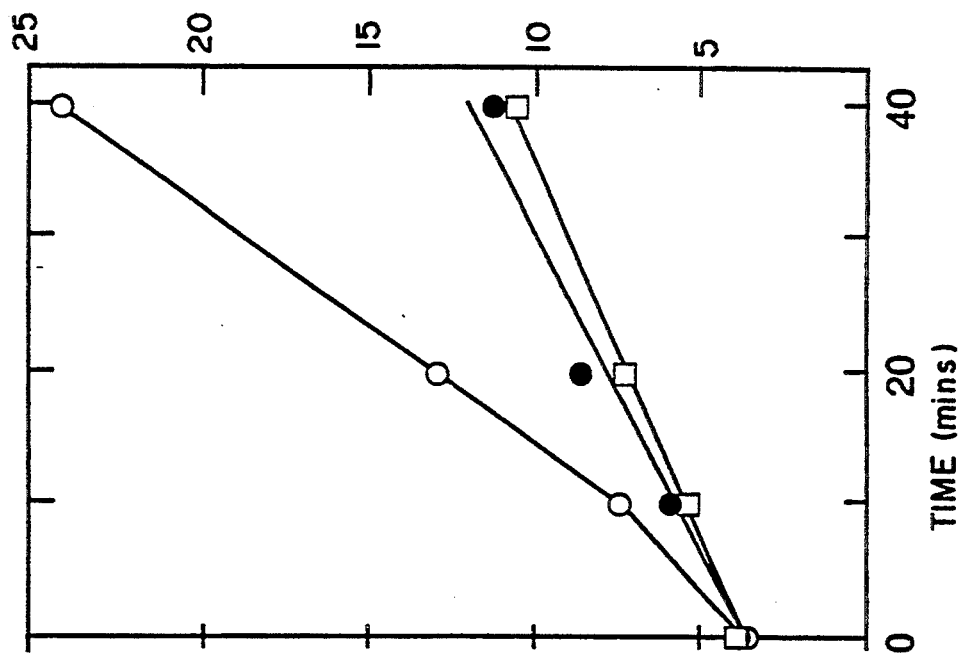
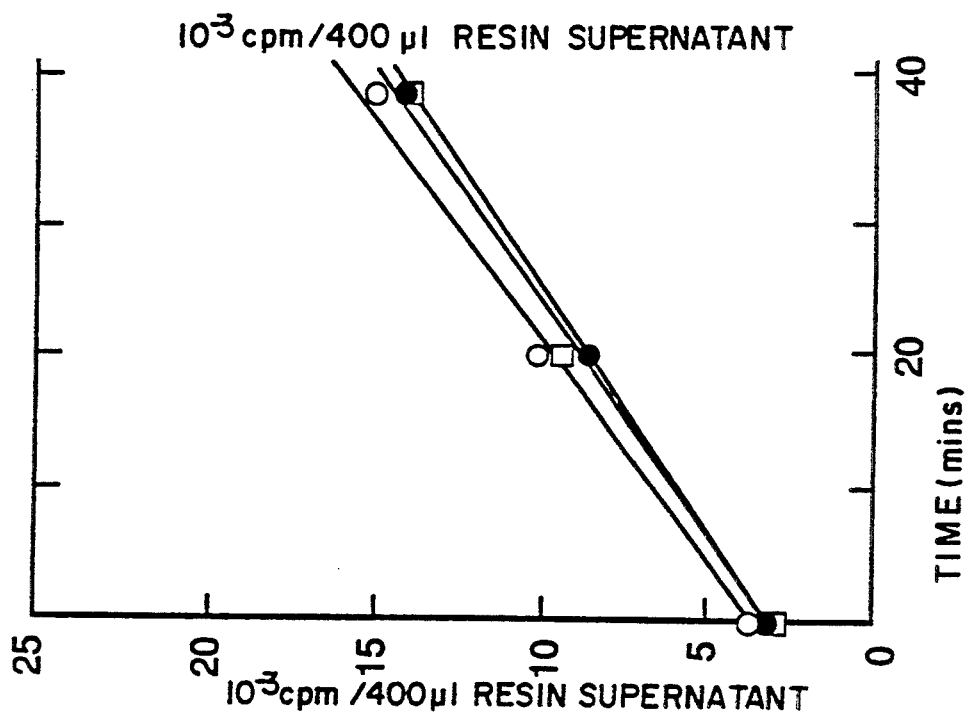
FIG. 7(a)
FIG. 7(b)

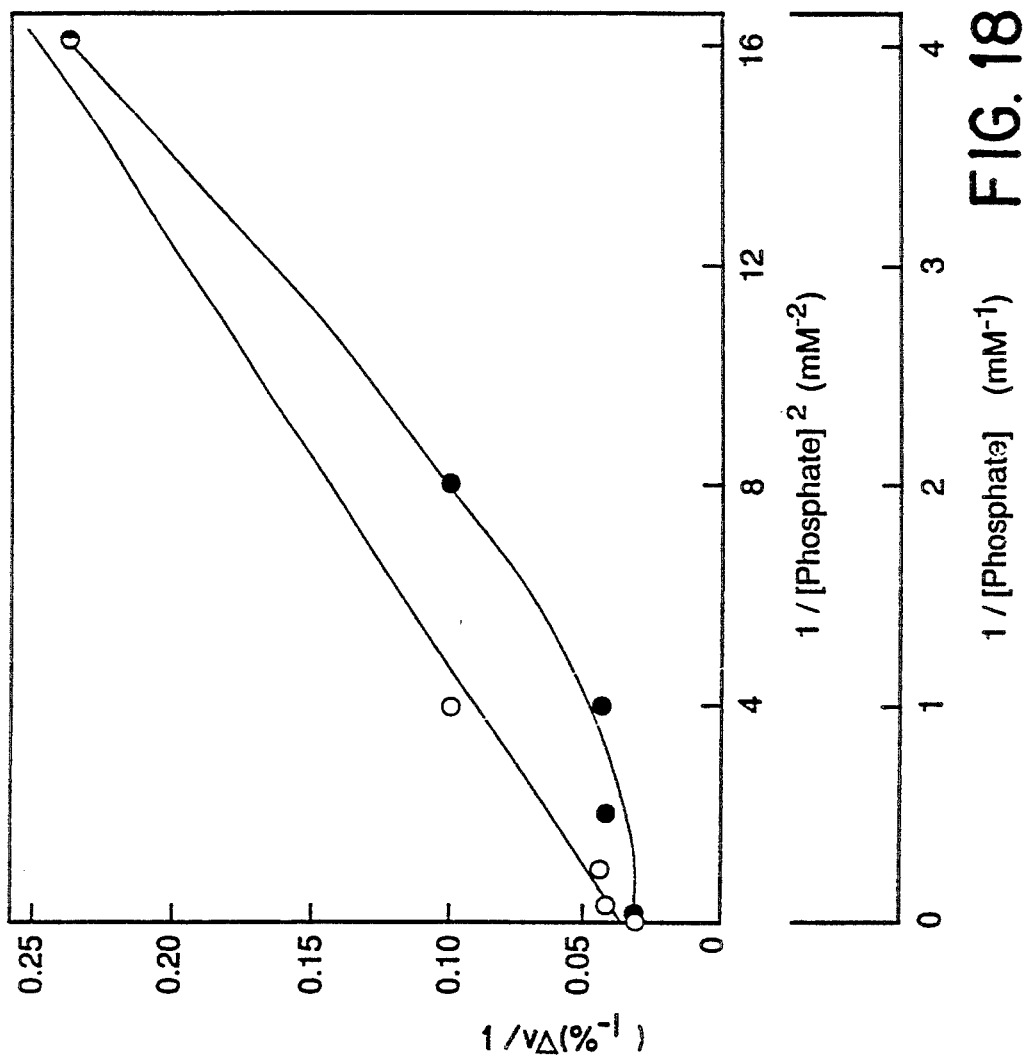

METHOD TO INCREASE THE TREHALOSE CONTENT OF ORGANISMS BY TRANSFORMING THEM WITH THE STRUCTURAL GENES FOR THE SHORT AND LONG CHAINS OF YEAST TREHALOSE SYNTHASE

This application is a continuation application of U.S. Ser. No. 836,021, filed Feb. 14, 1992, now abandoned.

Two nucleotide sequences encoding two different polypeptides found in yeast trehalose synthase have been isolated and cloned. The coding sequences can be inserted into suitable vectors and used to transform host cells. The transformed cells will produce increased amounts of trehalose compared to the untransformed wild types and have increased tolerance to a variety of stresses, in particular to decreased availability of water. The invention may be used to improve the stress tolerance of organisms, to increase the storage life of foodstuffs and to produce trehalose economically on an industrial scale in an organism (e.g, baker's yeast) that is a traditional and safe foodstuff.

BACKGROUND OF THE INVENTION

It is well known that sugars and other polyhydric compounds stabilize isolated proteins and phospholipid membranes during dehydration, probably by replacing the water molecules that are hydrogen-bonded to these macromolecules [reviewed by Crowe, J. H. et. al. (1987) Biochemical Journal 242, 1–10]. Trehalose ($\alpha$-D-glucopyranosyl-$\alpha$-D-glucopyranose) is a dimer of two glucose molecules linked through their reducing groups. Because it has no reducing groups, it does not take part in the Maillard reactions that cause many sugars to damage proteins, and it is one of the most effective known protectants of proteins and biological membranes in vitro.

In nature, trehalose is found at high concentrations in yeasts and other fungi, some bacteria, insects, and some litoral animals, such as the brine shrimp. It is notable that all these organisms are frequently exposed to osmotic and dehydration stress. Accumulation of trehalose in higher plants is rare, but high levels occur in the so-called resurrection plants, such as the pteridophyte, *Selaginella lepidophylla*, which can survive extended drought [Quillet, M. and Soulet, M. (1964) Comptes Rendus de l' Acadamie des Sciences, Paris 259, pp. 635–637; reviewed by Avigad, G. (1982) in Encyclopedia of Plant Research (New Series) 13A, pp. 217–347].

A decreased availability of intracellular water to proteins and membranes is a common feature not only of dehydration and osmotic stress, but also of freezing, in which ice formation withdraws water from inside the cells, and heat stress, which weakens the hydrogen bonds between water and biological macromolecules. In recent years a number of publications have shown a close connection between the trehalose content of yeast cells, especially of the species *Saccharomyces cerevisiae*, and their resistance to dehydration and osmotic, freezing and heat stresses. This work has lead to the concept [summarized by Wiemkem, A. (1990) Antonie van Leeuwenhoek 58, 209–217] that, whereas the main storage or reserve carbohydrate in yeast is glycogen, the prime physiological function of trehalose is as a protectant against these and other stresses, including starvation and even copper poisoning [Attfield, P. V. (1987) Federation of European Biochemical Societies Letters 225, 259–263].

Thus, during growth of *Saccharomyces cerevisiae* on glucose, glycogen begins to accumulate about one generation before the glucose is exhausted, and begins to be steadily consumed as soon as all external carbon supplies are exhausted. In contrast, accumulation of trehalose (partly at the expense of glycogen) only begins after all the glucose has been consumed, and the trehalose level is then maintained until all the glycogen has been consumed [Lillie, S. A. & Pringle, J. R. (1980) Journal of Bacteriology 143, 1384–1394]. The eventual consumption of trehalose is accompanied by a rapid decrease in the number of viable cells.

When trehalose levels in *S. cerevisiae* have been manipulated by varying the growth conditions or administering heat shocks, high positive correlations have been found between the trehalose content of the cells and their resistance to dehydration [Gadd, G. et al (1987) Federation of European Microbiological Societies Microbiological Letters 48, 249–254], heat stress [Hottiger, T. et al., (1987) Federation of European Biochemical Societies Letters 220, 113–115] and freezing [Gélinas, P. et al Applied and Environmental Microbiology 55, 2453–2459]. Also, strains of *S. cerevisiae* and other yeasts selected for resistance to osmotic stress [D'Amore, T. et. al. (1991) Journal of Industrial Microbiology 7, 191–196] or high performance in frozen dough fermentation [Oda, Y. (1986) Applied and Environmental Microbiology 52, 941–943] were found to have unusually high trehalose contents. Furthermore, a mutation in the cyclic AMP signaling system of *S. cerevisiae* that causes constitutive high trehalose levels also causes constitutive thermotolerance, whereas another mutation in this system that prevents the usual rise in trehalose during heat shock also prevents the acquisition of thermotolerance [Hottiger, T. et. al., (1989) Federation of European Biochemical Societies Letters 255, 431–434]. Thus, there is much evidence pointing to a connection between trehalose content and stress resistance in yeasts, especially *S. cerevisiae*. Similar findings have been made for several other fungi [e.g., Neves, M. J., Jorge, J. A., Francois, J. M. & Terenzi, H. F. (1991) Federation of European Biochemical Societies Letters 283, 19–22]. However, a causative relationship has not yet been demonstrated. Further, nearly all conditions that cause increases in the trehalose content of yeast also cause increases in the levels of the so-called heat shock proteins. The 1989 publication of Hottiger and colleagues, cited above, claims that canavanine does not cause an increase in either trehalose levels or thermotolerance, whereas this compound is reported to induce heat shock proteins.

Whether or not there is a causal relation between trehalose content and stress resistance, it is general practice in the manufacture of baker's yeast to maximise the trehalose content of the yeast. Various maturation processes have been developed to achieve this aim, and they are of crucial importance in the manufacture of active dried yeast. The details of these processes are often secret, but they are generally empirical regimes in which carbon and nitrogen feeds, aeration and temperature are carefully controlled and selected strains of yeast are used. They demand time and energy inputs during which little increase in cell number occurs. A more rational and controlled process that could be applied to any yeast strain would be of economic benefit.

According to Cabib, E. & Leloir, L. F. [(1957) Journal of Biological Chemistry 231, 259–275], trehalose is synthesized in yeast from uridine diphosphoglucose (UDPG) and glucose-6-phosphate (G6P) by the sequential action of two enzyme activities, trehalose-6-phosphate synthase and trehalose-6-phosphate phosphatase. Londesborough, J. & Vuorio, O. [(1991) Journal of Microbiology 137, 323–330, expressly incorporated herein by reference] have purified from baker's yeast a proteolytically modified protein complex that exhibited both these activities and appeared to contain a short polypeptide chain (57 kDa) and two truncated versions (86 kDa and 93 kDa) of a long polypeptide chain. The intact long chain was estimated to have a mass of at least 115 kDa. It was not disclosed which enzyme activity or activities was associated with which polypeptide, nor indeed whether both polypeptides were essential for either or both enzymatic activities. Anti-sera against both polypeptides were reported, but no amino acid sequences were disclosed.

An earlier patent application [EP 451 896; (see Claim 1)] has claims for a transformed yeast "comprising . . . one gene encoding . . . trehalose-6-phosphate synthase". No information about this gene was given. However, if it exists, it is clearly something different from the two structural genes encoding the long and short chains of trehalose synthase, because, as will be explained below, neither of these genes encodes a protein with properly functional TPS activity.

Several authors have reported increases in TPS activity in conditions that lead to accumulation of trehalose by *S. cerevisiae*, and *Schizosaccharomyces pombe* both during the approach to stationary phase [Winkler, K. Kienle, I. Burgert, M. Wagner, J.-C. & Holzer, H. (1991) Federation of European Biochemical Societies Letters 291, 269–272; Francois, J., Neves, M.-J. & Hers, H.-G. (1991) Yeast 7 575–787,] and after temperature shift-ups to about 40° C. [De Virgilio, C. Simmen, U. Hottiger, T. Boller, T. & Wiemken, A. (1990) Federation of European Biochemical, Societies Letters 273, 107–110]. Panek and her colleagues [Panek, A. C., de Araujo, P. S., Neto, M. V. & Panek, A. D. (1987) Current Genetics 11, 459–465] have claimed that TPS activity is increased by dephosphorylation of pre-existing enzyme molecules, i.e., that it is the result of post-translation regulation. This claim has been challenged [Vandercammen, A., et al., (1989) European Journal of Biochemistry 182, 613–620] but continues to be made [Panek, A. D. & Panek, A. C. (1990) Journal of Biotechnology 14, 229–238]. Evidence for or against an increase in the amount of enzyme during trehalose accumulation is conflicting. Inhibitors of mRNA synthesis inhibited trehalose accumulation by *S. cerevisiae* shifted from 30° to 45° C. [Attfield (1987) loc.cit.] whereas under very similar conditions [Winkler et al [1991] loc.cit.] found that cycloheximide (an inhibitor of protein synthesis) did not prevent the accumulation of trehalose, which, however, occurred without an observable increase in TPS activity. In a lower temperature range (a shift from 23° to 36° C.), trehalose accumulation was accompanied by a three-fold increase in TPS activity, and cycloheximide prevented the increase in TPS [Panek, A. C., Mansure Vânia, J. J., Paschoalin, M. F. and Panek, A. (1990) Biochemie 72, 77–79]. In *Schizosaccharomyces pombe*, temperature shift-up caused a large accumulation of trehalose and increase of TPS which were not prevented by cycloheximide, leading the authors to suggest that in this yeast a post-translational activation occurs. We now disclose that in *S. cerevisiae* the co-ordinate increases in TPS and TPP activities during exhaustion of glucose are accompanied by an increase in antigenic material recognized by anti-sera to the short and long chains of a purified trehalose synthase. Hence, a method to increase the trehalose content of cells would be to isolate, clone, and modify the structural genes (hereinafter referred to as TSS1 and TSL1) of these polypeptides and cause their expression in yeast or other host cells under the control of suitable promoters. If the expression of these genes could be controlled, then so could the trehalose content of the host cells.

Expression of the genes for trehalose synthesis in yeast under conditions where trehalase is active will increase the operation of a so-called "futile" cycle, in which glucose is continuously phosphorylated, converted to trehalose and regenerated by hydrolysis of the trehalose, resulting in increased consumption of ATP. This ATP must be regenerated, and under fermentative conditions this will occur by conversion of sugars into ethanol. Therefore, introduction of TSS1 and TSL1 into yeast under the control of promoters active under fermentative conditions is expected to decrease the yield of cell mass on carbon source and increase that of ethanol. The present invention includes transformed strains of distiller's yeast, in which the presence of modified forms of TSS1 and TSL1 results in an increased yield of ethanol from carbohydrate sources.

As well as being used to improve the storage properties of yeast, especially active dried yeast and yeast for frozen doughs, this invention has other obvious applications. First, by increasing the proportion of trehalose in yeast, the industrial scale production of trehalose from yeast is made more economic. It is particularly advantageous to obtain trehalose from yeast because, since yeast is a traditional and safe food stuff, a minimal purification of the trehalose will often be adequate: preparations of trehalose containing yeast residues could be safely added to food stuffs for human or animal consumption. Trehalose also has medical applications, both as a stabilizer of diagnostic kits, viruses and other protein material [WO 87/00196] and, potentially, as a source of anti-tumour agents [Ohtsuro et al (1991) Immunology 74, 497–503]. Trehalose for internal applications in humans would be much more safely obtained from yeast than from a genetically engineered bacterium.

Second, by transferring these genes to higher plants after making suitable modifications obvious to anyone skilled in the art (in general, replacements of adenine/thymine base pairs by guanine/cytosine base pairs as suggested by Perlak et al [(1991) Proceedings of the National Academy of Sciences of the U.S.A. 88, 3324–3328] and the introduction of suitable promoters, some of which may be tissue-specific, to direct the synthesis of trehalose to frost- and drought-sensitive tissues), the resistance of the plants to various stresses, especially frost and dehydration, should be improved. The economic importance of such improvements is potentially enormous, because even small increases in cold-tolerance will lead to large increases in growing season, whereas dehydration resistance can save entire crops in time of drought. Frost and drought resistance in higher plants is usually accompanied by increases in compounds such as proline rather than trehalose [reviewed by Stewart (1989) in "Plants under Stress, pp 115–130], but, as mentioned above, resurrection plants accumulate large amounts of trehalose and there seems, a priori, to be no reason why this strategy should not be successful. Therefore, the present invention includes a process to transform crop plants by introducing recombinant forms of the structural genes of yeast trehalose synthase (TSS1 and TSL1) so as to increase the trehalose content of some of their tissues compared to those of the parent plant. Third, the shelf-life of food products can be increased by adding trehalose to them [WO 89/00012]. A further aspect of the present invention is a novel process for producing trehalose-enriched food products from plants by causing them to express the structural genes for yeast trehalose synthase in their edible tissues.

SUMMARY OF INVENTION

The present invention provides two isolated genes coding for the short and long chains of yeast trehalose synthase. These genes can be used to transform an organism (such as a yeast, other fungus or higher eukaryote), whereby the transformed organism produces more trehalose synthase resulting in a trehalose content higher than the parent organism. The higher trehalose content confers improved stress resistance and storage properties of the transformed organism as compared to the parent organism. The genes can also be used to produce large quantities of trehalose by fermenting a bacteria or yeast transformed with appropriate vectors expressing the genes.

BRIEF DESCRIPTION OF FIGURES

FIG. 1 SDS-PAGE of native trehalose synthase.

A 6-13% T (Total concentration of acrylamide+bisacrylamide) gradient gel was used. Lane 1 contains 8.3 µg of native trehalose synthase eluted from the UDPG-Glucuronate-Agarose column with 0.2M NaCl (#11 of Table 1). Lanes 2,3 and 4 contain, respectively, 7.7, 12 and 1.0 µg of enzyme eluted from the column with 0.4M NaCl containing 10 mM UDPG (#13, #14 and #15 from Table 1). Lane 5 contains about 1 µg each of molecular mass markers (myosin, β-galactosidase, α-phosphorylase, BSA, ovalbumin, lactate dehydrogenase, triosephosphate-isomerase, myoglobin and cytochrome c). The major polypeptides of native trehalose synthase are named on the left and the molecular mass calibration, in kDa, is shown on the right.

FIG. 2 SDS-PAGE of immunoprecipitates of wild-type yeast grown on YP/2% glucose.

A 9% T gel was used. Lane 1 contains about 1 µg each of the molecular mass markers used in FIG. 1. Lanes 2,3 and 4 contain immunoprecipitates from 3.8 mg fresh yeast harvested after 16.1 h (1.2% residual glucose), 18.1 h (no residual glucose) and 39 h. The molecular mass calibration is shown on the left and the major polypeptides of trehalose synthase and the heavy chain of γ-globulin are shown on the right.

Figure 3:
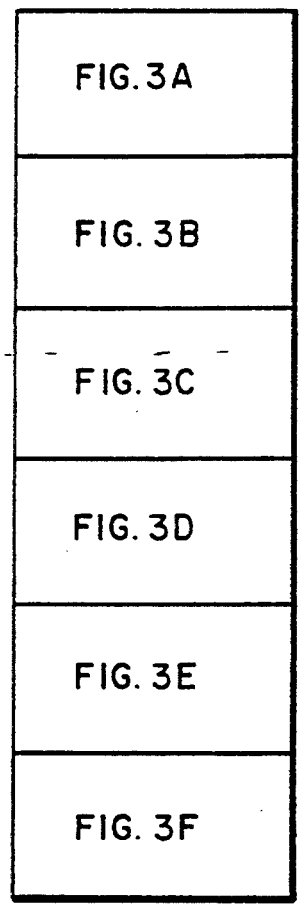
Figure 3E:
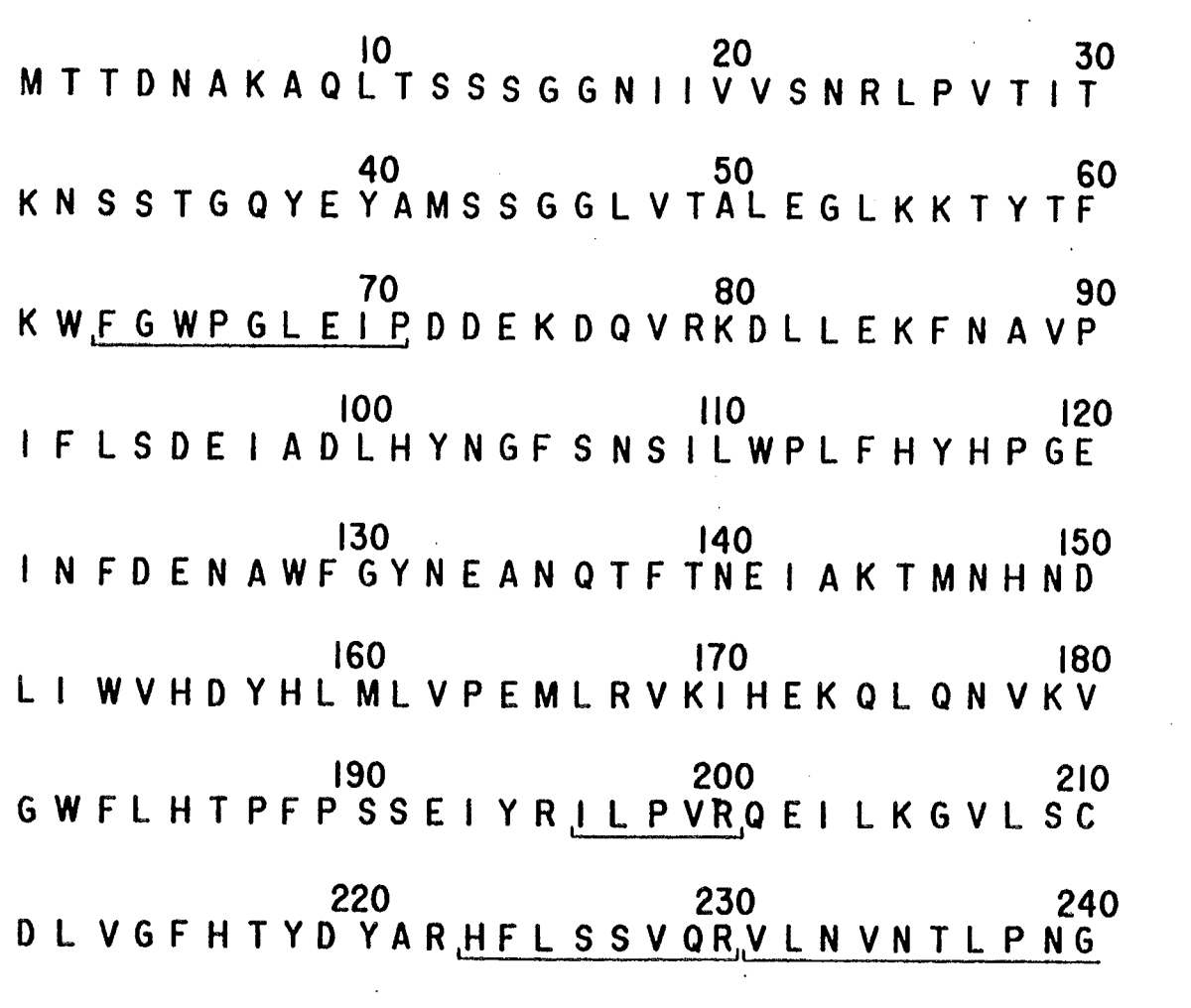
Figure 3F:
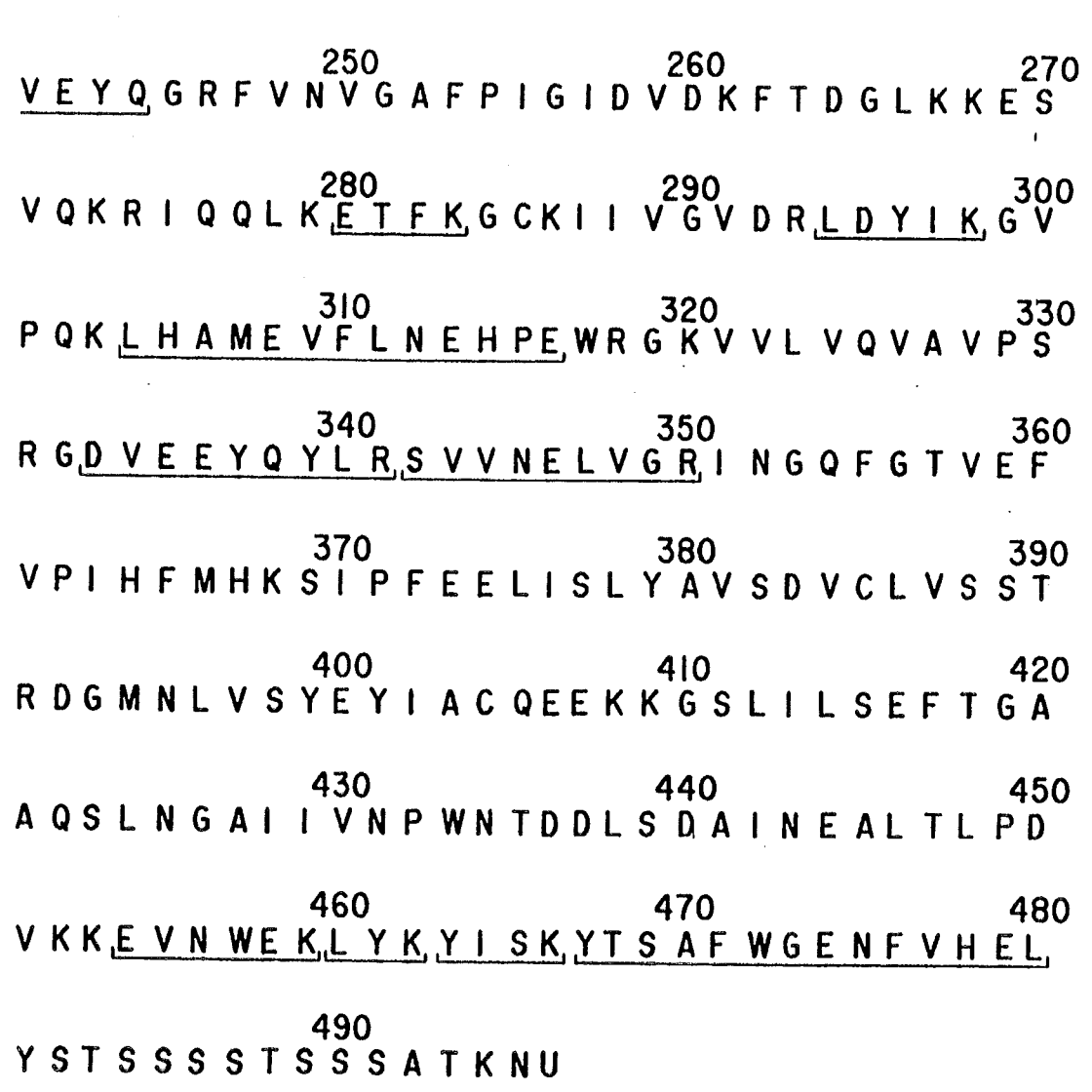

FIG. 3 Nucleotide sequence of TSS1 and deduced amino acid sequence of the short chain of trehalose synthase. FIGS. 3A-3D illustrate the nucleotide sequence. FIGS. 3E and 3F illustrate the amino acid sequence.

In the nucleotide sequence (SEQ ID NO:1) the start ATG and the tandem TGA stop codons are double underlined and a TATA box and putative catabolite repression element are underlined. In the deduced amino acid sequence (SEQ ID NO:2) the sequences are found from the peptides isolated from the short chain of trehalos synthase and are underlined (U=untranslated).

Figure 4:
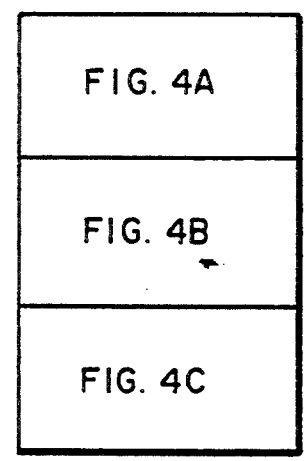

FIG. 4 The amino acid sequence deduced from the nucleotide sequence of the 3'-terminal portion of TSL1. FIG. 4A-4C illustrate the sequence.

In this sequence (SEQ ID NO:4), the sequences of peptides found in the complete and truncated versions of the long chain of trehalose synthase are underlined (U=untranslated). The corresponding nucleotide sequence is SEQ ID NO:3.

Figure 5:
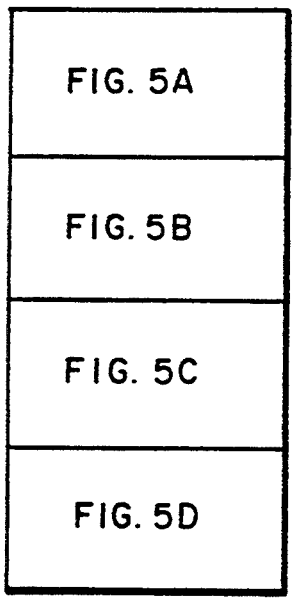

FIG. 5 Alignment of the amino acid sequences of the short and long chains of trehalose synthase. FIG. 5A-5D illustrate the sequence.

The complete short chain sequence (SEQ ID NO:2; the upper sequence) is aligned against the first 502 residues of SEQ ID NO:4 (the lower sequence), which is from the C-terminal portion of the long chain, 36 gaps being introduced to optimize the alignment. Vertical dashes indicate identical residues. Colons indicate conservative substitution.

FIG. 6 Important restriction sites in TSS1 and TSL1.

Important restriction sites in TSS1 and the 3'terminal portion of TSL1 are shown. The heavy lines indicate open reading frames. The scale bar shows one kb.

FIG. 7 Synthesis of [$^{14}$C]-trehalose from [U-$^{14}$C]-glucose 6-phosphate by an extract of wild-type yeast.

Reaction mixtures (100 µl) contained 40 mM HEPES/KOH pH 6.8, 1 mg BSA/ml, 10 mM MgCl$_2$ 10 mM [U-$^{14}$C]-G6P (736 c.p.m./nmol) and (a) no phosphate or (b) 5 mM K phosphate pH 6.8 and (0) 5 mM UDPG, ( ) 2.5 mM ADPG or (□) neither UDPG nor ADPG. Reactions were started by adding 10 µl (equivalent to 94 µg fresh yeast) of a 28,000 g supernatant of stationary phase X 2180. Reactions were stopped by transfer to boiling water for 2 min and addition of 1.0 ml of a slurry of AG1-X8 (formate) anion exchange resin [Londesborough & Vuorio (1991) loc. cit.]. The radioactivity in the resin supernatant was measured.

Figure 8:
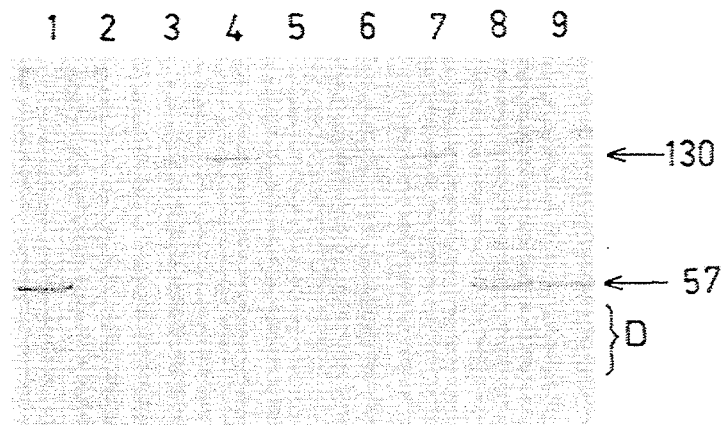

FIG. 8 western analysis of Klg 102 and X2180 yeasts.

Growth of the yeasts is described in Example 7. The loads of fresh yeast per lane were: lane 1, 200 µg X2180/2; lanes 2 and 5, 330 µg 2669/1; lanes 3 and 6, 610 µg 2669/2; lanes 4 and 7, 810 µg 2670/1+2; lane 8, 560 µg X2180/1 and lane 9, 280 µg X2180/1. The blot was probed with anti-TPS/P serum at a dilution of 1/30 000. Major bands of trehalose synthase are identified on the right.

Figure 9:
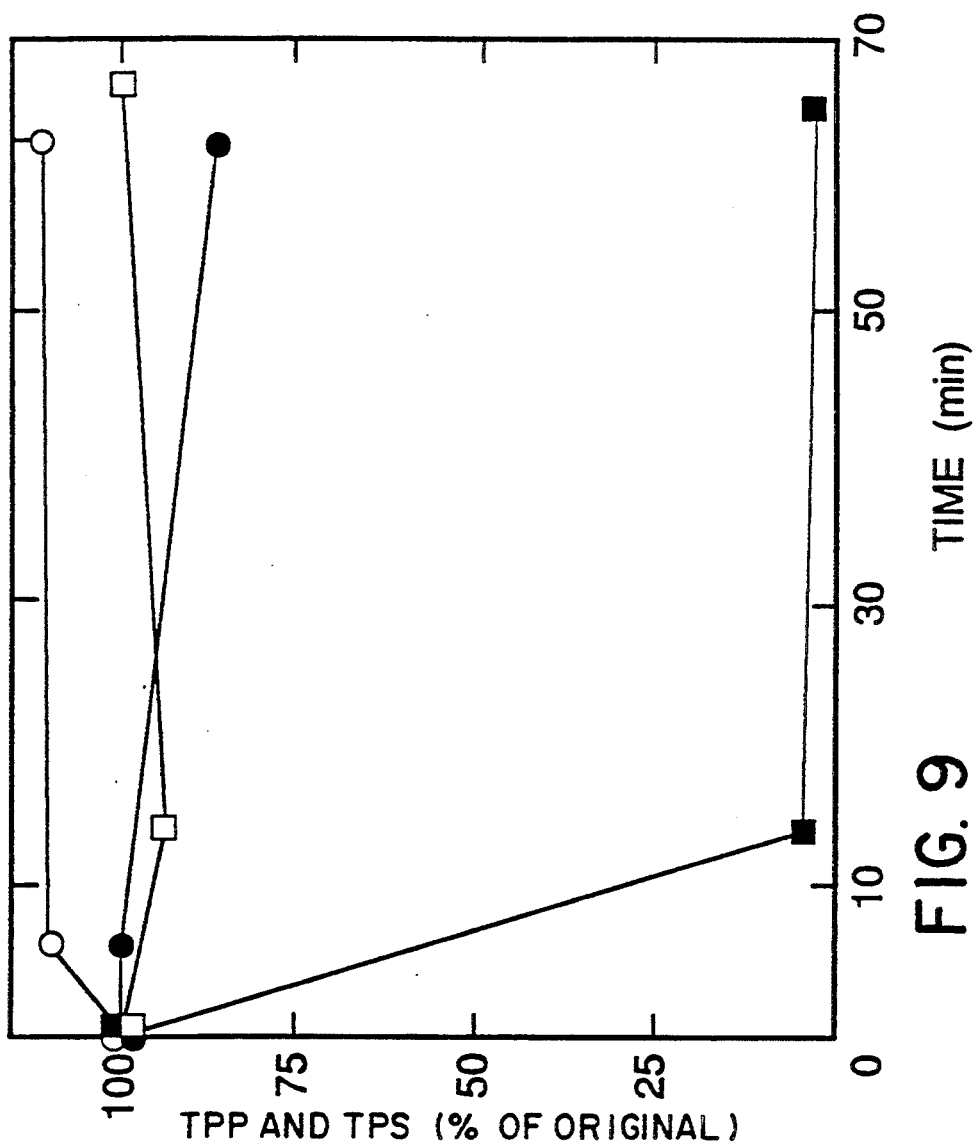

FIG. 9 Treatment of truncated trehalose synthase with 1.9 mM NEM

Truncated enzyme (0.13 TPS units/ml≈43 µg/ml) in 2 mg BSA/ml 50 mM HEPES pH 7.0 containing 67 mM NaCl, 0.2 mM EDTA, 0.17 mM dithiothreitol, 0.17 mM benzamidine and 1.7 mM UDPG was incubated at 24° C. with (closed symbols) or without (open symbols) 1.9 mM NEM. TPS ( ,0] and TPP ( ,□) activities were measured.

Figure 10:
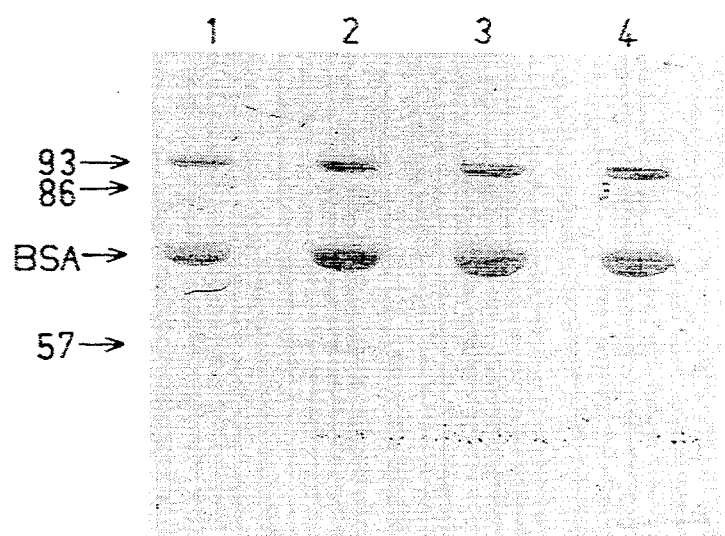

FIG. 10 Autoradiogram of truncated trehalose synthase labelled with [$^{14}$C]-NEM and separated by SDS-PAGE.

Labelling was performed as described in Example 8 for 1.5, 10.5, 63 and 190 min in lanes 1,2,3 and 4, respectively. The positions of the (57 kDa) short chain, 93 and 86 kDa fragments of the long chain and the carrier BSA are indicated.

Figure 11:
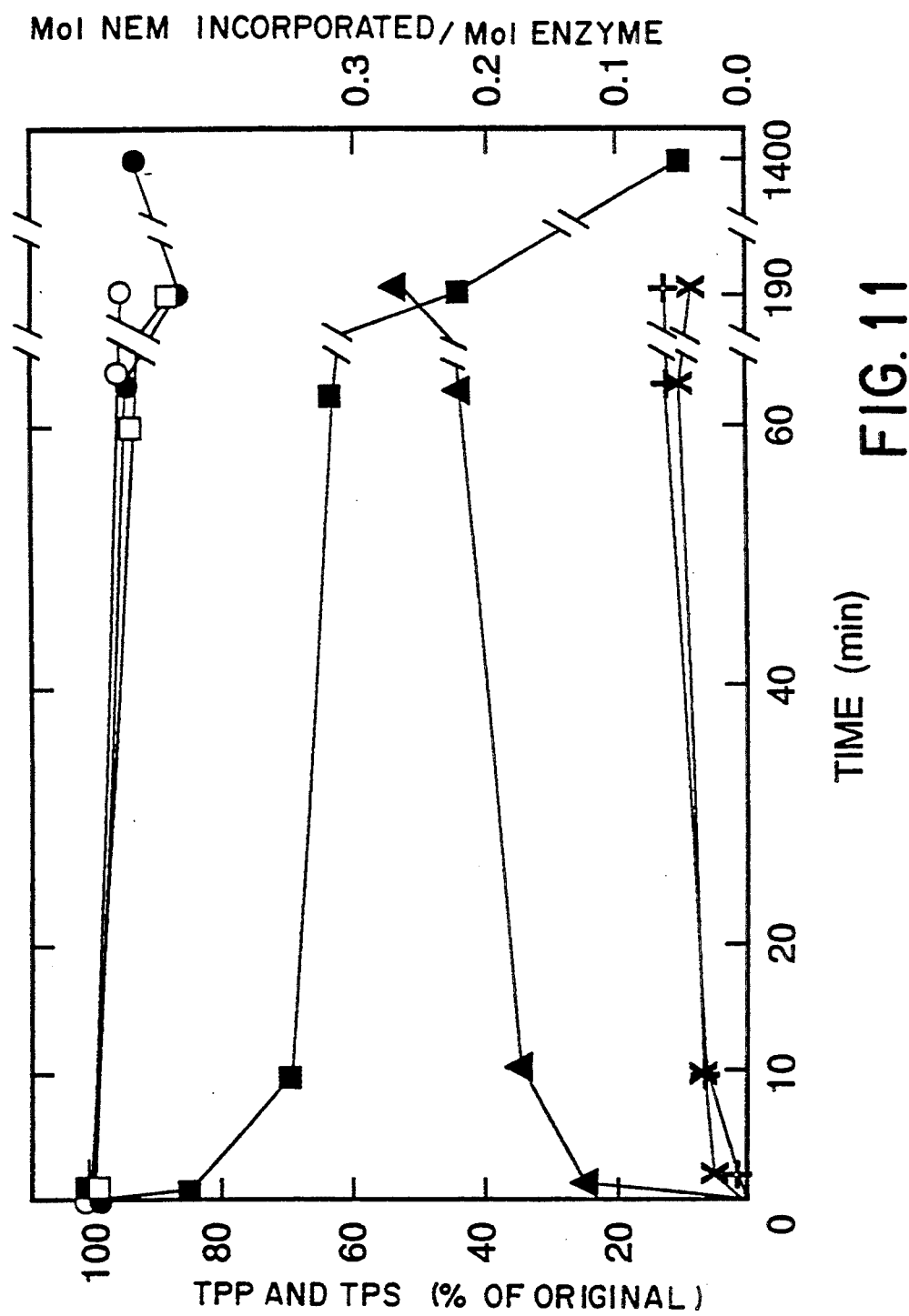

FIG. 11 Treatment of truncated trehalose synthase with ethyl-labelled NEM.

Truncated enzyme (7.2 TPS units/ml≈0.24 mg/ml) in 1 mg BSA/ml 25 mM HEPES pH 7.0 containing 2 mM MgCl$_2$, 1 mM EDTA and 0.2M NaCl was incubated at 23° C. with (solid symbols) or without (open symbols) 32 µM ethyl-labelled NEM. TPS ( ,0) and TPP ( ,□) activities and the amount of [$^{14}$C]-NEM incorporated into the 93 ( ), 86 (+) and 57 (X) kDa polypeptides were measured. 0.1 mol NEM incorporated per mol (150 Kg) of enzyme corresponds to an excess radioactivity of 75 c.p.m. in bands cut from the gel.

Figure 12:
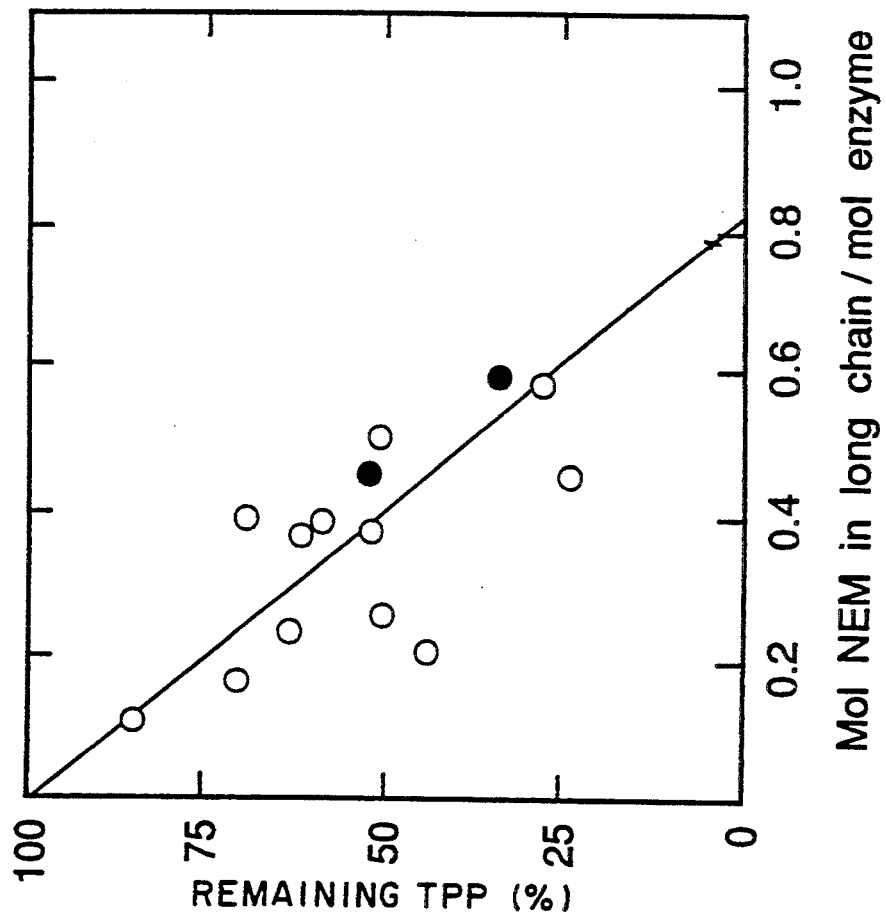

FIG. 12 Stoichiometry of NEM labelling.

Residual TPP activity is plotted against the amount of NEM incorporated to the 93 and 86 kDa fragments of the long chain. Ring-labelled ( ) and ethyl-labelled (0) NEM were used.

Figure 13:
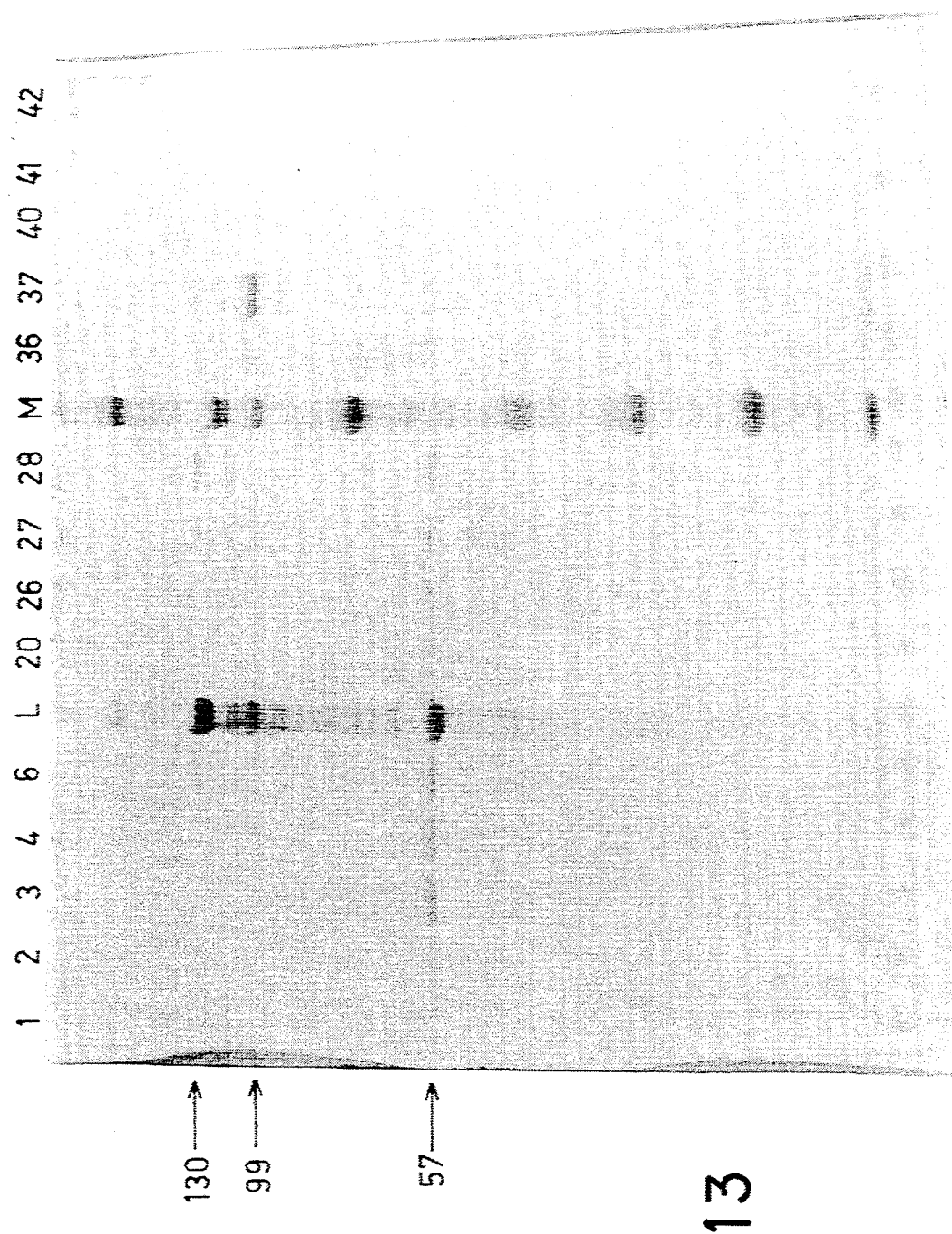

FIG. 13 SDS-PAGE analysis of fractions eluted from the cellulose-phosphate column.

Lane L contains 47 μl of the native trehalose synthase applied to the column. Lane M contains about 1 μg each of the molecular mass markers used in FIG. 1. The numbered lanes contain 33 μl of selected 1.5 ml fractions eluted from the column. The NaCl gradient began to appear in fraction 6 and reached 300 mM at fraction 27. A step to 600 mM NaCl emerged between fractions 36 and 37. Fractions 40 to 42 were eluted with 200 mM K phosphate. The major bands in the trehalose synthase preparation are identified on the left. Details are given in Example 9.

Figure 14:
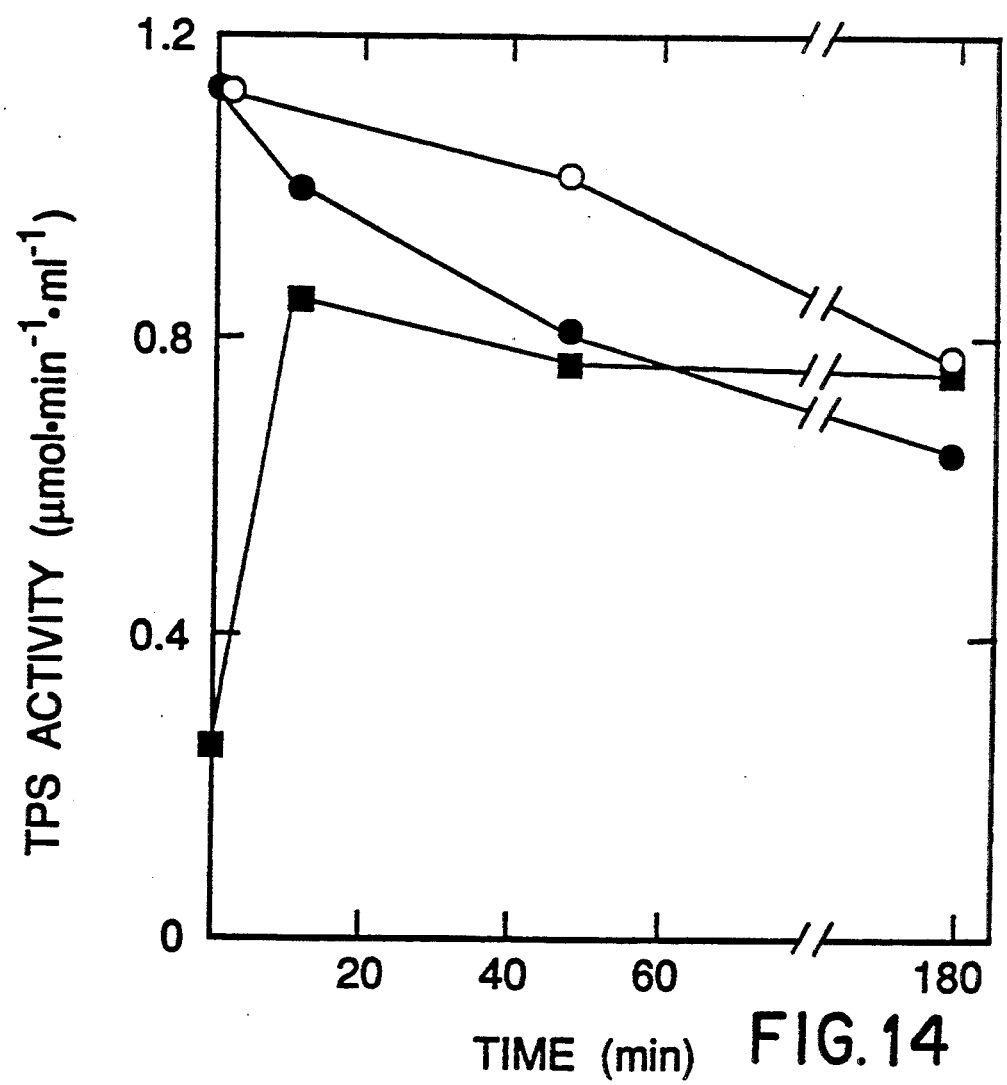

FIG. 14 In vitro activation of trehalose synthase by limited tryptic digestion.

Native trehalose synthase was incubated with (solid symbols) and without (open symbols) trypsin and its TPS activity measured in the presence of 5 mM F6P in reaction mixtures containing (0,●) no phosphate or (●) 5 mM K phosphate pH 6.8. Details are given in Example 10.

Figure 15:
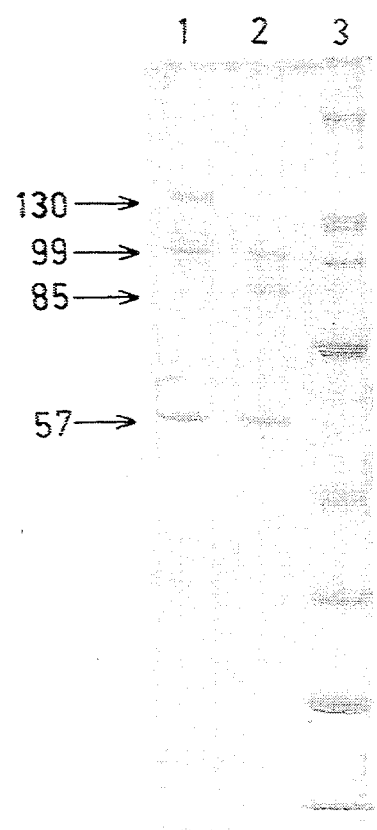

FIG. 15 Limited tryptic digestion of native trehalose synthase.

Lane 1 contains the untreated trehalose synthase used in FIG. 15 and lane 2 the same amount of enzyme after 48 min treatment with trypsin. Lane 3 contains molecular mass standards. The major polypeptides of trehalose synthase are identified on the left.

Figure 16:
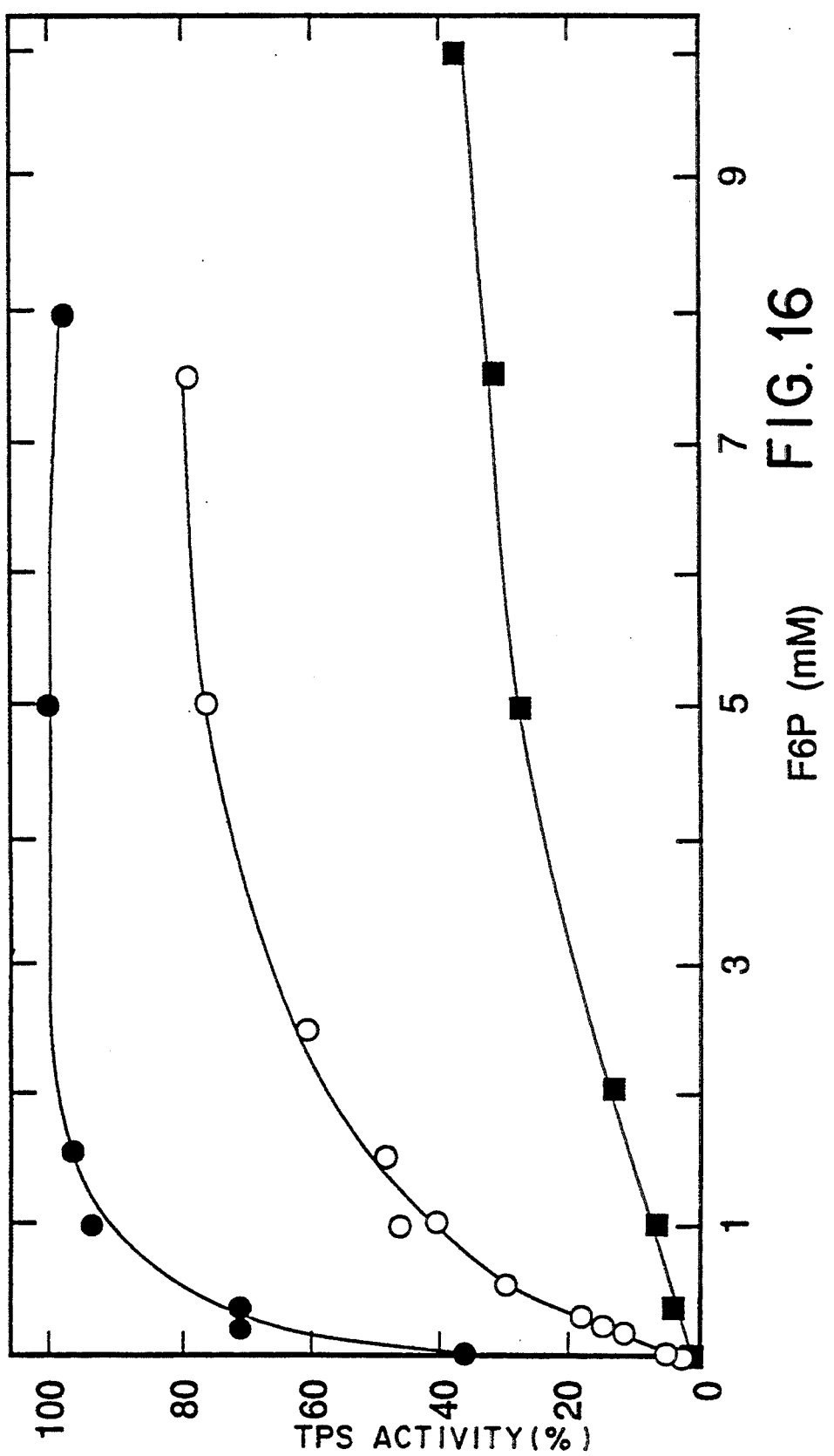

FIG. 16 The effect of fructose 6-phosphate on the TPS activity of native trehalose synthase at different phosphate concentrations.

The TPS activity of native trehalose synthase was measured between zero and 10 mM F6P. Other conditions were as in the standard TPS assay with (●) no changes, (0) 13 mM K phosphate pH 6 8 added or (●) 4 mM K phosphate pH 6.8 and 0.1M KCl added and the $MgCl_2$ concentration decreased to 2.5 mM. Activities are shown as percentages of that in the standard assay (i.e., at 5 mM F6P and no phosphate).

Figure 17:
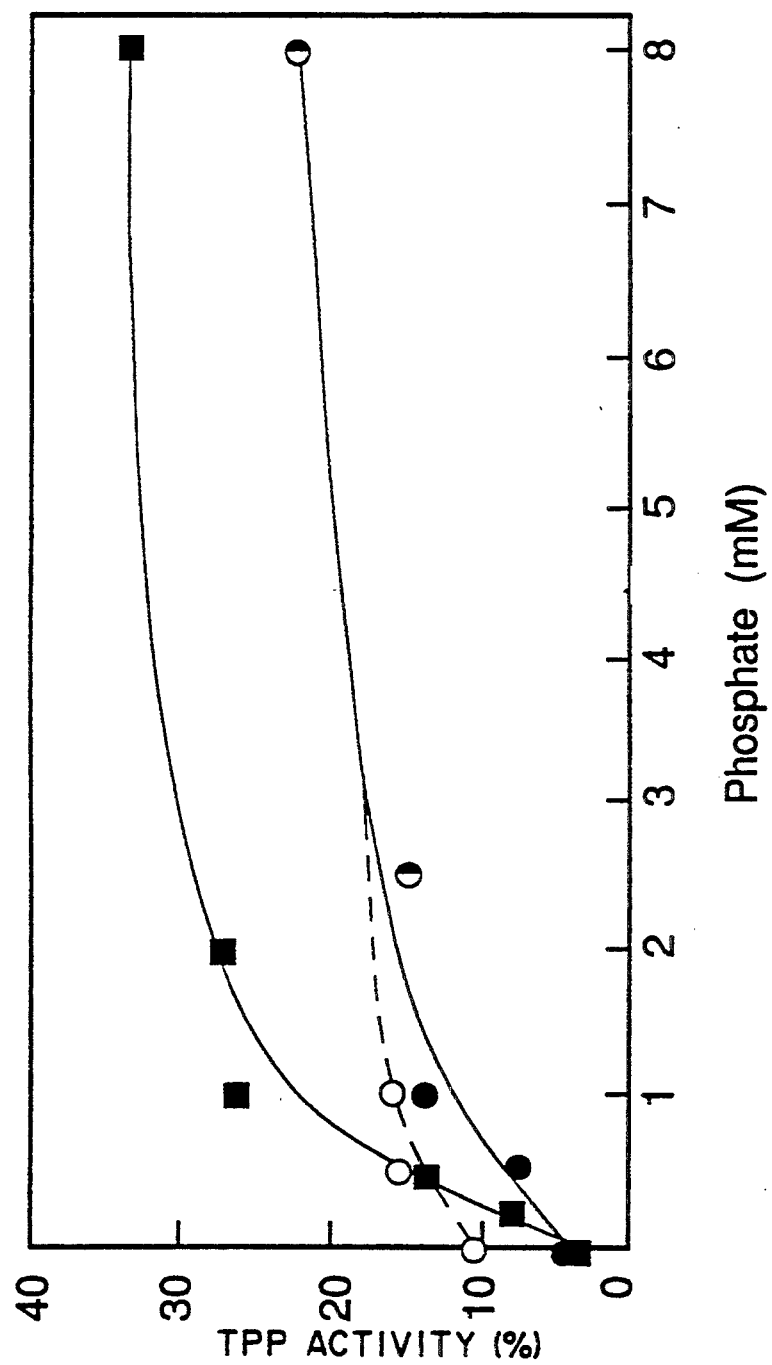

FIG. 17 Activation of the TPP activities of native and truncated trehalose synthase by phosphate.

TPP activities were measured in standard assay mixtures containing the indicated concentrations of K phosphate pH 6.8 and are shown as percentages of the standard TPS activity. Initial rates are shown for the (●) native and (●) truncated enzyme. Rates during the second five minutes of the accelerating reaction obtained with truncated enzyme are also shown (0).

FIG. 18 Phosphate-dependence of the TPP activity of native trehalose synthase.

The reciprocal of the increase in rate ($V_A$) caused by the phosphate is plotted against (0) $[phosphate]^{-2}$ or (●) $[phosphate]^{-1}$. $V_A$ is shown as a percentage of the standard TPS activity.

DETAILED DESCRIPTION OF THE INVENTION

In the following description, trehalose-6-phosphate synthase (TPS) and trehalose-6-phosphate phosphatase (TPP) refer to catalytic activities, not to proteins, unless specifically stated otherwise, whereas trehalose synthase refers to a protein that can convert uridine diphosphoglucose (UDPG) and glucose-6-phosphate (G6P) into trehalose, and also exhibits as partial reactions TPS and TPP activities. TSS1 and TSL1 are structural genes that encode, repectively, the short (57 kDa) and long (about 130 kDa) chains of trehalose synthase.

The present inventors previously reported the isolation of a partially degraded protein preparation that contained a short (57 kDa) polypeptide chain and two fragments (86 and 93 kDa) of a long polypeptide chain and possessed both TPS and TPP catalytic activities [(1991) Journal of General Microbiology 137, 323–330]. The size of the full-length, native long chain, and whether one or other polypeptide possessed one or other of the catalytic activities were not known at that time.

The present inventors have now isolated an undegraded trehalose synthase that contains a 57 kDa short chain and a long chain of about 130 kDa as its major polypeptides. A 99 kDa polypeptide and traces of other polypeptides are also present that appear to be degradation products of the long chain. Two genes, TSS1 and TSL1, that encode, respectively, the short and long chains have now been cloned. The complete sequences (SEQ ID NOs: 1 and 2, respectively) of TSS1 and the polypeptide it encodes are shown in FIG. 3. About 65% of the sequences of TSL1 and the polypeptide it encodes are disclosed as SEQ ID NO:3 and SEQ ID NO: 4, respectively, the latter also being shown in FIG. 4. Genetic evidence is presented herein that shows that a functional TSS1 gene is required for the expression of both TPS and TPP catalytic activities in *S. cerevisiae*: both activities are absent from a mutant strain (Klg 102) that lacks a properly functional TSS1 gene and does not express the short chain in a form recognizable in Western blots although it does express immunologically recognisable long chain. We disclose biochemical evidence that the TPP catalytic activity of a truncated trehalose synthase requires a functional long chain: incorporation of about 1 mole of $^{14}C$-N-ethylmaleimide into the long chain fragment per mole of trehalose synthase results in complete loss of TPP activity but only a slight loss of TPS activity. Furthermore, under special conditions we have been able to isolate the 99 kDa polypeptide, which is believed to be a truncated form of the long chain, and show that it possesses residual TPP activity but no TPS activity (this does not contradict the above finding that yeast lacking a functional TSS1 gene is not able to assemble a stable, functional protein with TPP activity). Nevertheless, we show that truncation of the long chain has dramatic and important effects on the TPS activity of trehalose synthase: appropriate truncation greatly decreases the sensitivity of the TPS catalytic activity to inhibition by phosphate and essentially completely eliminates its activation by fructose-6-phosphate.

Thus, both the short and the long chain make essential contributions to both the TPS and the TPP catalytic activities of trehalose synthase. The situation is therefore that there are two different structural genes for a trehalose synthase, neither of which can be accurately described as the structural gene of either a trehalose-6-phosphate synthase protein or a trehalose-6-phosphate phosphatase protein. We disclose that these two genes contain extensive similarities such that the amino acid sequence of the entire short chain is 34% identical to a corresponding portion of the long chain.

A novel feature of the present invention, therefore, is that in order to increase the capacity of a yeast or some other host organism for trehalose synthesis it will generally be necessary to increase the expression of both the TSS1 and TSL1 genes or modify these genes in some other way, not because either TPS or TPP activity is "rate-limiting", but because both activities depend on both genes. It will now be obvious to a person familiar with the art that special organisms will exist (such as the yeast mutant, Klg 102) in which one or other gene is defective in such a way that both catalytic activities can be increased by transformation with a functional version of the defective gene.

A surprising finding was that the TSS1 gene is identical with a gene variously called FDP1 or CIF1. This gene has pleiotropic effects on the utilization of sugars by S. cerevisiae. In particular, haploid yeast bearing certain alleles of this gene (the so-called fdp1 and cif1 mutants) are unable to grow on mannose, or on mannose or sucrose, or on mannose, sucrose or fructose, or on mannose, sucrose, fructose or glucose, depending upon the severity of the defect [Van de Poll & Schamhart, (1977) Molecular and general Genetics 154, 61–66; Banuelos, M. & Fraenkel, D. G. (1982) Molecular and Cellular Biology 2, 921–929]). Such mutants grow normally on galactose. Therefore, during the selection of strains in which the TSS 1 gene has been deleted or modified it is sometimes essential and always advisable to grow the transformants on galactose, because in many cases the desired transformant will be unable to grow on any other common sugar, including the routinely used glucose. This is an unexpected methodological consideration that would not be obvious even to a person skilled in the art: special knowledge about the sequence and chromosomal location of the TSS 1 gene is required, which we now disclose.

At present only one gene (TSL1) for the long chain of trehalose synthase has been cloned and partially sequenced. Findings disclosed here indicate that a second gene may exist. Thus, the purified preparations of trehalose synthase contain, in addition to the 130 kDa long and 57 kDa short chains, a 99 kDa polypeptide. Surprisingly, amino acid sequence analysis of peptides from this 99 kDa polypeptide provide little evidence that it would be a degradation product of the 130 kDa long chain, although they do not yet exclude this possibility. If the complete sequence of TSL1 shows that the 99 kDa polypeptide cannot be a degradation product of the 130 kDa long chain, then the gene ("TSL2") for the 99 kDa polypeptide will be cloned using the amino acid sequences from this polypeptide herein disclosed. A method for the partial resolution of trehalose synthase into a 99 kDa enriched form and a 130 kDa-enriched form (both also containing the short chain) is disclosed, and by using this method we found that the catalytic properites (in particular, the TPP/TPS activity ratio) of the two forms differ. Therefore, depending upon the particular circumstances, it may be advantageous to transform organisms with either a combination of TSS1 and TSL1 genes or of TSS1 and TSL2 genes.

The inventors' previous work [Londesborough & Vuorio (1991) loc. cit.] showed that the TPS catalytic activity of what is now known to be trehalose synthase requires a so-called TPS-Activator protein, which is a dimer of 58 kDa subunits. We have now identified this protein by the amino acid sequences of peptides it contains and by its catalytic activity and disclose that it is yeast phosphoglucoisomerase. We disclose that fructose-6-phosphate, which could be made by phosphoglucoisomerase from the glucose-6-phosphate in the assay mixtures used to measure TPS activity, is a powerful activator of the TPS activity of native trehalose synthase. Furthermore, the TPS activity of truncated trehalose synthase does not require fructose-6-phosphate, and is not so strongly inhibited by phosphate as is that of the native enzyme. Thus, a trehalose synthetic pathway can in principle be transferred to any organism by transforming the organism with the structural genes for yeast trehalose synthase: it is not necessary to simultaneously introduce the TPS-activator, because fructose-6-phosphate is a ubiquitous component of cells. Furthermore, if the amounts of fructose-6-phosphate in an organism are inadequate, or phosphate concentrations are too high, the organism can be transformed with TSS1 and a truncated version of TSL1 encoding for the truncated long chain that confers insensitivity to phosphate and fructose-6-phosphate. This aspect of the present invention is particularly significant, because it allows both the introduction of a trehalose synthetic pathway to organisms in which the cytosolic phosphate and fructose-6-phosphate concentrations would prevent the efficient function of yeast trehalose synthase, and also may permit trehalose synthase to function efficiently at stages of yeast growth when native trehalose synthase would be inhibited by cytosolic phosphate. We disclose that native trehalose synthase can be liberated from phosphate inhibition by treatment with trypsin in vitro.

From the knowledge gained from the present invention, it is possible to produce trehalose recombinantly by transforming a host cell with the TSS1 and TSL1 genes. Methods of transformation and appropriate expression vectors are well-known in the art. Although only 65% of the TSL1 DNA and polypeptide sequences have been uncovered to date, those of ordinary skill in the art could utilize the sequence known to probe for the entire TSL1 gene for use in an expression vector.

Expression vectors are known in the art for both eukaryotic and prokaryotic systems, and the present invention contemplates use of both systems. Also contemplated are modifications of the DNA sequence which would provide "preferred" codons for particular expression systems (e.g., bacteria and higher plants). In addition, the TSS1 and TSL1 DNA sequences may be modified by certain deletions or insertions, provided the translated polypeptides are enzymatically functional. Expression of functional polypeptides of TSL1 and TSS1 may be confirmed by assaying for TPS and/or TPP activity in the expression system by the methods described in Londesborough and Vuorio [(1991) loc. cit.].

It has already been mentioned that truncation of the 130 kDa long chain generates an enzyme with TPS activity relatively insensitive to inhibition by phosphate and not activatable by F6P. Methods are described that will locate the site or sites of this truncation, and appropriate deletions may be made in TSL1 so that organisms transformed with the modified gene can express a trehalose synthase with these advantageous properties. As another example, the DNA can be manipulated by inserting sequences that code for basic amino acids at one end of the polypeptide to facilitate purification of the enzyme.

The genes of the present invention may be transferred and expressed in plants by using the Ti plasmid system which is well known in the art. The internal transforming genes of a cloned T-DNA can be removed by recombinant DNA techniques and replaced by the genes of the present invention and expressed in plant tissues. Commonly, the coding sequence of the foreign gene (in this instance, TSL1 and TSS1) is substituted for the coding region of the opine synthetase gene. In this way, the natural promoter and polyadenylation signals of the opine synthetase gene confer high-level expression of the foreign protein. Any method known in the art, however, may be used to transform higher plants with the genes of the present invention.

The following examples are for illustration of the present invention and should not be construed as limiting the present invention in any manner.

EXAMPLES

General Methods and Materials

Materials.

Fructose 6-phosphate (F6P) and adenosine 5'-diphosphoglucose (ADPG) were from Sigma Chemicals. Glucose 6-phosphate (G6P), phenylmethylsulphonyl fluoride (PMSF), uridine 5'-diphosphoglucose (UDPG) and other commercial reagents were from the sources stated in Londesborough & Vuorio [(1991) loc. cit.]. Truncated trehalose synthase (proteolytically activated "TPS/P") and TPS activator were prepared as described in Londesborough & Vuorio [1991] loc. cit.]. The antisera, anti-TPS/P, anti-57K and anti-93K were made in rabbits using as antigen, respectively, truncated trehalose synthase and the short (57 kDa) chain or the 93 kDa fragment of the long chain of trehalose synthase as described in Londesborough & Vuorio [(1991) loc. cit.].

Yeasts.

Commerical baker's yeast was from Alko's Rajamäki factory. The standard laboratory strains of S. cerevisiae used were X2180 (ATCC 26109) and S288C (ATCC 26108). Mutant strains are described in the Examples. Laboratory yeast were routinely grown on 1% yeast extract/2% peptone (YP) containing the indicated sugar in aerobic shake flasks at 30° C. and 200 r.p.m. Cells were harvested by centrifugation for 5 minutes at 3000 g, resuspended in distilled water and again centrifuged 5 minutes at 3000 g. The pellets were suspended in about 20 volumes of 25 mM HEPES/KOH pH 7.0 containing 1 mM benzamidine, 2 mM $MgCl_2$, 1 mM EDTA and 1 mM dithiothreitol (HB2M1ED) and centrifuged in tared tubes for 10 minutes at 15,000 g. Tubes and pellets were weighed to give the mass of fresh yeast. For trehalose determinations, portions of the pellets were treated as described by Lillie, S. H. & Pringle, J. R. [(1980) Journal of Bacteriology 143, 1384–1394]. The washed cells were broken by suspending them at 0° C. in 1 to 4 volumes of HB2M1ED, adding fresh stock PMSF/pepstatin (1 mg pepstatin A/ml 0.1M PMSF in methanol) to give final concentrations of 10 μg pepstatin/ml and 1 mM PMSF, and shaking with glass beads for three 1 minute periods in a Braun MK II homogenizer. The glass beads were removed and the volume of homogenate was measured. Samples for SDS-PAGE were made at once by dilution with Laemmli sample buffer [Laemmli, U. K. (1970) Nature, London 227, 680–685]. The homogenates were then centrifuged for 20 minutes at 28,000 g and enzyme assays were made on the supernatants.

Enzyme Assays.

TPP and TPS standard assays and other kinetic measurements were made as described by Londesborough & Vuorio [(1991) loc. cit.] except that the standard TPS assay mixture contained 5 mM F6P unless stated otherwise.

DNA manipulations.

Stratagene's (La Jolla, Calif.) Escherichia coli strain XL-1 Blue (recA1, endA1, gyrA96, thi, hsdR17, supE44, relA1, lac, {F' proAB, lacIq ADM15, Tn10 (tetR)}) were used as host bacteria. When needed, XL-1 Blue cells were made competent by the method of Mandel & Higa [(1970) Journal of Molecular Biology 53, 159–162]. The cloning vector was Stratagene's Lambda Zap II, predigested with EcoRI, where the cloning site is near the N-terminus of the gene for B-galactosidase, thus enabling the color selection of recombinant clones. The sequencing vectors M13mp18 and M13mp19 from Pharmacia LKB Biotechnology were also used.

High molecular mass DNA from the haploid S288C strain was prepared as described [Johnston, J. R. (1988) in Yeast, A Practical Approach, IRL Press, Oxford] and partially digested with either HaeIII or EcoRI restriction enzyme. For the large scale HaeIII digestion, e.g., a reaction mixture of 330 μl containing 30 μg of DNA and 4.8 U of enzyme was incubated at 37° C. for 60 minutes. The reaction was stopped with 10 μl of 0.5M EDTA and transferred to ice. The methods for such digestions and their agarose gel electrophoretic analysis are well known in the art and are described, e.g., in Sambrook et al, Molecular Cloning, A Laboratory Manual [Cold Spring Harbor Laboratory Press, 2nd ed., (1989)].

Plasmid DNA was isolated using standard methods for small scale purification [Sambrook et al (1989) Molecular Cloning, A Laboratory Manual, 2nd ed., Cold Spring Harbor Laboratory Press, hereby expressly incorporated by reference]. Large scale purifications of plasmid DNA were done with Qiagen tip-100 columns from Diagen following their instructions.

DNA sequences were determined either manually by the dideoxy-chain termination method [Sanger et al (1977) Proceedings of the National Academy of Sciences U.S.A. 74, 5463–5467], sequencing directly from pBluescript plasmids, or automatically with the Applied Biosystems Model 373A automatic DNA sequencer, sequencing either directly from these plasmids or from M13 subclones.

Southern and Western hybridizations and other standard manipulations were carried out by well known procedures [see, e.g., Sambrook et al (1989) loc. cit.].

Example 1

Purification of native trehalose synthase

Native trehalose synthase was purified from commercial baker's yeast. The method described by Londesborough & Vuorio [(1991) loc. cit.] for purification of "proteolytically activated TPS/P" was modified as follows:

1. All buffers contained 2 mM $MgCl_2$ and 1 mM EDTA. This increased yields in the early steps and probably helped to decrease proteolysis in the later steps.
2. In the first ammonium sulphate fractionation, the EDTA concentration was increased to 2.5 mM before addition of ammonium sulphate.

3. All buffers were adjusted to between 0.4 and 1 mM PMSF and between 4 and 10 μg pepstatin A/ml by addition, immediately before use, of the appropriate amount of a freshly prepared stock solution containing 1 mg pepstatin A/ml 0.1M PMSF in methanol (called, stock PMSF/pepstatin). When, as in chromatography, buffers were used for several hours, more stock PMSF/pepstatin was added at intervals, but so as not to exceed 1.5% methanol in the buffer, or a fresh lot of buffer was taken into use, because of the short half-life of PMSF in aqueous solution. All columns were equilibrated with at least one bed volume of buffer containing PMSF and pepstatin A immediately before application of enzyme.
4. Experience permitted the enzyme-containing fractions (a total of 17.8 ml) from Heparin-Sepharose to be identified as soon as they were eluted. Stock PMSF/pepstatin (150 μl) and 0.1M EDTA (200 μl) were immediately added to them. Then 7.2 g of powdered ammonium sulphate was slowly added (over 20 min). After 30 min equilibration, the mixture was centrifuged 15 min at 28 000 g. The pellets were packed for 5 min at 28 000 g and expressed buffer removed with a pasteur pipette. The pellets were dissolved to 2.0 ml in HB2M1ED containing 0.8 mM PMSF and 8 μg pepstatin A/ml, centrifuged 5 min at 28 000 g and applied to a 2.6×34 cm column of Sepharose 6B freshly equilibrated with HB2M1ED containing 0.4 mM PMSF and 4 μg pepstatin A/ml. The interval between elution from Heparin-Sepharose and application to Sepharose 6B was 5 h. In the Londesborough & Vuorio [(1991) loc. cit.] procedure, the Heparin-Sepharose eluates were stored at about 3° C., without addition of PMSF or pepstatin A, for 5 days before the second ammonium sulphate fractionation and application to Sepharose 6B.
5. Fractions (3.7 ml) from the Sepharose 6B column were immediately mixed with 20 μl of stock PMSF/pepstatin and then assayed. Again, experience permitted the correct fractions to be pooled, based on activity and A280 measurements without SDS-PAGE analysis, and immediately applied to a 0.7×7 cm column of UDP-Glucuronate-Agarose equilibrated with HB2M1ED containing 0.4 mM PMSF and 4 μg pepstatin A/ml. The enzyme was eluted as described by Londesborough & Vuorio [(1991) loc. cit.] and 10 μl of stock PMSF/pepstatin added to each 1.7 ml fraction. Each fraction was divided into three. Two portions were stored at −70° C. and one at 0° C.

Table 1 summarizes a purification and FIG. 1 shows SDS-PAGE analysis of fractions eluted from UDP-Glucuronate-Agarose. No obvious differences were apparent between enzyme eluted by 0.2M NaCl and that eluted by 10 mMUDPG/0.4M NaCl. The major bands present had molecular masses of 57, 99 and about 130 kDa. Many weaker bands were present between about 130 and 90 kDa. In Western analyses in which these fractions were probed with antisera [described by Londesborough & Vuorio (1991) loc. cit.] against proteolytically activated TPS/P and against isolated short chain (57 kDa) and the 93 kDa fragment of the long chain, the 130 kDa, 99 kDa and most, if not all, of the fainter bands in this region were recognized by the anti-TPS/P and anti-93K sera. This suggests that they are partially degraded long chains. The weak bands at 68 kDa also reacted with the anti-93K serum, but could be removed by chromatography on DEAE-cellulose (see Example 8).

It is not clear why part of the enzyme was eluted already at 0.2M NaCl and part remains bound until washing with 10 mM UDPG in 0.4M NaCl. When #9 was re-run on the same UDP-Glucuronate-Agarose column, 76% of the TPS activity was again eluted by 0.2M NaCl (and 25% by 10 mM UDPG in 0.4M NaCl), so that the reason is not simple over-loading of the column. Possibly, the enzyme that is eluted at 0.2M NaCl is in a different state of aggregation, leading to steric hindrance of its tight binding. However, the ratio of the TPP activity to the TPS activity measured in the presence of F6P varied through the subtle changes in the composition of the trehalose synthase affect both this ratio and the chromatographic behaviour.

These findings disclose that a highly purified trehalose synthase containing a 57 kDa short chain, and about 130 kDa long chain and a 99 kDa polypeptide that is recognised by antiserum to the long chain (anti-93k) possesses both TPS activity activatable by TPS-Activator protein and TPP activity. This novel preparation possesses some unexpected catalytic properties, which are described in more detail in Example 11.

TABLE 1

Purification of native trehalose synthase
The preparation is from 60 g of pressed baker's yeast. TPS activities "Without Activator" were measured as described by Londesborough & Vuorio [(1991) loc. cit.], i.e., in the absence of F6P. Assays "With Activator" were determined similarly but in the presence of a saturating amount of pure TPS activator (similar values were obtained when some fractions were later assayed in the presence of 5 mM F6P instead of TPS activator, and are shown in parentheses).

| Fraction | Volume (ml) | Without Activator | | | With Activator | | |
|---|---|---|---|---|---|---|---|
| | | U/ml | U/mg | Total U | U/ml | U/mg | Total U |
| 1st (NH4)2SO4 Precipitate | 13.4 | 58 | 1.0 | 810 | ND | ND | ND |
| G25 eluate | 22.2 | 30 | 1.1 | 668 | ND | ND | ND |
| Heparin-Sepharose eluate | 18.2 | ND | ND | ND | ≈21 | ≈11 | ≈380 |
| Sepharose 6B eluate | 26 | 1.4 | 5.1 | 36 | 4.7 | 17 | 121 |
| UDP-glucuronate agarose eluates: | | | | | | | |
| at 0.2M NaCl | | | | | | | |
| #9 | 1.7 | 4.6 | 3.1 | — | 11.5(12) | 12 | |
| #10 | 1.7 | ND | ND | ND | 12.2 | 21 | |
| #11 | 1.7 | ND | ND | ND | 6.3 | 23 | 58 |
| #12 | 1.7 | ND | ND | ND | 3.9(3.3) | 22 | |
| at 0.4M NaCl/10 Mm UDPG | | | | | | | |
| #13 | 1.7 | 2.1 | — | — | 5.9(6.2) | 25–30$^a$ | |
| #14 | 1.7 | 3.7 | — | — | 9.3 | 25–30$^a$ | 27 |

TABLE 1-continued

Purification of native trehalose synthase
The preparation is from 60 g of pressed baker's yeast. TPS
activities "Without Activator" were measured as described by
Londesborough & Vuorio [(1991) loc. cit.], i.e., in the absence of
F6P. Assays "With Activator" were determined similarly but in the
presence of a saturating amount of pure TPS activator (similar values
were obtained when some fractions were later assayed in the presence
of 5 mM F6P instead of TPS activator, and are shown in parentheses).

| Fraction | Volume (ml) | Without Activator | | | With Activator | | |
|---|---|---|---|---|---|---|---|
| | | U/ml | U/mg | Total U | U/ml | U/mg | Total U |
| #15 | 1.7 | ND | — | — | 0.8 | — | — |

$^a$based on protein contents estimated from Coomassie blue-stained SDS-PAGE gels.

Example 2

Increased expression by *S. cerevisiae* of the long and short chains of trehalose synthase after consumption of glucose.

Three 500 ml lots of YP/2% glucose in 1 l shake flasks were each inoculated with 1 ml of a suspension of X2180 cells with an $A_{600}$ of 1.0 and shaken at 200 r.p.m. at 30° C. At the times shown in Table 2, the cells were harvested, broken and analyzed as described in General Materials and Methods. The 28 000 g supernatants were stored for a week at −18° C., thawed and re-centrifuged for 20 min at 28 000 g. Portions of 150 μl (each equivalent to 53 mg of fresh yeast) were mixed with 30 μl of anti-TPS/P serum, equilibrated for 30 min at 0° C. and centrifuged for 10 min at 10 000 g. The pellets were washed with 250 μl of HBMED and then dissolved in Laemmli sample buffer and subjected to SDS-PAGE (FIG. 2). Bands at 57, 99 and about 130 kDa were strong in the sample (C) from stationary phase yeast and in the sample (B) harvested immediately after disappearance of glucose from the medium, but were absent or very weak in the sample (A) from yeast growing in the presence of 1.2% glucose.

TABLE 2

Appearance of TPS and TPP activities in X2180 yeast grown on YP/2% glucose.

| | A | B | C |
|---|---|---|---|
| Age (h) | 16.1 | 18.1 | 39.0 |
| Residual glucose (g/100 ml medium) | 1.2 | ≦0.001 | ≦0.001 |
| Fresh yeast mass (mg/ml medium) | 7.6 | 14.8 | 29.5 |
| Trehalose (mg/g dry yeast) | 0.73 | 3.1 | 94 |
| TPS (U/g fresh yeast) | 1.2 | 7.4 | 10.5 |
| TPP (U/g fresh yeast) | 0.29 | 2.2 | 3.0 |
| TPP/TPS (%) | 24 | 30 | 29 |

Control experiments (not shown) showed that pre-immune serum did not precipitate the 57, 99 and about 130 kDa bands, and that using 50 μl of serum instead of 30 μl did not precipitate more of these three bands from the C sample.

These results disclose that the co-ordinate, 7-fold increase in TPS and TPP activities that occurs during less than 2 h when glucose disappears from the medium is accompanied by a large increase in the amounts in yeast of three polypeptides, of mass 57, 99 and about 130 kDa, that are immunoprecipitated by anti-TPS/P serum. These polypeptides are those found in the native trehalose synthase purified in Example 1. Thus, increase in the amount of enzyme protein is a major mechanism by which the capacity of yeast to synthesize trehalose is increased.

Example 3

Determination of the N-terminal amino acid sequences of peptides isolated from the short and long chains of trehalose synthase.

The 57, 86 and 95 kDa polypeptides of the truncated trehalose synthase were separated by SDS-PAGE, digested on nitrocellulose blots and fractionated by HPLC as described by Londesborough & Vuorio [(1991) loc. cit.]. Also, these polypeptides and polypeptides of molecular mass 57, 99 and about 130 kDa immunoprecipitated from yeast extracts as described in Example 2 were separated by SDS-PAGE and digested in the gel with lysylendopeptidase C as described by Kawasaki, H., Emori, Y. and Suzuki, K. (in press). The derived peptides were separated essentially according Kawasaki, H. & Suzuki, K. [(1990) Analytical Biochemistry 186, 264–268] and sequenced in a gas-pulsed liquid phase sequencer as described by Kalkkinen, N. & Tilgmann, C. [(1988) Journal of Protein Chemistry 7, 242–243], the released PTH-amino acids being analyzed by on-line, narrow-bore, reverse-phase HPLC. The sequences are shown in Table 3.

TABLE 3

N-terminal amino acid sequences of peptides isolated from (fragments of) the long and short chains of trehalose synthase.
When two sequences were obtained from the same HPLC peak, they are shown as a and b sequences, where possible according to the
sequences predicted from the genes. Tentative identifications from the amino acid sequencer are shown by the one letter
codes
followed by double queries, and unidentifiable residues are shown by triple queries.

Short chain peptides
Tryptic peprides from blots of the 57 kDa polypeptide from proteolytically activate TPS/P.

| 848 | Tyr—Ile—Ser—Lys |
| | (SEQ ID NO:5) |
| 850 | Asp—Val—Glu—Glu—Tyr—Gln—Tyr—Leu—Arg |
| | (SEQ ID NO:6) |
| 859 | His—Phe—Leu—Ser—Ser—Val—Gln—Arg |
| | (SEQ ID NO:7) |
| 862a | Val—Leu—Asn—Val—Asn—Thr—Leu—Pro—Asn—Gly—Val—Glu—Tyr—Gln— |
| | (SEQ ID NO:8) |

TABLE 3-continued

N-terminal amino acid sequences of peptides isolated from (fragments of) the long and short chains of trehalose synthase. When two sequences were obtained from the same HPLC peak, they are shown as a and b sequences, where possible according to the sequences predicted from the genes. Tentative identifications from the amino acid sequencer are shown by the one letter codes followed by double queries, and unidentifiable residues are shown by triple queries.

| | |
|---|---|
| 862b | Ser—Val—Val—Asn—Glu—Leu—Val—Gly—Arg (SEQ ID NO:9) |
| 863 | Leu—Tyr—Lys |
| 864 | Glu—Thr—Phe—Lys (SEQ ID NO:10) |
| 866 | Leu—Asp—Tyr—Ile—Lys (SEQ ID NO:11) |
| 870 | Ile—Leu—Pro—Val—Arg (SEQ ID NO:12) |

From lysylendopeptidase C digests of immunoprecipitated 57 kDa band

| | |
|---|---|
| 966a | Glu—Val Asn—???—Glu—Lys (SEQ ID NO:13) |
| 966b | Phe—Tyr—Asp—???—L?? (SEQ ID NO:14) |
| 980 | Leu—???—Ala—Met—Glu—Val—Phe—Leu—Asn—Glu—???—Pro—Glu (SEQ ID NO:15) |
| 981 | Tyr—Thr—Ser—Ala—Phe—Trp—Gly—Glu—Asn—Phe—Val—???—Glu—Leu (SEQ ID NO:16) |
| 987 | Phe—Gly—???—Pro—Gly—Leu—Glu—Ile—Pro (SEQ ID NO:17) |

Long chain peptides
Tryptic peptides from blots of the 86 and 93 kDa fragments.

| | |
|---|---|
| 889 | D??—Gly—Ser—Val—Met—Gln (SEQ ID NO:18) |
| 890/891 | Leu—Pro—Gly—Ser—Tyr—Tyr—Lys (SEQ ID NO:19) |
| 892a | Asp—Ala—Ile—Val—Val—Asn—Pro—Met—Asp—Ser—Val—Ala (SEQ ID NO:20) |
| 892b | Met—Ile—Ser—Ile—Leu (SEQ ID NO:21) |

From lysylendopeptidase digest of combined 86 and 93 kDa fragments.

| | |
|---|---|
| 1171 | Arg—Arg—Pro—Gln—Trp—Lys (SEQ ID NO:22) |

From lysylendopeptidase digests of immunoprecipitated 130 kDa band

| | |
|---|---|
| 1047 | Ser—D??—Pro—Gln—Lys (SEQ ID NO:23) |
| 1048 | Phe—Tyr—Arg—Asn—Leu—Asn—Gln—Arg—Phe—Ala—Asp—Ala—Ile—Val—Lys (SEQ ID NO:24) |
| 1054a | Asp—Gly—Ser—Val—Met—Gln—W??—???—Gln—Leu—I?? (SEQ ID NO:25) |
| 1054b | Asn—Ala—Ile—Asn—Thr—Ala—Val—Leu—Glu—Asn—Ile—Ile—Pro—H??—???—H??—Val—Lys (SEQ ID NO:26) |
| 1061 | Leu—Val—Asn—Asp—Glu—Ala—Ser—Glu—Gly—Gln—Val—Lys (SEQ ID NO:27) |
| 1063 | V??—Gln—Asp—Ile—Leu—Leu—Asn—Asn—Thr—Phe—N?? (SEQ ID NO:28) |

From lysylendopeptidase digests of immunoprecipitated 99 kDa band

| | |
|---|---|
| 959 | Asp—Thr—Thr—Gln—Thr—Ala—Pro—Val—T??—Asn—Asn—Val—???—Pro (SEQ ID NO:29) |
| 961 | Asn—Gln—Leu—Asp—Ala—A??—Asn—Tyr—Ala—Glu—Val (SEQ ID NO:30) |
| 1002a | Asn—Leu—Ser—Arg—Trp—Arg—Asn—Tyr—Ala—Glu (SEQ ID NO:31) |
| 1002b | Trp Gln Gly Lys (SEQ ID NO:32) |
| 1043 | Ile—Gln—Leu—Gly—Glu—Ser—Asn—Asp—Asp—D??—L?? (SEQ ID NO:33) |
| 1055 | Gln—Val—Pro—Thr—Ile—Gln—Asp—???—Thr—Asn—Lys (SEQ ID NO:34) |
| 1287 | Ile—Tyr—Xaa—Tyr—Val—Lys (SEQ ID NO:35) |
| 1297a | Asn—Gln—Leu—Thr—Asn—Tyr (SEQ ID NO:36) |
| 1297b | Val—Ala—Leu—Gly (SEQ ID NO:37) |
| 1299 | Asp—Ala—Ile—Val—Val—Asn—Pro—Xaa—Asp—Ser—Val—Ala (SEQ ID NO:38) |

Apart from peptide 966b, all the amino acid sequences determined in the short chain have been located in the TSS1 gene (see Example 4). Putative long chain sequences were obtained from the 86 and 93 kDa fragments (which gave virtually identical peptide maps) and from the about 130 kDa and 99 kDa polypeptides found in immunoprecipitates and presumed to be identical to those in native trehalose synthase. Peptides 890 (from the 86 kDa fragment) and 891 (from the 93 kDa fragment) were identical. Peptide 889 (from the 86 kDa fragment) was identical with the start of peptide 1054a (from the 130 kDa polypeptide). Peptide 892a (from the 86 kDa fragment) was identical with the peptide 1299 (from the 99 kDa polypeptide). These identities support the notion that the 86, 93, 99 and about 130 kDa polypeptides are all derived from a single polypeptide parent, presumably the about 130 kDa polypeptide, but do not exclude the possibility of two very similar parent polypeptides. Eight of these long chain sequences have already been located in the sequenced portion of TSL1 (see Example 5). However, of the ten sequences obtained from the 99 kDa polypeptide, so far only the tetrapeptide, 1002b, has been identified in this gene.

These results disclose the identical amino acid sequences found in the 86 and 93 kDa fragments and in the 86 kDa fragment and complete (130 kDa) long chain, and that the TSS1 and TSL1 genes, described below, actually encode amino acid sequences found in the short and long chains of trehalose synthase.

Example 4

Cloning and sequencing of TSS1.
(a) Preparation and screening of a yeast genomic DNA library.

A genomic library was constructed in the bacteriophage lambda vector, Lambda Zap II, using a partial HaeIII digest of *S. cerevisiae* strain S288C chromosomal DNA, according to Stratagene's Instruction Manual for the Zap-cDNA synthesis kit. The DNA from the ligation reaction was packaged into Giga II Gold packaging extract (Stratagene) according to the manufacturer's instructions (1990). The titer of the recombinants was determined on Luria broth plates containing X-β-galactoside (5-bromo-4-chloro-3-indoyl-β-D-galactopyranoside) as a chromogenic substrate for β-galactosidase and IPTG (isopropyl β-D-thiogalactopyranoside) as an inducer. About 50, 000 recombinants were amplified on large (150 mm) NZY-plates according to Stratagene's instructions. The titre of the resulting library was $5 \times 10^9$ pfu/ml with a total of 150 ml.

Several positive clones were found by screening with anti-TPS/P serum. After three rounds of purification, all clones were positive. They were screened again, now with anti-57K serum, as described in General Methods and Materials.

For further manipulations of DNA, the plasmid part, pBluescript, of the Lambda Zap vector was excised as described in the manual for Predigested Lambda ZapII/EcoR1 Cloning Kit (1989).

(b) Sequencing of TSS1.

A strongly positive clone from the Lambda ZapII library was selected and sequenced manually. The sequence obtained included an open reading frame that encoded a 57 kDa protein, but none of the short chain peptide sequences disclosed in Example 3 was found in the amino acid sequence encoded by this ORF.

Therefore, a second clone was selected, from a group of clones that gave distinct restriction maps compared with the group including the first clone. It also responded less strongly to anti-57K serum, which is why it was not chosen in the first place. It was sequenced using the Exonuclease III/Mung Bean nuclease system for producing series of unidirectional deletions. The deletions were prepared according to Stratagene's manual for the pBluescript Exo/Mung DNA sequencing system. The plasmid was first digested with the restriction enzymes SacI, which leaves a 3' overhang, and BamHI, which leaves a 5' overhang. For filling in possible recessed 3'termini created by Mung Bean nuclease, 2.5 μl of 10X nick-translation buffer, 1 μl of dNTP (a mixture of all four dNTPs, each at 2 mM) and 1 μl (2U) of Klenow fragment were added. The reaction proceeded for 30 min at room temperature and was then stopped with 1 μl of 0.5M EDTA [Sambrook et al (1989) loc. cit.]. The deletion time points were run on a 0.8% low melting agarose gel. The bands were cut out, melted and ligated according to Stratagene's instructions. Portions (5 μl) of each ligation mixture were used to transform XL-1 Blue cells.

The clone proved to encode all the short chain peptide sequences disclosed in Example 3, except the poorly defined pentapeptide, 966b. It is notable that the anti-57K serum alone was an inadequate tool for cloning this gene: the amino acid sequence data disclosed in Example 3 were also essential. Comparison of sequences with the Microgenie Data Bank showed that the gene sequence of the clone was available as an unknown reading frame in the post-translational region of the gene for yeast (*S. cerevisiae*) vacuolar H+-ATPase. The data in the bank contain sequence errors, and have thus been erroneously interpreted as two short unidentified ORFs instead of one long ORF. The complete sequence of the TSS1 gene with 800 bp of promoter and 200 bp of terminator regions is disclosed in FIG. 3. This sequence is SEQ ID NO:1 and the amino acid sequence deduced from its ORF is SEQ ID NO:2.

Example 5

Cloning and sequencing of TSL1.
(a) Preparation and screening of genomic DNA libraries.

The gene TSL1 was first found in the same library as described in Example 4. Screening was done using first anti-TPS/P serum and then anti-93K serum. Later, another library was constructed from a partial EcoR1 digest of chromosomal DNA from *S. cerevisiae*, strain S288C, using the methods described in Example 4.

(b) Sequencing of TSL1.

The anti-93K positive clones from the HaeIII library were partially sequenced manually and then automatically from pBluescript exonuclease deletion series as described in Example 4.

The HaeIII clones did not contain the whole of this long gene, and it was difficult to find the N-terminus from any clone. Therefore, the new EcoR1 library was constructed, screened, first with anti-93 serum and then with nucleotide probes derived from the sequenced parts of TSL1, and sequenced using exonuclease deletions and the automatic sequencer.

The about 65% of the TSL1 sequence that is already known is SEQ ID NO:3. Nucleotides 240–2594 comprise an ORF that encodes the amino acid sequence shown in SEQ ID NO:4 and FIG. 4 and ends in a stop codon (bp 2595–7). This amino acid sequence includes eight of the long chain amino acid sequences disclosed in Example 3. The 5-terminal 35% is being sequenced from clones of the new EcoR1 library.

Example 6

Characterization of TSS1 and TSL1.

The nucleotide sequence of TSS1 encodes a polypeptide of 495 amino acid residues with a calculated molecular mass of 56 kDa. This open reading frame starts with an ATG codon and ends with two TGA codons. The promoter region contains a TATA box and the sequence CCCCGC, which has been implicated in catabolite repression [Nehlin & Ronne, (1990) European Molecular Biology Organization Journal 9, 2891–2898]. This may account for the low expression of trehalose synthase in the presence of glucose disclosed in Example 2.

The first 300 bp of the partial sequence disclosed for TSL1 in FIG. 4 are still uncertain. Therefore the first 20 amino acids indicated are also uncertain. So far, the ORF encodes 785 amino acids, corresponding to a calculated molecular mass of about 89 kDa. This implies that about 1.2 kb are still missing from the 5′-terminal end of the ORF. The 3′-terminus is marked by a TAA codon. Sixty bp downstream from this codon is a possible TATATA transcription termination element [Russo et al (1991) European Molecular Biology Organization Journal 10, 563–571]

FIG. 5 discloses that the entire TSS1 gene exhibits 37% identity at the amino acid level to a 502 amino acid portion of the sequenced part of the TSL1 gene. The genes are obviously closely related.

Most surprisingly, the TSS1 gene is identical to the CIF1 gene that has been recently cloned and sequenced by Gancedo's group [Gonzales et al (1992) Yeast in press]. This group is unaware of the connection with trehalose synthase. This disclosure reveals that special methodology is required to handle mutants containing modified forms of the TSS1 gene, because cif1 mutants have severe defects in sugar metabolism, as discussed in the Detailed Description. It also explains, of course, why no recognisable short chain is present in the Klg 102 mutants, which carry the cif1 mutation (see Example 7). Previously, it has been (tacitly) assumed that failure of cif1 and fdp1 mutants to express TPS activity is the consequence of a lengthy cascade of regulatory effects. The findings disclosed here and in Example 7 show that absence of the short chain of trehalose synthase is the primary defect, from which, in an as yet completely obscure way, the other regulatory defects of these mutants result.

*S. cerevisiae* chromosomes were separated by pulsed field electrophoresis, with pulse times of 60 sec for 15 h and 90 sec for 9 h at 200 volts, as recommended by the instruction manual for the CHEFDR II [BioRad Laboratories, Richmond, Calif.]. Genes were located using digoxigenin-labelled non-radioactive probes, following the instructions in the manual by Boehringer Mannheim. The following probes were used: a 2.1 kb DraI restriction fragment from TSL1 and a 1.9 kb NarI-SmaI restriction fragment of TSS1, where the SmaI site is in the linker between the insert and the vector. TSL1 was located exclusively on Chromosome 16. TSS1 was located exclusively on Chromosome 2, which is where both FDP1 [Van de Poll and Schambert (1977) loc. cit.] and CIF1 [Gonzales et al (1992) loc. cit.] have been located. This disclosure further strengthens the evidence for the identity of TSS1 with CIF1 and FDP1. These and other important restriction sites in TSS1 and TSL1 are shown in FIG. 6.

Example 7

A functional TSS1 gene is required for expression of both TPS and TPP activities.

The *S. cerevisiae* mutant Klg 102, was obtained from Dan Fraenkel (Harvard Medical School) and has the genotype MATα, ura1, leu1, trp5, cif1-102. It was routinely grown on YP/2% galactose or YP/2% glucose, and long term storage was under liquid nitrogen. As reported by others [Navon, G., Shulman, R. G., Yamane, T., Eccleshall, T. R., Lam, K.-B., Baronofsky, J. & Marmur, J. (1979) Biochemistry 18, 4487–4499; Bañuelos, M. & Fraenkel, D. G. (1982) Molecular and Cellular Biology 2, 921–929], this mutant would not grow on YP/2% fructose, though revertants were frequent.

Six individual colonies from each of two substrains, ALKO 2669 and ALKO 2670, that differed in reversion frequency and colony size, were streaked onto YP/2% fructose and YP/2% glucose at 30° C. After 45 h, all 12 streaks were growing on glucose, although slower than the control yeast, X2180, but none showed any growth on fructose. After 4 days, five of the ALKO 2669 streaks showed several large, but isolated colonies on fructose and one ALKO 2670 streak showed several small colonies on fructose. From the glucose plates, three streaks from each substrain were chosen for the smallest number of revertants on the corresponding fructose plate, and used to inoculate 100 ml portions of YPD in 250 ml shake flasks, and grown at 200 r.p.m. and 30° C. Three parallel flasks were inoculated with X2180. A600 and residual glucose in the media were monitored and samples were plated out quantitatively onto YP/2% glucose and YP/2% fructose. The ALKO 2669 cultures grew faster than the ALKO 2670 cultures, and both grew much slower then X2180 (not shown).

At appropriate times the cells were harvested, broken and analyzed as described in the General Materials and Methods. Results are shown in Table 4.

These results show that TPS activity was below the detection level in the Klg 102 samples and less than 0.5% of the value in X2180, which is typical of wild type *S. cerevisiae*. This agrees with previously reported results [Paschoalin, V. M. F., Silva, J. T. & Panek, A. D. (1989) Current Genetics 16, 81–87]. Surprisingly, however, TPP activities were also very low, between ≦1% and 5% of the X2180 values. Even this residual ability to hydrolyse trehalose-6-phosphate is likely to be due to non-specific phosphatases. Paschoalin et al [(1989) loc. cit.] claim that Klg 102 specifically lacks UDPG-linked TPS activity, but that, like the wild-type yeast S288C (which is the haploid form of X2180), it contains an ADPG-linked activity. If this were true, and accepting the conventional view that trehalose synthesis in yeast

TABLE 4

Growth of Klg 102 and X2180 strains on YPD.
The cultures were performed as described in the text. Residual glucose and cell mass are given as, respectively, g/100 ml and mg/ml of growth medium. Phosphoglucoisomerase (PGI) was determined as described in Example 11. PGI, TPS and TPP are given as U/g of wet cells (TPS was determined in the presence of 5 mM F6P). Trehalose is given as mg/g of wet cells. Viability Fru/Glu shows the number of cells able to grow on fructose as a percentage of the number of cells able to grow on glucose at the time of harvesting. Cells from the cultures 2670/1 and 2670/2 were combined for breakage and subsequent analysis.
ND, not determined.

| Strain | Age (h) | Residual Glucose (g %) | CellMass (mg/ml) | PGI (U/g) |
|---|---|---|---|---|
| Klg 102 cultures ||||
| 2669/1 | 24 | ND | 4.3 | 88 |
| 2669/2 | 48 | ≦0.02 | 11.6 | 81 |
| 2669/3 | 114 | none | 10.3 | ND |
| 2670/1 | 110 | | | |
| 2670/2 | 110 | none | 9.7 | 89 |
| 2670/4 | 114 | none | 11.2 | ND |
| X2180 cultures ||||
| 1 | 24 | ND | 19.1 | 93 |
| 2 | 110 | none | 31.7 | 126 |
| 3 | 114 | none | 34.4 | ND |

TABLE 4-continued

| | TPS (U/g) | TPP (U/g) | Trehalose Fru/Glu (mg/g) | Viability (%) |
|---|---|---|---|---|
| | | Klg 102 cultures | | |
| 2669/1 | ≦0.02 | ND | ND | 2.4 |
| 2669/2 | ≦0.03 | 0.034 | ND | ≦1.7 |
| 2669/3 | ND | ≦0.02 | ≦0.22 | ≦1.8 |
| 2670/1 | ≦0.03 | 0.081 | ND | 1.4 |
| 2670/2 | | | | 4.0 |
| 2670/4 | ND | ≦0.02 | ≦0.19 | ≦0.3 |
| | | X2180 cultures | | |
| 1 | 6.3 | 1.7 | ND | ND |
| 2 | 6.3 | 2.3 | ND | ND |
| 3 | ND | 2.9 | 29.3 | ND | proceeds via free trehalose-6-phosphate, Klg 102 should contain significant TPP activity. Our results disclose that this is not the case. Furthermore, when we tested whether wild type yeast (X2180) was able to synthesise [$^{14}$C]-trehalose from [$^{14}$C]-G6P in the presence of UDPG or ADPG, we found significant activity only in the presence of UDPG. The assay systems used by Paschoalin et al [(1989) loc. cit.] have been criticised by Vandercammen et al [(1989) loc. cit.], so we tested the overall reaction directly. Yeast extracts were incubated in 40 mM HEPES pH 6.8 containing 1 mg BSA/ml, 10 mM MgCl$_2$ and 10 mM [U-$^{14}$C]-G6P (736 c.p.m./nmol) in the presence or absence of 5 mM UDPG or 2.5 mM ADPG and presence or absence of 5 mM K phosphate. Reactions were stopped by boiling for 2 min and addition of AG1-X8 (formate) anion exchange resin, as in the TPP assay system described by Londesborough & Vuorio [(1991) loc. cit.]. Results are shown in FIG. 7. Without UDPG or ADPG, radioactivity appeared in the resin supernatants, presumably due to phosphatases active on G6P. UDPG caused a clear increase in this rate in the absence of phosphate and a marked increase in the presence of 5 mM phosphate, which stimulates the TPP activity and inhibits the TPS activity of trehalose synthase. With UDPG and 5 mM phosphate, the increase in rate corresponded, after a lag phase, to 0.94 μmol/min/g of fresh yeast, which is about 50% of the TPP activity of this yeast at 20 mM phosphate. ADPG, however, did not cause any significant increase in the rate of appearance of radioactivity in the resin supernatant, indicating that no ADPG-linked TPS activity was present.

Western blots of the homogenates of Klg 102 and X2180 yeast are shown in FIG. 8. The origin of the bands marked D is not clear: they may be degraded short chain. X2180 shows a strong 57 kDa band, due to the short chain of trehalose synthase and several weak bands at 100 to 130 kDa due to intact and truncated versions of the long chain. In contrast, although the Klg 102 samples showed stronger long chain bands, because more yeast sample was applied to the gel, they showed no trace of a short chain band. Thus, Klg 102 does not contain a recognisable form of the product of the TSS1 gene (it might contain a truncated version lacking the epitopes recognised by our polyclonal antibodies), but contains normal amounts of the TSL1 product. Furthermore, the TSL1 product appears to increase as Klg 102 traverses the diauxic lag (compare e.g. lanes 3 and 2 of FIG. 8), suggesting that expression of the long chain of trehalose synthase in this yeast increases when all glucose is consumed. In wild type yeast, increases in both short and long chains occur concomitant with the increases in TPS and TPP activities when glucose is consumed (Example 2).

These results disclose that the failure of Klg 102 to express immunologically recognisable short chain of trehalose synthase is correlated with the absence of both TPS and TPP activities. This unexpected behaviour, in contradiction of the views of Paschoalin et al [(1989) loc. cit.], indicates that a functional short chain is required to assemble a trehalose synthase with either partial activity.

Example 8

Biochemical evidence that the long chain of trehalose synthase is required for Tpp activity.

Truncated trehalose synthase containing the short (57 kDa) chain and fragments (86 and 93 kDa) of the long chain was prepared according to the method of Londesborough & Vuorio [(1991) loc. cit.] for proteolytically activated TPS/P complex. TPS and TPP activities were assayed as described by Londesborough & Vuorio [(1991) loc. cit.]. [N-ethyl-1-$^{14}$C]-maleimide (ethyl-labelled NEM; 40 mCi/mmol) was NEC-454 from New England Nuclear. N-ethyl-[2,3-$^{14}$C]-maleimide (ring-labelled NEM; 6 mCi/mmol) was CFA 293 from Amersham International. Both were obtained as solutions in n-pentane and the manufacturer's stated specific activities were assumed to be correct. Unlabelled N-ethyl-maleimide (NEM) was E-3876 from Sigma. It was dissolved in 25 mM HEPES pH 7.0 immediately before use and standardized by absorption measurements at 305 nm, assuming an $E^{mM}$ of 0.62.

Treatment of truncated trehalose synthase with 1.9 mM NEM at 24° C. in the presence of about 0.17 mM dithiothreitol (which presumably rapidly consumes about 0.34 mM NEM) caused a rapid and essentially complete (≧98%) loss of TPP activity, but little (≦24%) loss of TPS activity (FIG. 9). This suggested that NEM modified one or more amino acid (presumably cysteine) side chains that are required intact for TPP but not for TPS.

To permit quantitative experiments with low concentrations of labelled NEM, the dithiothreitol in the enzyme preparation was removed by gel-filtration through Pharmacia NAP5 columns equilibrated with 1 mg BSA/ml of 25 mM HEPES pH 7.0 containing 2 mM MgCl$_2$, 1 mM EDTA and 0.2M NaCl. Recoveries of TPS and TPP activities through this gel-filtration were above 85%.

In one experiment, 2.0 μl of ethyl-labelled NEM was mixed with 150 μl of gel-filtered enzyme and incubated at 23° C. Samples (10 μl) taken at various times up to 190 min were mixed with 60 μl of Laemmli sample buffer (the mercaptoethanol in this buffer should destroy residual NEM), boiled for 5 min and subjected to SDS-PAGE. At closely similar times (and also at 23 h) other samples (10 μl) were mixed with 100 μl (for TPS) or 700 μl (for TPP) of 5 mg BSA/ml of 25 mM HEPES pH 7.0 containing 2 mM MgCl$_2$, 1 mM EDTA, 0.2M NaCl and 1 mM dithiothreitol (the dithiothreitol should destroy residual NEM) and assayed for TPS and TPP. The enzyme dilution used for the TPP assay was sufficient that radioactivity from the NEM (about ⅓ of which remains in the resin supernatant) did not interfere with the TPP determinations.

After electrophoresis, the upper (cathode) buffer, containing most of the added radioactivity, was completely removed before disassembling the apparatus. The gel was then fixed, stained and destained as described by Laemmli [(1970) Nature, London 227, 680–685] and dried. An autoradiogram of this gel (FIG. 10) showed that the 93 kDa band (and also BSA) became labelled during the experiment, while the 86 and 57 kDa bands were much more weakly labelled. The Coomassie blue stained bands and adjacent, empty areas (as blanks) were cut out of the dried gel (in later experiments, they were cut from undried gels), broken up and extracted overnight with 1 ml of 5% SDS in preblanked scintillation vials. Then 10 ml of a toluene/Triton X100-based scintillant was added, and the tubes were repeatedly counted using a wide energy window to minimise quench effects. After 10 h constant counting levels were reached. Excess radioactivity was calculated by subtracting a blank value obtained from empty regions of the gel. Results are shown in FIG. 11. In control experiments, in which enzyme was omitted, it was shown that the excess radioactivity found in the 93 and 86 kDa bands did not originate from potential labelling of impurities in the BSA.

FIG. 11 shows that label from NEM enters mainly the 93 kDa fragment of the long chain, with relatively small amounts entering the 86 kDa fragment and the 57 kDa short chain. Also, the amount of label entering the long chain fragments (93+86 kDa) is roughly proportional to the loss of TPP activity, but lags increasingly behind this loss: at 10.5 min 30% of the initial TPP was lost and 0.20 moles of NEM had entered the long chain fragments per mole (150 Kg) of enzyme, whereas at 190 min, 56% of TPP was lost and 0.32 moles of NEM had entered the long chain fragments. Possibly, since trehalose synthase may be an octamer (its native molecular mass is about 800 kDa), reaction of one long chain with NEM can eventually lead to loss of activity associated with the other long chains in the octamer. FIG. 12 collates data from several experiments, using both ring- and ethyl-labelled NEM. Parallel experiments with identical concentrations of ring- and ethyl-labelled NEM suggested that about 25% of the radioactivity from ethyl-labelled NEM originally fixed in the protein was lost during SDS-PAGE processing (some loss is expected in acidic conditions), and the results with ethyl-labelled NEM have been corrected accordingly. Within the limits of accuracy (a specific activity of 30 TPS units/mg was used to calculate the mass of protein and a dimer molecular mass of 150 kDa was assumed for the truncated enzyme) complete loss of TPP reflected incorporation of rather less than 1 mole of NEM into, specifically, the long chain fragments.

Another reagent with high specificity for cysteine, dithiodinitro-benzoate (DTNB) also caused a specific loss of TPP activity: after 10 min treatment with 0.9 mM DTNB over 95% of the TPP was lost and less than 28% of the TPS.

These findings disclose that a proper structure of the long chain is essential for TPP activity, because modification of a single amino acid (presumable cysteine) residue in the long chain eliminates TPP but not TPS activity.

Example 9

An isolated 99 kDa polypeptide from trehalose synthase contains TPP activity.

Because the long and short chains of trehalose synthase could not be separated by usual chromatographic procedures, fractionations were attempted in the presence of a non-ionic detergent. During fractionation with a NaCl gradient on DEAE-cellulose (Whatman DE52) in 1% Triton X100 at pH 8.0, the enzyme was recovered in about 90% yield at 140 mM NaCl. Some minor polypeptides (e.g. the weak 68 kDa polypeptides visible in FIG. 1) were removed, but the main 57, 99 and 130 kDa polypeptides were not resolved. However, the ratio of the 99 and 130 kDa bands changed from about 1.5 to 0.3 across the enzyme peak, while concomitantly the TPP/TPS ratio decreased steadily from 0.54 to 0.42 (data not shown). This suggested that the procedure was partially resolving trehalose synthase molecules enriched in the 99 kDa polypeptide from those containing full length long chains, and that the former had a relatively higher TPP activity.

Because the long chain appears to contain an avid phosphate binding site (see Examples 10 and 12), chromatography on phosphocellulose was attempted. Native trehalose synthase (4.2 TPS units) was transferred above a PM10 membrane in an Amicon cell to 25 mM HEPES pH 7.0 containing 2 mM $MgCl_2$, 1 mM EDTA, 1 mM dithiothreitol and 0.3% Triton X100 (HMED/0.3% T) and applied to a 0.7×4.2 cm column of phosphocellulose (Whatman P11-cellulose) equilibrated with the same buffer. The column was washed with 4 ml of HMED/0.3% T and developed with a linear gradient from zero to 0.6M NaCl in 60 ml of HMED/0.3% T at 5 ml/h. By 0.35M NaCl only traces of TPS had been eluted (≦3% in the first 9 ml and ≦9% spread between 0.15 and 0.35M NaCl). The column was then washed sequentially with (a) 8 ml of 10 mM fructose-6-phosphate in HMED/0.3% T/0.35M NaCl, (b) 6 ml of HMED/0.3% T/0.6M NaCl and (c) 0.2M K phosphate pH 7.0/2 mM $MgCl_2$/1 mM EDTA/1 mM dithiothreitol. No TPS or TPP activity was recovered except in a single 1.5 ml fraction in which the 0.6M NaCl began to elute. This contained 12% of the applied TPP, but ≦0.1% of the applied TPS.

Fractions were examined by SDS-PAGE (FIG. 13) which showed: (1) almost pure short chain eluted at and just before the start of the NaCl gradient in fractions devoid of enzyme activity; (2) traces of short and long chain eluted diffusely at about 0.2 to 0.35M NaCl in fractions containing altogether ≦7% of the applied TPS activity; (3) at least 50% and possibly all of the applied 99 kDa polypeptide eluted at 0.6M NaCl in the fraction containing 12% of the applied TPP activity; and (4) most of the 130 kDa polypeptide remained bound to the column.

These findings disclose that, under special conditions (0.3% Triton X100), the 99 kDa polypeptide can be removed from trehalose synthase and retain TPP, but not TPS, activity. Together with the findings in Example 7, this indicates that, whereas the full length long chain either exhibits no activity or is trehalose synthase unable to attain in vivo a stable, active conformation in the absence of the short chain, once trehalose synthase has been correctly folded, the 99 kDa polypeptide can be removed from the complete enzyme with retention of some TPP activity.

These findings also disclose that when the short chain is separated from the long chain by chromatography in a buffer, in which intact trehalose synthase is stable, it rapidly looses any TPP or TPS activity it possessed when correctly folded in the trehalose synthase.

The findings also indicate that the full-length long chain has extraordinarily high affinity for phosphocellulose, which is consistent with the location of a high affinity phosphate binding site in a terminal portion of this chain as suggested by Examples 10 and 12.

Finally, chromatography on phosphocellulose in the presence of Triton X100 is a convenient method of obtaining the short (57 kDa) chain and 99 kDa polypeptide in sufficient purity to permit, for example, N-terminal amino acid sequencing. No other method has been disclosed, by which the polypeptides of trehalose synthase can be separated, apart from SDS-PAGE. This novel method has several advantages over SDS-PAGE (followed by blotting onto a suitable membrane), including larger scale and freedom from the chemical modifications that frequently block the N-termini of proteins separated by SDS-PAGE.

Example 10

Truncation of the long chain of trehalose synthase by trypsin in vitro dramatically increases TPS activity.

Native trehalose synthase (0.28 TPS units, $\approx 9.4$ µg) was incubated with or without 0.5 µg of trypsin at 30° C. in 250 µl of 13 mM HEPES pH 7.0 containing 1 mM $MgCl_2$, 0.5 mM EDTA, 0.5 mM dithiothreitol, 0.2M NaCl and 0.5 mM benzamidine. Its TPS activity was determined at intervals using standard assay mixtures (containing 5 mM F6P) containing no or 4 mM K phosphate pH 6.8, and samples were prepared for SDS-PAGE analysis immediately before and 48 min after addition of the trypsin.

During the first 48 min the TPS activity measured in the absence of phosphate decreased faster in the presence of trypsin than in its absence. However, in the first 10 min, trypsin caused a 4-fold increase in the activity measured at 4 mM phosphate, and by 48 min the activities with and without phosphate were essentially equal (FIG. 14). By 48 min, the 130 kDa full length long chain had disappeared and been replaced by a doublet of polypeptides at 85 kDa (FIG. 15). In contrast, the short chain (57 kDa) was unchanged and the 99 kDa band was at only slightly decreased in strength.

These findings disclose that limited tryptic digestion of the long chain in vitro has a profound effect on the TPS activity of trehalose synthase at a phosphate concentration typical of cytosol. Thus, the TSL1 gene product is involved in both TPP (see Examples 8 and 9) and TPS activities.

Example 11

Identification of the TPS activator as phosphoglucoisomerase.

TPS activator was transferred to 0.1M Tris/HCl pH 9.0 above a PM10 membrane in an Amicon cell. A 300 µl sample (34 µg) was digested for 20 h at 37° C. by 0.8 µg of lysylendopeptidase C (Wako). Peptides were separated by HPLC and sequenced as described in Example 3. All five sequences obtained and disclosed in Table 5 are identical to sequences found in yeast phosphoglucoisomerase (PGI).

TABLE 5

Peptide sequences from TPS activator.
The PGI sequences are from Tekamp-Olson, P., Najarian, R. & Burke, R. L. (1988) Gene 73, 153–161.

| | TPS-Activator Peptide | PGI Residues |
|---|---|---|
| TA1156 | TFTNYDGSK | 51–59 |
| | (SEQ ID NO:39) | |
| TA1158 | TGNDPSHIAK | 241–251 |
| | (SEQ ID NO:40) | |
| TA1159 | IYESQGK | 24–30 |
| | (SEQ ID NO:41) | |
| TA1160 | AEGATGGLVPHK | 456–467 |
| | (SEQ ID NO:42) | |
| TA1161 | LATELPAXSK | 11–19 |

TABLE 5-continued

Peptide sequences from TPS activator.
The PGI sequences are from Tekamp-Olson, P., Najarian, R. & Burke, R. L. (1988) Gene 73, 153–161.

| TPS-Activator Peptide | PGI Residues |
|---|---|
| (SEQ ID NO:43) | |

The PGI activity of a sample of TPS activator that had been stored for several months at 0° C. was measured in 50 mM HEPES/KOH pH 7.0, 5 mM $MgCl_2$, 5 mM F6P and 0.4 mg/ml NADP. A specific activity of 190 U/mg was found.

These findings disclose that TPS activator from S. cerevisiae is identical to PGI. Example 12 discloses that F6P is a powerful activator of the TPS activity of native, but not of truncated, trehalose synthase. Because the assay mixtures for TPS contain G6P, it is clear that TPS activator functions by producing the activatory F6P from the substrate G6P. Previous investigations [Londesborough & Vuorio (1991) loc. cit.] had to use crude preparations of native trehalose synthase because pure native trehalose synthase was not available. Although the effectiveness of TPS activator preparations was reported to vary between different enzyme preparations, under certain circumstances data were obtained that suggested TPS activator might interact stoichiometrically with native trehalose synthase [Londesborough & Vuorio (1991) loc. cit.]. The present findings show that this suggestion was completely incorrect. The findings also imply that kinetic data in the literature is confused, because some preparations of so-called "trehalose-6-phosphate synthase" will have contained PGI whereas some may not. With the former preparations, the activator F6P will have been generated from the substrate G6P, but the amount so generated will have depended upon the details of the experimental procedure used.

Example 12

The different kinetic behaviours of native and truncated trehalose synthase.

Truncated trehalose synthase was prepared as described by Londesborough & Vuorio [(1991) loc. cit.] and contained the 57 kDa short chain and 86 and 93 kDa fragments of the long chain. Native trehalose synthase was prepared as in Example 1 and contained the 57 kDa short chain, a 130 kDa long chain and also the 99 kDa polypeptide. Kinetic assays were done at 30° C. as described in General Methods and Materials.

(a) The TPS Partial Activity.

The TPS activity of native enzyme was much more sensitive to inhibition by phosphate than was that of the truncated enzyme (Table 6).

TABLE 6

Inhibition of the TPS activities of native and truncated enzyme by phosphate at 5 Mm F6P.
The effect of adding K phosphate pH 6.8 to standard assay mixtures (10 mM G6P, 5 mM UDPG and 5 mm F6P) is shown. For each enzyme, the activity without phosphate is set at 100%.

| Added Phosphate | Native Enzyme | Truncated Enzyme |
|---|---|---|
| None | 100% | 100% |
| 1.3 mM | 69% | 94% |
| 4.0 mM | 14% | 83% |

The results in Table 6 underestimate the difference between the phosphate responses of native and truncated enzyme, because F6P partially reverses the phosphate inhibition of native enzyme (see below) but has virtually no effect on truncated enzyme. Table 7 shows the effect of shifting from the salt conditions of the standard assay (40 mM HEPES/KOH pH 6.8, 10 mM MgCl$_2$) to conditions closer to those of yeast cytosol. In the absence of F6P, the shift caused 67% inhibition of native enyzme (from 43% to 14% of the standard activity) but only 10% inhibition of truncated enzyme (from 96% to 86%).

TABLE 7

Effect on the TPS activity of native and truncated enzyme of shifting to more physiological salt conditions.
For measurements at "physiological conditions", 1.3 mM K phosphate and 0.1M KCl were added to the standard assay mixtures and the MgCl$_2$ was decreased from 10 to 2.5 mM.

|  | Standard Cond. | | Physiological Cond. | |
| --- | --- | --- | --- | --- |
|  | (5 mM F6P) | No F6P | 5 mM F6P | No F6P |
| Native | 100% | 43% | 72% | 14% |
| Truncated | 100% | 96% | 90% | 86% |

These results disclose the insensitivity of the TPS activity of truncated trehalose synthase to physiological phosphate concentrations and the presence or absence of F6P at a concentration well above the normal value in yeast cytosol (between 0.1 and 1 mM; Lagunas, R. & Gancedo, C. (1983) European Journal of Biochemistry 137, 479–483).

FIG. 16 illustrates the F6P-dependence of the TPS activity of native enzyme at different phosphate concentrations. Double-reciprocal plots indicate that at 1.3 mM phosphate, and perhaps at 4 mM phosphate, sufficiently high concentrations of F6P completely overcome the inhibition by phosphate. With no added phosphate, F6P caused a maximum activation of 2.5-fold, with a $K_{\frac{1}{2}}$ of 60 μM. At 1.3 mM phosphate, the maximum activation was at least 20-fold, and the $K_{\frac{1}{2}}$ was 1.4 mM F6P. The slopes of these double-reciprocal plots varied linearly with the square of the phosphate concentration, suggesting that two phosphate binding sites are involved. At 4 mM phosphate, which is still within the probable range of phosphate concentrations in yeast cytosol [Lagunas & Gancedo (1983) loc. cit], inhibition was so severe that even 10 mM F6P permitted only 40% of the activity observed under standard conditions. Thus, expression of a truncated trehalose synthase in yeast would be expected to cause a large increase in the intracellular specific activity of the enzyme.

Fructose-1-phosphate, fructose-1,6-bisphosphate, fructose-2,6-bisphosphate and glucose-1-phosphate were tested at sub-optimal F6P concentrations (1 mM F6P at 1.3 mM phosphate). None caused activation at 5 or 2.5 mM concentrations; instead inhibitions of about 25% occurred, probably due to competition with G6P and F6P.

(b) The TPP Partial Activity.

At phosphate concentrations equal to or less than 1 mM, the progress curves of TPP reactions catalysed by truncated trehalose synthase accelerated markedly over at least the first 10 min of reaction. This did not happen with native enzyme. For the initial rates of reaction, native enzyme was activated by smaller phosphate concentrations than was truncated enzyme (FIG. 17). For truncated enzyme, double-reciprocal plots of the activation ($v_A$ = the rate with phosphate, $v_{Pi}$, minus the rate without phosphate, $v_o$) were linear when $1/v_A$ was plotted against 1/[phosphate], with a $K_{\frac{1}{2}}$ of 3 mM phosphate. For native enzyme these plots were non-linear, and linear plots resulted when 1/[phosphate]$^2$ was used (FIG. 18). This, again, suggests that native enzyme has two strong phosphate binding sites, one of which is lost in the truncated enzyme. For native enzyme, half maximal activation was obtained at 0.6 mM phosphate.

In the absence of phosphate, F6P did not affect the TPP activity of native enzyme. At sub-optimal phosphate concentrations, 5 mM F6P caused modest (20 to 30%) inhibitions of the TPP activity of both native and truncated enzymes, and at saturating phosphate concentrations, smaller inhibitions (10 to 15%) were observed (data not shown).

These findings disclose a profound sensitivity of the TPS activity of native trehalose synthase to physiological phosphate and F6P concentrations that is lost by truncation of the long chain from 130 kDa to about 90 kDa. The effects of truncation are less marked on the TPP activities, both enzymes being activated by physiological phosphate concentrations, and neither showing a strong response to F6P. The data suggest that native enzyme has two strong phosphate binding sites, one of which is located in the region of the long chain removed by truncation. The finding that full length long chain could not be recovered from phosphocellulose, disclosed in Example 9 supports this conclusion.

Example 13

The complete sequence of the TSL1 gene.

The EcoRI genomic library of *S. cerevisiae*, strain S288C, described in Example 5 has been screened with anti-93K serum and positive clones further screened using nucleotide probes. Several positive clones have been obtained with an 8.2 kb insert that must contain the missing about 1.2 kb at the 5'terminus of the ORF and also the upstream flanking sequence. A plasmid pALK751 (also known as pOV12), containing this insert has been deposited on Feb. 18, 1992 with the Deutsch Sammlung von Mikroorganismen (DSM), Gesellschaft fürBiotechnologtische, Forschung mbH, Grisebachstr.8, 3400 Göttingen, Germany and has been given the accession number DSM 6928. The insert may be sequenced by standard methods, such as those described in Examples 4 and 5. Smaller fragments may be made with appropriate restriction enzymes. These fragments and the original inserts can be sequenced (a) by using primers designed from the 5'-terminal portion of SEQ ID NO:3 and (b) by subcloning endonuclease deletion series back into pBluescript Sk– and use of the Applied Biosystems automatic DNA sequencer (see General Materials and Methods and Examples 4 and 5).

Example 14

Transformation of yeast.

(1) Assembly of complete genes and truncated versions of TSL1.

DNA molecules containing the complete ORFs and required flanking regions of TSS1 and TSL1 may be assembled by (1) ligating pieces of DNA containing separate parts of the genes that have been isolated in different clones from the respective libraries, and (2) trimming off unwanted parts of the 5'- and 3'-flanking regions. The methods to be used are routine to a person skilled in the art and involve (1) excision of unwanted DNA pieces by judicious use of restriction enzymes, the choice depending upon the nucleotide sequences of the vectors to be used, the sequences disclosed in SEQ ID NO:1 and SEQ ID NO:3 and the sequence of the remaining 5'-portion of TSL1, and (2) ligation of the desired pieces, preceded, when necessary, by appropriate filling-in reactions or construction of suitable linkers.

For TSL1, truncated versions of the ORF may be made that encode truncated versions of the long chain of trehalose synthase confering F6P-independent activity that is relatively insensitive to inhibition by phosphate, as disclosed in Examples 10 and 12. The truncation site may be located by isolating the 85 kDa doublet of polypeptides generated by in Vitro limited digested with trypsin (Example 10) either by SDS-PAGE or by chromatography, e.g, on phosphocellulose in the presence of Triton X 100 as described in Example 9. The about 45 kDa polypeptide representing the other piece of the long chain may also be isolated. It is foreseen that this, shorter polypeptide may be degraded by trypsin under the conditions used in Example 10. For this reason, it may be useful to perform limited digestion with other enzymes (e.g., lysylendopeptidase C) and with trypsin and these enzymes in the presence of phosphate and F6P, because findings disclosed in Examples 9, 10 and 12 suggest that the shorter polypeptide removed by trypsin contains phosphate and F6P binding sites, so that these compounds may protect this region of the polypeptide from proteolytic attack. It is possible that conditions are found in which truncation by limited proteolysis yields only two polypeptides from the long chain, whereby determination of the N-terminal sequence of one or the other will define the truncation site exactly. Alternatively, determination of internal peptide sequences together with the size of the truncated polypeptide will determine the position within the accuracy (about $\pm 1.5$ kDa$\approx$15 amino acids) of SDS-PAGE. The TSL1 gene may be cut at or near this point using standard procedures including restriction enzymes at suitable restriction sites. The truncated gene may then be ligated to its own promoter and/or terminator (depending on which were removed during the truncation) or inserted into expression cassettes (see below) containing other yeast operators and terminators, as described below. The ability of the truncated gene to express a polypeptide that can associate in vivo with the short chain of trehalose synthase may be a critical function of the position of the truncation. Therefore, several versions may be tested. If necessary, limited endonuclease treatments to generate a mixture of molecules covering a range of truncation sites may be used, and the products ligated into expression vectors and screened for the production in yeast of trehalose synthase with the desired properties (F6P-independence and insensitivity to phosphate).

Finally, because the sequenced two-thirds of the TSL1 gene only contains 8 of the 21 peptides sequenced in Example 3 from the various forms of the long chain (the 130 kDa intact chain and the 86, 93 and 99 kDa truncated versions), it is possible that two closely related versions of the long chain may exist, encoded by two closely related genes. Therefore, if the complete sequence of TSL1 does not reveal the missing peptides, a search may be made for a related gene (TSL2), using hybridization at low stringency to probes derived from TSL1 or nucleotide probes designed from some of the missing peptides.

(2) Disruption mutants.

The TSS1 and TSL1 genes may be disrupted to confirm that they are the structural genes of trehalose synthase. This will also give additional evidence concerning the possible existence of a TSL2 gene, mentioned above. In addition, the phenotypes of these disruption mutants will indicate the physiological consequences of deficiency of these genes. The phenotype after disruption of TSS1 would be expected to resemble the fdp1 and cis1 phenotypes (see Example 2). The one-step gene disruption method [Rothstein, R. J. (1983) Methods in Enzymology 101, 202–211] may be used. A set of "disruption cassettes" specifically designed for this purpose has been described [Berben et al (1991) Yeast 7, 475–477) and cassettes based on these well known principles but tailored to a particular problem can be constructed by a person skilled in the art.

(3) Strategies for transformation.

Laboratory strains of S. cerevisiae bearing auxotropic markers such as his3, leu2, lys 2, trp1 and ura3 may be transformed with versions of TSS1 and TSL1 in which the natural promoters and terminators are intact or have been replaced by (stronger and regulatable) promoters and terminators from other yeast genes. For example, PGKI [pMA91; Mellor et al (1983) Gene 24, 1–14], ADC1 [pAAH5; Ammerer (1983) Methods in Enzymology 101, 192–201] and MEL1 [pALK35–37, pALK41, etc., Suominen, P. L. (1988) Doctoral dissertation, University of Helsinki] systems have been used to increase the expression levels of genes in S. cerevisiae and other yeast. The MEL1 system has the advantage that the expression can be regulated, being repressed by glucose and induced by galactose. Standard vectors are available [episomal and integrating and centromere yeast plasmids are reviewed by Rose & Broach (1990) Methods in Enzymology 185, 234–279 and Stearns, T., Ma, H & Botstein, D. (1990) Methods in Enzymology 185, 280–291] that incorporate auxotrophic markers such as HIS3, LEU2, TRP1 and URA3, which can be used to select the transformants. Vectors based on these principles, but suited to a particular task can be constructed by a person familiar with the art.

The basic strategy is to leave the yeast with an intact version of its natural TSS1 and TSL1 genes and introduce, either on episomes or integrated into a yeast chromosome, extra copies of the genes. These may be under control of their own promoters, or of stronger promoters and promoters that can be regulated, for example by adding substances such as galactose to the growth medium or by changing the temperature. The use of such promoters has been described [see, e.g., Mylin et al (1990) Methods in Enzymology 185, 297–308; Sledziewski et al (1990) Methods in Enzymology 185, 351–366]. This strategy avoids problems that can be foreseen if all copies of one or both genes are put under tight control (such as the defects in sugar catabolism expected if TSS1 is not properly expressed; see Example 7.) Transformed yeast bearing additional copies of TSS1 and TSL1 with their natural promoters may accumulate enough trehalose to exhibit the desired improvement in stability. They may also cycle enough glucose units through trehalose during fermentative conditions to generate an ATPase that accelerates fermentation and increases the yield of ethanol on glucose. In another aspect of the invention, copies of the TSS1 and TSL1 ORFs will be inserted into expression vectors equipped with powerful promoters (that may be regulatable) to cause still larger increases in trehalose. This aspect of the present invention will be particularly useful for the production of trehalose.

Transforming yeast with both TSS1 and TSL1 may be achieved in several ways. The most obvious procedure is to use two auxotrophic markers and introduce first one and then the other gene. Another method is to construct a YIp containing URA3 and a modified version of TSL1 with a stronger promoter but still containing a region of homology upstream of this promoter. After directed integration of this plasmid to the chromosomal ura3 site and selection of URA+ transformants, mutants in which the URA3 has again been excised (with a frequency of about $1 \times 10^{-4}$) can be selected by growth on media containing 5-fluoroorotic acid [see Stearns et al (1990) loc. cit.]. Some of the selected cells would contain a new version of the gene, with the stronger promoter and can again be transformed, this time with a modified TSS1 gene. The resultant transformants will contain one copy of TSL1 driven by the new promoter, and two copies of TSS1, one of which is still under the control of its natural promoter. Thirdly, a YIp containing both TSS1 and TSL1 could be used to introduce the two genes in a single step.

Various methods to transform industrial, polyploid yeast, which lack auxotrophic markers have been described in the literature. Earlier methods have been reviewed by Knowles, J. K. C. & Tubb, R. S. [(1987) E. B. C. symposium on brewer's yeast, Helsinki, 1986. Monograph XII 169-185] and include the use of marker genes that confer resistance to antibiotics, methylglyoxal, copper, cinnamic acid and other compounds. These markers facilitate selection of transformants. Some of the marker genes are themselves of yeast origin, and so are preferred for acceptability reasons. When suitable modifications of TSS1 and TSL1 have been identified in laboratory yeast, they may be transferred to industrial yeast using these procedures or others described in the literature, such as co-transformation with pALK2 and pALK7 [Suominen, P. I. (1988) loc. cit.]. These plasmids contain a readily selectable MEL1 marker gene on a 2 μ-based plasmid that can readily be cured, thus facilitating sequential transformation with more than one gene if it is not practicable to introduce the modified TSS1 and TSL1 genes in one step using this co-transformation procedure.

Example 15

Transformation of crop plants.

Methods for the transformation of higher plants, including crop plants of economic importance, have been described [Goodman et al (1987) Science 236, 48-54; Weising et al, (1988) Annual Review of Genetics 22, 421-477; Glasser & Fraley (1989) Science 244, 1293-1299] and laboratory manuals setting out standard procedures are available such as the Plant Molecular Biology Manual [ed Gelvin & Schnilperoort (1988) Kluwer Academic Press]. Of particular utility is the use of tissue specific promoters from the genes of proteins that are expressed in a highly tissue-specific manner [see, e.g., Higgins (1984) Annual Review of Plant Physioloogy 35, 191 et seq; Shotwell and Larkins (1989) in The Biochemistry of Plants 15, 297 et seq]. The use of such promoters will allow the expression of trehalose synthase in (a) specifically the frost- and drought-sensitive tissues of plants so that they may be protected from these and equivalent stresses without diverting carbohydrate metabolism in the major storage tissues, or alternatively (b) precisely in the edible tissues. The purpose of this second alternative is to cause the accumulation of trehalose in products such as the fruit of tomatoes, in order to increase the shelf-life of these products. The expression of non-plant genes, with higher A+T contents than are commonly found in plant genes can generally be improved by changing the codons to increase the G+C content, and in particular to avoid regions of overall high A+T content [Perlak et al (1991) loc. cit.]. It is foreseen that such modifications will be beneficial in the case of the genes TSS1 and TSL1, which have A+T-rich regions. Selection systems are available for use in the transformation of higher plants, including plasmids comprising the gene (hpt) for hygromycin phosphotransferase [Dale & Ow (1991) Proceedings of the National Academy of Sciences, USA 88, 10558-10562]. These and similar methods familiar to persons skilled in the art will be used, first to introduce various modifications of TSS1 and TSL1 into *Arabidopsis thaliana,* and then to transfer the most successful modifications to plants of economic importance.

One example of how one would transform a crop plant (dicots and some monocots) is via a Ti plasmid. A large fragment of the Ti plasmid encompassing both the T-DNA and vir regions is first cloned into the common bacterial plasmid pBR322. One or both of the genes, TSS1 and TSL1, are then cloned into a nonessential region of the T-DNA and introduced into *Agrobacterium tumefaciens* carrying an intact Ti plasmid. The plants are then infected with these bacteria and the gene products of the vir region on the intact Ti plasmid mobilize the recombinant T-DNA, and the recombinant T-DNA integrates into the plant geome. One or both of the trehalose synthase genes can be introduced into the plant in this manner, by either inserting both genes into the same plasmid or on separate plasmids. The infection with the Agrobacterium containing the hybrid plasmid may also take place in leaf disks and callus cultures.

We claim:

1. An isolated and purified DNA fragment consisting of sequence which encodes a TSS1 polypeptide characterized as having the amino acid sequence of SEQ ID No: 2 or functionally equivalent mutations of SEQ ID No: 2.

2. The DNA sequence of claim 1 which consisting of the DNA sequence of SEQ ID No: 1 or functionally equivalent mutations thereof.

3. A vector which comprises the DNA sequence of claim 1.

4. A yeast host cell transformed with the vector of claim 3.

5. An isolated and purified DNA fragment consisting of sequence which encodes for an active polypeptide that is a component of trehalose synthase and is characterized as having either the amino acid sequence of SEQ ID No: 4 or functionally equivalent mutations of SEQ ID No: 4.

6. The DNA sequence of claim 5, which consisting of the DNA sequence of SEQ ID No: 3 or functionally equivalent mutations thereof.

7. A vector which comprises the DNA sequence of claim 5.

8. A yeast host cell transformed with the vector of claim 7.

9. A vector which comprises a DNA sequence which encodes for the amino acid sequence of SEQ ID No. 2 or a functionally equivalent mutation of SEQ ID No: 2 and a DNA sequence which encodes for an active polypeptide characterized as having the amino acid sequence of SEQ ID No: 4 or functionally equivalent mutations Of SEQ ID NO: 4.

10. A yeast host cell transformed with the vector of claim 9.

11. The isolated and purified DNA sequence of the gene TSL1 and mutations functionally equivalent to TSL1, which gene is contained in the plasmid pALK751 and comprises at least the DNA sequence SEQ ID No: 3.

12. A yeast transformed with a vector comprising the TSL1 gene of claim 11 or mutations functionally equivalent to that gene.

13. An yeast which has been transformed with at least one gene selected from the group consisting of TSS1 and TSL1.

14. The yeast of claim 13 which is *Saccharomyces cerevisiae*.

15. The yeast of claim 13, wherein the yeast exhibits increased trehalose content as compared to the untransformed yeast when grown under the same conditions.

16. The yeast of claim 13, wherein said yeast produces a higher yield of ethanol from carbohydrate than does the untransformed yeast.

17. The yeast of claim 13 wherein said yeast is more resistant to heat, cold and water deprivation than is the untransformed yeast.

18. A process for producing trehalose by fermenting a yeast which has been transformed with at least one gene selected from the group consisting of TSS1 and TSL1 such that the transformed yeast produces trehalose.

19. The process according to claim 18, wherein the yeast is *Saccharomyces cerevisiae*.

20. A yeast transformed with part of the isolated and purified DNA sequence shown in SEQ ID NO:3 which yeast expresses a truncated form of the long chain of trehalose synthase lacking up to 600 amino acids from one end, wherein the truncated form expressed results in production of a trehalose synthase that is less sensitive to inhibition by phosphate than is the native trehalose synthase of *Saccharomyces cerevisiae*.

21. A transformed yeast according to claim 20, wherein the long chain of trehalose synthase lacks between 300 and 450 amino acids from one end.

22. A transformed yeast according to claim 20, wherein, as a result of the transformation the yeast expresses a trehalose synthase that is less activated by fructose-6-phosphate than is the native synthase of *Saccharomyces cerevisiae*.

23. A portion of the TSL1 gene encoding a truncated form of the long chain of trehalose synthase, which comprises an amino acid sequence lacking up to 600 amino acids from one end.

24. A plasmid containing TSL1 designated pALK751 DSM accession no. 6928.

* * * * *

SEQUENCE LISTING ( 1 ) GENERAL INFORMATION:

( i i i ) NUMBER OF SEQUENCES: 43

( 2 ) INFORMATION FOR SEQ ID NO:1:

( i ) SEQUENCE CHARACTERISTICS:
        ( A ) LENGTH: 2484 base pairs
        ( B ) TYPE: Nucleotide
        ( C ) STRANDEDNESS: Doublestranded
        ( D ) TOPOLOGY: Linear ( i i ) MOLECULE TYPE: Genomic DNA ( i i i ) HYPOTHETICAL: no ( i v ) ANTI-SENSE: no ( v i ) ORIGINAL SOURCE:
    ( A ) ORGANISM: Saccharomyces cerevisiae
    ( B ) STRAIN: S288C
    ( E ) HAPLOTYPE: Haploid ( v i i ) IMMEDIATE SOURCE:
    ( A ) LIBRARY: Genomic
    ( B ) CLONE: 20

( v i i i ) POSITION IN GENOME:
    ( A ) CHROMOSOME/SEGMENT: 2R ( x i ) SEQUENCE DESCRIPTION: SEQ ID NO:1:

| | | | | |
|---|---|---|---|---|
| TTTTTAAACG | TATATAGATG | TCTACATGTG | TGTTTTTGTT | TTTTTACGTA | 50 |
| CGTATACCCC | ACTATATATG | CATAATCCGT | AATTGAAAAA | AAAAAAAGTA | 100 |
| AAGATCAAGG | AACACATCAC | CCTGGGCACA | TCAAGCGTGA | GGAATGCCGT | 150 |
| CCAACTGGTG | GAGACGCTTG | ATTTGCTCTT | TTTGTTCCTG | GGTCCAACCC | 200 |
| GGTCTCGAAG | AACATCAGCA | CCACGCCCGC | AACGACAAAG | AACATTGCAA | 250 |
| TACACTTGCA | TATGTGAGCA | TAGTCGAGCG | GTCCGTTCTG | TGGTTGATGC | 300 |
| TGTTGTTCTT | TCTTCTGTTT | GTCAGGGGTG | ATAGCCATAT | CTTCGTGCTC | 350 |
| TTGTTGCGAT | TGTTCTGTTC | CATCTGCACC | AGAACAAAGA | ACAAAAGAAC | 400 |
| AAGGAACAAA | GTCCAAGCAC | GTCAGCGCTG | TTTATAAGGG | GATTGACGAG | 450 |
| GGATCGGGCC | TAGAGTGCCA | GCGCGCCAGG | GAGAGGGAGC | CCCCTGGGCC | 500 |
| CTCATCCGCA | GGCTGATAGG | GGTCACCCCG | CTGGGCAGGT | CAGGGCAGGG | 550 |
| GCTCTCAGGG | GGGCGCCATG | GACAAACTGC | ACTGAGGTTC | TAAGACACAT | 600 |
| GTATTATTGT | GAGTATGTAT | ATATAGAGAG | AGATTAAGGC | GTACACGCGT | 650 |
| GGTTGGTAGA | GATTGATTAA | CTTGGTAGTC | TTATCTTGTC | AATTGAGTTT | 700 |
| CTGTCAGTTT | CCTTCTTGAA | CAAGCACGCA | GCTAAGTAAG | CAACAAAGCA | 750 |
| GGCTAACAAA | CTAGGTACTC | ACATACAGAC | TTATTAAGAC | ATAGAACTAT | 800 |
| GACTACGGAT | AACGCTAAGG | CGCAACTGAC | CTCGTCTTCA | GGGGGTAACA | 850 |
| TTATTGTGGT | GTCCAACAGG | CTTCCCGTGA | CAATCACTAA | AAACAGCAGT | 900 |
| ACGGGACAGT | ACGAGTACGC | AATGTCGTCC | GGAGGGCTGG | TCACGGCGTT | 950 |
| GGAAGGGTTG | AAGAAGACGT | ACACTTTCAA | GTGGTTCGGA | TGGCCTGGGC | 1000 |
| TAGAGATTCC | TGACGATGAG | AAGGATCAGG | TGAGGAAGGA | CTTGCTGGAA | 1050 |
| AAGTTTAATG | CCGTACCCAT | CTTCCTGAGC | GATGAAATCG | CAGACTTACA | 1100 |
| CTACAACGGG | TTCAGTAATT | CTATTCTATG | GCCGTTATTC | CATTACCATC | 1150 |
| CTGGTGAGAT | CAATTTCGAC | GAGAATGCGT | GGTTCGGATA | CAACGAGGCA | 1200 |
| AACCAGACGT | TCACCAACGA | GATTGCTAAG | ACTATGAACC | ATAACGATTT | 1250 |
| AATCTGGGTG | CATGATTACC | ATTTGATGTT | GGTTCCGGAA | ATGTTGAGAG | 1300 |
| TCAAGATTCA | CGAGAAGCAA | CTGCAAAACG | TTAAGGTCGG | GTGGTTCCTG | 1350 |
| CACACACCAT | TCCCTTCGAG | TGAAATTTAC | AGAATCTTAC | CTGTCAGACA | 1400 |
| AGAGATTTTG | AAGGGTGTTT | TGAGTTGTGA | TTAGTCGGG | TTCCACACAT | 1450 |
| ACGATTATGC | AAGACATTTC | TTGTCTTCCG | TGCAAAGAGT | GCTTAACGTG | 1500 |
| AACACATTGC | CTAATGGGGT | GGAATACCAG | GGCAGATTCG | TTAACGTAGG | 1550 |
| GGCCTTCCCT | ATCGGTATCG | ACGTGGACAA | GTTCACCGAT | GGGTTGAAAA | 1600 |
| AGGAATCCGT | ACAAAAGAGA | ATCCAACAAT | TGAAGGAAAC | TTTCAAGGGC | 1650 |

```
TGCAAGATCA TAGTTGGTGT CGACAGGCTG GATTACATCA AAGGTGTGCC 1700

TCAGAAGTTG CACGCCATGG AAGTGTTTCT GAACGAGCAT CCAGAATGGA 1750

GGGGCAAGGT TGTTCTGGTA CAGGTTGCAG TGCCAAGTCG TGGAGATGTG 1800

GAAGAGTACC AATATTTAAG ATCTGTGGTC AATGAGTTGG TCGGTAGAAT 1850

CAACGGTCAG TTCGGTACTG TGGAATTCGT CCCCATCCAT TTCATGCACA 1900

AGTCTATACC ATTTGAAGAG CTGATTTCGT TATATGCTGT GAGCGATGTT 1950

TGTTTGGTCT CGTCCACCCG TGATGGTATG AACTTGGTTT CCTACGAATA 2000

TATTGCTTGC CAAGAAGAAA AGAAAGGTTC CTTAATCCTG AGTGAGTTCA 2050

CAGGTGCCGC ACAATCCTTG AATGGTGCTA TTATTGTAAA TCCTTGGAAC 2100

ACCGATGATC TTTCTGATGC CATCAACGAG GCCTTGACTT TGCCCGATGT 2150

AAAGAAAGAA GTTAACTGGG AAAAACTTTA CAAATACATC TCTAAATACA 2200

CTTCTGCCTT CTGGGGTGAA AATTTCGTCC ATGAATTATA CAGTACATCA 2250

TCAAGCTCAA CAAGCTCCTC TGCCACCAAA AACTGATGAA CCCGATGCAA 2300

ATGAGACGAT CGTCTATTCC TGGTCCGGTT TTCTCTGCCC TCTCTTCTAT 2350

TCACTTTTTT TATACTTTAT ATAAAATTAT ATAAATGACA TAACTGAAAC 2400

GCCACACGTC CTCTCCTATT CGTTAACGCC TGTCTGTAGC GCTGTTACTG 2450

AAGCTGCGCA AGTAGTTTTT TCACCGTATA GGCC         2484
```

(2) INFORMATION FOR SEQ ID NO:2:

(i) SEQUENCE CHARACTERISTICS:
        (A) LENGTH: 495 amino acids
        (B) TYPE: amino acid
        (D) TOPOLOGY: linear (ii) MOLECULE TYPE: Polypeptide (iii) HYPOTHETICAL: Yes (xi) SEQUENCE DESCRIPTION:SEQ ID NO:2:

```
Met Thr Thr Asp Asn Ala Lys Ala Gln Leu Thr Ser Ser Ser Gly
                  5                  10                 15

Gly Asn Ile Ile Val Val Ser Asn Arg Leu Pro Val Thr Ile Thr
                 20                  25                 30

Lys Asn Ser Ser Thr Gly Gln Tyr Glu Tyr Ala Met Ser Ser Gly
                 35                  40                 45

Gly Leu Val Thr Ala Leu Glu Gly Leu Lys Lys Thr Tyr Thr Phe
                 50                  55                 60

Lys Trp Phe Gly Trp Pro Gly Leu Glu Ile Pro Asp Asp Glu Lys
                 65                  70                 75

Asp Gln Val Arg Lys Asp Leu Leu Glu Lys Phe Asn Ala Val Pro
                 80                  85                 90

Ile Phe Leu Ser Asp Glu Ile Ala Asp Leu His Tyr Asn Gly Phe
                 95                 100                105

Ser Asn Ser Ile Leu Trp Pro Leu Phe His Tyr His Pro Gly Glu
                110                 115                120

Ile Asn Phe Asp Glu Asn Ala Trp Phe Gly Tyr Asn Glu Ala Asn
                125                 130                135

Gln Thr Phe Thr Asn Glu Ile Ala Lys Thr Met Asn His Asn Asp
                140                 145                150

Leu Ile Trp Val His Asp Tyr His Leu Met Leu Val Pro Glu Met
                155                 160                165
```

-continued

| | | | | | | | | | | | | | |
|---|---|---|---|---|---|---|---|---|---|---|---|---|---|
| Leu | Arg | Val | Lys | Ile<br>170 | His | Glu | Lys | Gln | Leu<br>175 | Gln | Asn | Val | Lys | Val<br>180 |
| Gly | Trp | Phe | Leu | His<br>185 | Thr | Pro | Phe | Pro | Ser<br>190 | Ser | Glu | Ile | Tyr | Arg<br>195 |
| Ile | Leu | Pro | Val | Arg<br>200 | Gln | Glu | Ile | Leu | Lys<br>205 | Gly | Val | Leu | Ser | Cys<br>210 |
| Asp | Leu | Val | Gly | Phe<br>215 | His | Thr | Tyr | Asp | Tyr<br>220 | Ala | Arg | His | Phe | Leu<br>225 |
| Ser | Ser | Val | Gln | Arg<br>230 | Val | Leu | Asn | Val | Asn<br>235 | Thr | Leu | Pro | Asn | Gly<br>240 |
| Val | Glu | Tyr | Gln | Gly<br>245 | Arg | Phe | Val | Asn | Val<br>250 | Gly | Ala | Phe | Pro | Ile<br>255 |
| Gly | Ile | Asp | Val | Asp<br>260 | Lys | Phe | Thr | Asp | Gly<br>265 | Leu | Lys | Lys | Glu | Ser<br>270 |
| Val | Gln | Lys | Arg | Ile<br>275 | Gln | Gln | Leu | Lys | Glu<br>280 | Thr | Phe | Lys | Gly | Cys<br>285 |
| Lys | Ile | Ile | Val | Gly<br>290 | Val | Asp | Arg | Leu | Asp<br>295 | Tyr | Ile | Lys | Gly | Val<br>300 |
| Pro | Gln | Lys | Leu | His<br>305 | Ala | Met | Glu | Val | Phe<br>310 | Leu | Asn | Glu | His | Pro<br>315 |
| Glu | Trp | Arg | Gly | Lys<br>320 | Val | Val | Leu | Val | Gln<br>325 | Val | Ala | Val | Pro | Ser<br>330 |
| Arg | Gly | Asp | Val | Glu<br>335 | Glu | Tyr | Gln | Tyr | Leu<br>340 | Arg | Ser | Val | Val | Asn<br>345 |
| Glu | Leu | Val | Gly | Arg<br>350 | Ile | Asn | Gly | Gln | Phe<br>355 | Gly | Thr | Val | Glu | Phe<br>360 |
| Val | Pro | Ile | His | Phe<br>365 | Met | His | Lys | Ser | Ile<br>370 | Pro | Phe | Glu | Glu | Leu<br>375 |
| Ile | Ser | Leu | Tyr | Ala<br>380 | Val | Ser | Asp | Val | Cys<br>385 | Leu | Val | Ser | Ser | Thr<br>390 |
| Arg | Asp | Gly | Met | Asn<br>395 | Leu | Val | Ser | Tyr | Glu<br>400 | Tyr | Ile | Ala | Cys | Gln<br>405 |
| Glu | Glu | Lys | Lys | Gly<br>410 | Ser | Leu | Ile | Leu | Ser<br>415 | Glu | Phe | Thr | Gly | Ala<br>420 |
| Ala | Gln | Ser | Leu | Asn<br>425 | Gly | Ala | Ile | Ile | Val<br>430 | Asn | Pro | Trp | Asn | Thr<br>435 |
| Asp | Asp | Leu | Ser | Asp<br>440 | Ala | Ile | Asn | Glu | Ala<br>445 | Leu | Thr | Leu | Pro | Asp<br>450 |
| Val | Lys | Lys | Glu | Val<br>455 | Asn | Trp | Glu | Lys | Leu<br>460 | Tyr | Lys | Tyr | Ile | Ser<br>465 |
| Lys | Tyr | Thr | Ser | Ala<br>470 | Phe | Trp | Gly | Glu | Asn<br>475 | Phe | Val | His | Glu | Leu<br>480 |
| Tyr | Ser | Thr | Ser | Ser<br>485 | Ser | Ser | Thr | Ser | Ser<br>490 | Ser | Ala | Thr | Lys | Asn<br>495 |

( 2 ) INFORMATION FOR SEQ ID NO:3:

( i ) SEQUENCE CHARACTERISTICS:
        ( A ) LENGTH: 3000 base pairs
        ( B ) TYPE: Nucleotide
        ( C ) STRANDEDNESS: Doublestranded
        ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:

(A) ORGANISM: Saccharomyces cerevisiae
(B) STRAIN: S288C
(E) HAPLOTYPE: Haploid (vii) IMMEDIATE SOURCE:
(A) LIBRARY: Genomic
(B) CLONE: 6

(vii) POSITION IN GENOME:
(A) CHROMOSOME/SEGMENT: 16

(xi) SEQUENCE DESCRIPTION: SEQ ID NO:3:

| | | | | | |
|---|---|---|---|---|---|
| CCTCCTCTGG | ATCTTCTGGG | TCTTCTGCGC | CACCTTCCAT | TAAAAGGATT | 50 |
| ACGCCCCACT | TGACTGCGTC | TGCTGCAAAA | CAGCGTCCCT | TATTGGCTAA | 100 |
| ACAGCCTTCT | AATCTGAAAT | ATTCGGAGTT | AGCAGATATT | TCGTCGAGTG | 150 |
| AGACGTCTTC | GCAGCATAAT | GAGTCGGACC | CGGATGATCT | AACTACTGCC | 200 |
| CTGACGAGGA | TATGTTTCTG | ATTAGGAATT | GATGACGCGA | GAGGACTACA | 250 |
| AGGTTCAAAG | TTCGGCGCTA | TTCATAAATC | AACTAAGAAA | TATGCGCTGT | 300 |
| TAAGGTCATC | TCAGGAGCTG | TTTAGCCGTC | TTCCATGGTC | GATCGTTCCC | 350 |
| TCTATCAAAG | GTAATGGCGC | CATGAAGAAC | GCCATAAACA | CTGCAGTCTT | 400 |
| GGAGAATATC | ATTCCGCACC | GTCATGTTAA | GTGGGTCGGT | ACCGTCGGAA | 450 |
| TCCCAACGGA | TGAGATTCCG | GAAAATATCC | TTGCGAACAT | CTCTGACTCT | 500 |
| TTAAAAGACA | AGTACGACTC | CTATCCTGTC | CTTACGGACG | ACGACACCTT | 550 |
| CAAAGCCGCA | TACAAAAACT | ACTGTAAACA | AATCTTGTGG | CCTACGCTGC | 600 |
| ATTACCAGAT | TCCAGACAAT | CCGAACTCGA | AGGCTTTTGA | AGATCACTCT | 650 |
| TGGAAGTTCT | ATAGAAACTT | AAACCAAAGG | TTTGCGGACG | CGATCGTTAA | 700 |
| AATCTATAAG | AAAGGTGACA | CCATCTGGAT | TCATGATTAC | CATTTAATGC | 750 |
| TGGTTCCGCA | GATGGTGAGA | GACGTCTTGC | CTTTTGCCAA | AATAGGATTT | 800 |
| ACCTTACATG | TCTCGTTCCC | CAGTAGTGAA | GTGTTTAGGT | GTCTGGCTCA | 850 |
| GCGTGAGAAG | ATCTTAGAAG | GCTTGACCGG | TGCAGACTTT | GTCGGCTTCC | 900 |
| AGACGAGGGA | GTATGCAAGA | CATTTCTTAC | AGACGTCTAA | CCGTCTGCTA | 950 |
| ATGGCGGACG | TGGTACATGA | TGAAGAGCTA | AGTATAACG | GCAGAGTCGT | 1000 |
| TTCTGTGAGG | TTCACCCCAG | TTGGTATCGA | CGCCTTTGAT | TTGCAATCGC | 1050 |
| AATTGAAGGA | TGGAAGTGTC | ATGCAATGGC | GTCAATTGAT | TCGTGAAAGA | 1100 |
| TGGCAAGGGA | AAAAACTAAT | TGTGTGTCGT | GATCAATTCG | ATAGAATTAG | 1150 |
| AGGTATTCAC | AAGAAATTGT | TGGCTTATGA | AAAATTCTTG | GTCGAAAATC | 1200 |
| CGGAATACGT | GGAAAAATCG | ACTTTAATTC | AAATCTGTAT | TGGAAGCAGT | 1250 |
| AAGGATGTAG | AACTGGAGCG | CCAGATCATG | ATTGTCGTGG | ATAGAATCAA | 1300 |
| CTCGCTATCC | ACCAATATTA | GTATTTCTCA | ACCTGTGGTG | TTTTTGCATC | 1350 |
| AAGATCTAGA | TTTTTCTCAG | TATTTAGCTT | TGAGTTCAGA | GGCAGATTTG | 1400 |
| TTCGTAGTCA | GCTCTCTAAG | GGAAGGTATG | AACTTGACAT | GTCACGAATT | 1450 |
| TATCGTTTGT | TCTGAGGACA | AAAATGCTCC | CCTACTGTTG | TCAGAATTTA | 1500 |
| CTGGTAGTGC | ATCTTTATTG | AATGATGGCG | CTATAATAAT | TAACCCATGG | 1550 |
| GATACCAAGA | ACTTCTCACA | AGCCATTCTC | AAGGGGTTGG | AGATGCCATT | 1600 |
| CGATAAGAGA | AGGCCACAGT | GGAAGAAATT | GATGAAAGAC | ATTATCAACA | 1650 |
| ACGACTCTAC | AAACTGGATC | AAGACTTCTT | TACAAGATAT | TCATATTTCG | 1700 |
| TGGCAATTCA | ATCAAGAAGG | TTCCAAGATC | TTCAAATTGA | ATACAAAAAC | 1750 |

| | | | | |
|---|---|---|---|---|
| ACTGATGGAA | GATTACCAGT | CATCTAAAAA | GCGTATGTTT | GTTTTCAACA | 1800 |
| TTGCTGAACC | ACCTTCATCG | AGAATGATTT | CCATACTGAA | TGACATGACT | 1850 |
| TCTAAGGGCA | ATATCGTTTA | CATCATGAAC | TCATTTCCAA | AGCCCATTCT | 1900 |
| GGAAAATCTT | TACAGTCGTG | TGCAAAACAT | TGGGTTGATT | GCCGAGAATG | 1950 |
| GTGCATACGT | TAGTCTGAAC | GGTGTATGGT | ACAACATTGT | TGATCAAGTC | 2000 |
| GATTGGCGTA | ACGATGTAGC | CAAAATTCTC | GAGGACAAAG | TGGAGAGATT | 2050 |
| ACCTGGCTCG | TACTACAAGA | TAAATGAGTC | CATGATCAAG | TTCCACACTG | 2100 |
| AAAATGCGGA | AGATCAAGAT | CGTGTAGCTA | GTGTTATCGG | TGATGCCATC | 2150 |
| ACACATATCA | ATACTGTTTT | TGACCACAGA | GGTATTCATG | CCTACGTTTA | 2200 |
| CAAAAACGTT | GTTTCCGTAC | AACAAGTGGG | ACTTTCCTTA | TCGGCAGCTC | 2250 |
| AATTTCTTTT | CAGATTCTAT | AATTCTGCTT | CGGATCCACT | GGATACGAGT | 2300 |
| TCCGGCCAAA | TCACAAATAT | TCAGACACCA | TCTCAACAAA | ATCCTTCAGA | 2350 |
| TCAAGAACAA | CAACCTCCAG | CCTCTCCCAC | TGTGTCGATG | AACCATATTG | 2400 |
| ATTTCGCATG | TGTCTCTGGT | TCATCGTCTC | CTGTGCTTGA | ACCATTGTTC | 2450 |
| AAATTGGTCA | ATGATGAAGC | AAGTGAAGGG | CAAGTAAAAG | CCGGACACGC | 2500 |
| CATTGTTTAT | GGTGATGCTA | CTTCTACTTA | TGCCAAAGAA | CATGTAAATG | 2550 |
| GGTTAAACGA | ACTTTTCACG | ATCATTTCAA | GAATCATTGA | AGATTAAATT | 2600 |
| TTACCATTTT | AAAATTTTAA | TGTTCTTGGG | TATGAACTTT | TATTTTCAAC | 2650 |
| TGCTTATTAT | ATATCAATTC | TATAAATTTT | TTCTTCTCT | CTAACGACCA | 2700 |
| ATTATAAAAT | TCATCCTCTT | ATTTATTACA | GCATCTTATA | CATTATGTAT | 2750 |
| ATGGGTAGCT | ATTATTCATT | TTTGCTTCGT | AAGGACTTTT | TTTGTCAACT | 2800 |
| TTTTCATCCT | AAGCGGCTAA | AAGTGATTGG | AGAGGAATGT | CCAGGCGACC | 2850 |
| AATGATAAAA | ACGCTTTCTC | TTGGAACAAG | AAATAGGAGC | AATTGACAGT | 2900 |
| TGTCGATGAA | CAGCGAAAAT | AGTAAGATAA | CCTTCAAGCC | CAATATTCTA | 2950 |
| ATTAAAGGCG | TTTATATATT | TGTACTTTAT | GGTATGTGCA | TATGTATTGT | 3000 |

( 2 ) INFORMATION FOR SEQ ID NO:4:

( i ) SEQUENCE CHARACTERISTICS:
        ( A ) LENGTH: 785 amino acids
        ( B ) TYPE: Amino acid
        ( D ) TOPOLOGY: Linear ( i i ) MOLECULE TYPE: Polypeptide ( i i i ) HYPOTHETICAL: Yes?

( v ) FRAGMENT TYPE: C-terminal ( x i ) SEQUENCE DESCRIPTION: SEQ ID NO:4:

| Arg | Gly | Leu | Gln | Gly | Ser | Lys | Phe | Gly | Ala | Ile | His | Lys | Ser | Thr |
|---|---|---|---|---|---|---|---|---|---|---|---|---|---|---|
| | | | | 5 | | | | | 10 | | | | | 15 |

| Lys | Lys | Tyr | Ala | Leu | Leu | Arg | Ser | Ser | Gln | Glu | Leu | Phe | Ser | Arg |
|---|---|---|---|---|---|---|---|---|---|---|---|---|---|---|
| | | | | 20 | | | | | 25 | | | | | 30 |

| Leu | Pro | Trp | Ser | Ile | Val | Pro | Ser | Ile | Lys | Gly | Asn | Gly | Ala | Met |
|---|---|---|---|---|---|---|---|---|---|---|---|---|---|---|
| | | | | 35 | | | | | 40 | | | | | 45 |

| Lys | Asn | Ala | Ile | Asn | Thr | Ala | Val | Leu | Glu | Asn | Ile | Ile | Pro | His |
|---|---|---|---|---|---|---|---|---|---|---|---|---|---|---|
| | | | | 50 | | | | | 55 | | | | | 60 |

| Arg | His | Val | Lys | Trp | Val | Gly | Thr | Val | Gly | Ile | Pro | Thr | Asp | Glu |
|---|---|---|---|---|---|---|---|---|---|---|---|---|---|---|
| | | | | 65 | | | | | 70 | | | | | 75 |

-continued

| | | | | | | | | | | | | |
|---|---|---|---|---|---|---|---|---|---|---|---|---|
| Ile | Pro | Glu | Asn | Ile | Leu | Ala | Asn | Ile | Ser | Asp | Ser | Leu | Lys | Asp |
| | | | | 80 | | | | 85 | | | | | | 90 |
| Lys | Tyr | Asp | Ser | Tyr | Pro | Val | Leu | Thr | Asp | Asp | Thr | Phe | Lys |
| | | | | 95 | | | | 100 | | | | | 105 |
| Ala | Ala | Tyr | Lys | Asn | Tyr | Cys | Lys | Gln | Ile | Leu | Trp | Pro | Thr | Leu |
| | | | | 110 | | | | 115 | | | | | | 120 |
| His | Tyr | Gln | Ile | Pro | Asp | Asn | Pro | Asn | Ser | Lys | Ala | Phe | Glu | Asp |
| | | | | 125 | | | | 130 | | | | | | 135 |
| His | Ser | Trp | Lys | Phe | Tyr | Arg | Asn | Leu | Asn | Gln | Arg | Phe | Ala | Asp |
| | | | | 140 | | | | 145 | | | | | | 150 |
| Ala | Ile | Val | Lys | Ile | Tyr | Lys | Lys | Gly | Asp | Thr | Ile | Trp | Ile | His |
| | | | | 155 | | | | 160 | | | | | | 165 |
| Asp | Tyr | His | Leu | Met | Leu | Val | Pro | Gln | Met | Val | Arg | Asp | Val | Leu |
| | | | | 170 | | | | 175 | | | | | | 180 |
| Pro | Phe | Ala | Lys | Ile | Gly | Phe | Thr | Leu | His | Val | Ser | Phe | Pro | Ser |
| | | | | 185 | | | | 190 | | | | | | 195 |
| Ser | Glu | Val | Phe | Arg | Cys | Leu | Ala | Gln | Arg | Glu | Lys | Ile | Leu | Glu |
| | | | | 200 | | | | 205 | | | | | | 210 |
| Gly | Leu | Thr | Gly | Ala | Asp | Phe | Val | Gly | Phe | Gln | Thr | Arg | Glu | Tyr |
| | | | | 215 | | | | 220 | | | | | | 225 |
| Ala | Arg | His | Phe | Leu | Gln | Thr | Ser | Asn | Arg | Leu | Leu | Met | Ala | Asp |
| | | | | 230 | | | | 235 | | | | | | 240 |
| Val | Val | His | Asp | Glu | Glu | Leu | Lys | Tyr | Asn | Gly | Arg | Val | Val | Ser |
| | | | | 245 | | | | 250 | | | | | | 255 |
| Val | Arg | Phe | Thr | Pro | Val | Gly | Ile | Asp | Ala | Phe | Asp | Leu | Gln | Ser |
| | | | | 260 | | | | 265 | | | | | | 270 |
| Gln | Leu | Lys | Asp | Gly | Ser | Val | Met | Gln | Trp | Arg | Gln | Leu | Ile | Arg |
| | | | | 275 | | | | 280 | | | | | | 285 |
| Glu | Arg | Trp | Gln | Gly | Lys | Lys | Leu | Ile | Val | Cys | Arg | Asp | Gln | Phe |
| | | | | 290 | | | | 295 | | | | | | 300 |
| Asp | Arg | Ile | Arg | Gly | Ile | His | Lys | Lys | Leu | Leu | Ala | Tyr | Glu | Lys |
| | | | | 305 | | | | 310 | | | | | | 315 |
| Phe | Leu | Val | Glu | Asn | Pro | Glu | Tyr | Val | Glu | Lys | Ser | Thr | Leu | Ile |
| | | | | 320 | | | | 325 | | | | | | 330 |
| Gln | Ile | Cys | Ile | Gly | Ser | Ser | Lys | Asp | Val | Glu | Leu | Glu | Arg | Gln |
| | | | | 335 | | | | 340 | | | | | | 345 |
| Ile | Met | Ile | Val | Val | Asp | Arg | Ile | Asn | Ser | Leu | Ser | Thr | Asn | Ile |
| | | | | 350 | | | | 355 | | | | | | 360 |
| Ser | Ile | Ser | Gln | Pro | Val | Val | Phe | Leu | His | Gln | Asp | Leu | Asp | Phe |
| | | | | 365 | | | | 370 | | | | | | 375 |
| Ser | Gln | Tyr | Leu | Ala | Leu | Ser | Ser | Glu | Ala | Asp | Leu | Phe | Val | Val |
| | | | | 380 | | | | 385 | | | | | | 390 |
| Ser | Ser | Leu | Arg | Glu | Gly | Met | Asn | Leu | Thr | Cys | His | Glu | Phe | Ile |
| | | | | 395 | | | | 400 | | | | | | 405 |
| Val | Cys | Ser | Glu | Asp | Lys | Asn | Ala | Pro | Leu | Leu | Leu | Ser | Glu | Phe |
| | | | | 410 | | | | 415 | | | | | | 420 |
| Thr | Gly | Ser | Ala | Ser | Leu | Leu | Asn | Asp | Gly | Ala | Ile | Ile | Ile | Asn |
| | | | | 425 | | | | 430 | | | | | | 435 |
| Pro | Trp | Asp | Thr | Lys | Asn | Phe | Ser | Gln | Ala | Ile | Leu | Lys | Gly | Leu |
| | | | | 440 | | | | 445 | | | | | | 450 |
| Glu | Met | Pro | Phe | Asp | Lys | Arg | Arg | Pro | Gln | Trp | Lys | Lys | Leu | Met |
| | | | | 455 | | | | 460 | | | | | | 465 |
| Lys | Asp | Ile | Ile | Asn | Asn | Asp | Ser | Thr | Asn | Trp | Ile | Lys | Thr | Ser |
| | | | | 470 | | | | 475 | | | | | | 480 |
| Leu | Gln | Asp | Ile | His | Ile | Ser | Trp | Gln | Phe | Asn | Gln | Glu | Gly | Ser |

```
                               485                        490                        495
Lys  Ile  Phe  Lys  Leu  Asn  Thr  Lys  Thr  Leu  Met  Glu  Asp  Tyr  Gln
                    500                      505                        510
Ser  Ser  Lys  Lys  Arg  Met  Phe  Val  Phe  Asn  Ile  Ala  Glu  Pro  Pro
                    515                      520                        525
Ser  Ser  Arg  Met  Ile  Ser  Ile  Leu  Asn  Asp  Met  Thr  Ser  Lys  Gly
                    530                      535                        540
Asn  Ile  Val  Tyr  Ile  Met  Asn  Ser  Phe  Pro  Lys  Pro  Ile  Leu  Glu
                    545                      550                        555
Asn  Leu  Tyr  Ser  Arg  Val  Gln  Asn  Ile  Gly  Leu  Ile  Ala  Glu  Asn
                    560                      565                        570
Gly  Ala  Tyr  Val  Ser  Leu  Asn  Gly  Val  Trp  Tyr  Asn  Ile  Val  Asp
                    575                      580                        585
Gln  Val  Asp  Trp  Arg  Asn  Asp  Val  Ala  Lys  Ile  Leu  Glu  Asp  Lys
                    590                      595                        600
Val  Glu  Arg  Leu  Pro  Gly  Ser  Tyr  Tyr  Lys  Ile  Asn  Glu  Ser  Met
                    605                      610                        615
Ile  Lys  Phe  His  Thr  Glu  Asn  Ala  Glu  Asp  Gln  Asp  Arg  Val  Ala
                    620                      625                        630
Ser  Val  Ile  Gly  Asp  Ala  Ile  Thr  His  Ile  Asn  Thr  Val  Phe  Asp
                    635                      640                        645
His  Arg  Gly  Ile  His  Ala  Tyr  Val  Tyr  Lys  Asn  Val  Val  Ser  Val
                    650                      655                        660
Gln  Gln  Val  Gly  Leu  Ser  Leu  Ser  Ala  Ala  Gln  Phe  Leu  Phe  Arg
                    665                      670                        675
Phe  Tyr  Asn  Ser  Ala  Ser  Asp  Pro  Leu  Asp  Thr  Ser  Ser  Gly  Gln
                    680                      685                        690
Ile  Thr  Asn  Ile  Gln  Thr  Pro  Ser  Gln  Gln  Asn  Pro  Ser  Asp  Gln
                    695                      700                        705
Glu  Gln  Gln  Pro  Pro  Ala  Ser  Pro  Thr  Val  Ser  Met  Asn  His  Ile
                    710                      715                        720
Asp  Phe  Ala  Cys  Val  Ser  Gly  Ser  Ser  Pro  Val  Leu  Glu  Pro
                    725                      730                        735
Leu  Phe  Lys  Leu  Val  Asn  Asp  Glu  Ala  Ser  Glu  Gly  Gln  Val  Lys
                    740                      745                        750
Ala  Gly  His  Ala  Ile  Val  Tyr  Gly  Asp  Ala  Thr  Ser  Thr  Tyr  Ala
                    755                      760                        765
Lys  Glu  His  Val  Asn  Gly  Leu  Asn  Glu  Leu  Phe  Thr  Ile  Ile  Ser
                    770                      775                        780
Arg  Ile  Ile  Glu  Asp
                    785
```

( 2 ) INFORMATION FOR SEQ ID NO:5:

( i ) SEQUENCE CHARACTERISTICS:
        ( A ) LENGTH: 4 amino acids
        ( B ) TYPE: Amino acid
        ( D ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION: SEQ ID NO:5:

Tyr  Ile  Ser  Lys ( 2 ) INFORMATION FOR SEQ ID NO:6:

( i ) SEQUENCE CHARACTERISTICS:
    ( A ) LENGTH: 9 amino acids
    ( B ) TYPE: Amino acid
    ( D ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION: SEQ ID NO:6:

Asp Val Glu Glu Tyr Gln Tyr Leu Arg
            5

( 2 ) INFORMATION FOR SEQ ID NO:7:

( i ) SEQUENCE CHARACTERISTICS:
        ( A ) LENGTH: 8 amino acids
        ( B ) TYPE: Amino acid
        ( D ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION: SEQ ID NO:7:

His Phe Leu Ser Ser Val Gln Arg
            5

( 2 ) INFORMATION FOR SEQ ID NO:8:

( i ) SEQUENCE CHARACTERISTICS:
        ( A ) LENGTH: 14 amino acids
        ( B ) TYPE: Amino acid
        ( D ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION: SEQ ID NO:8:

Val Leu Asn Val Asn Thr Leu Pro Asn Gly Val Glu Tyr Gln
            5                           10

( 2 ) INFORMATION FOR SEQ ID NO:9:

( i ) SEQUENCE CHARACTERISTICS:
        ( A ) LENGTH: 9 amino acids
        ( B ) TYPE: Amino acid
        ( D ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION: SEQ ID NO:9:

Ser Val Val Asn Glu Leu Val Gly Arg
            5

( 2 ) INFORMATION FOR SEQ ID NO:10:

( i ) SEQUENCE CHARACTERISTICS:
        ( A ) LENGTH: 4
        ( B ) TYPE: Amino acid
        ( D ) TOPOLOGY: Linear (i i) MOLECULE TYPE: Peptide (i i i) HYPOTHETICAL: No (i v) FRAGMENT TYPE: N-terminal (v) SEQUENCE DESCRIPTION: SEQ ID NO:10:

Glu Thr Phe Lys (2) INFORMATION FOR SEQ ID NO:11:

(i) SEQUENCE CHARACTERISTICS:
        (A) LENGTH: 5 amino acids
        (B) TYPE: Amino acid
        (D) TOPOLOGY: Linear (i i) MOLECULE TYPE: Peptide (i i i) HYPOTHETICAL: No (i v) FRAGMENT TYPE: N-terminal (v) SEQUENCE DESCRIPTION: SEQ ID NO:11:

Leu Asp Tyr Ile Lys
            5

(2) INFORMATION FOR SEQ ID NO:12:

(i) SEQUENCE CHARACTERISTICS:
        (A) LENGTH: 5 amino acids
        (B) TYPE: Amino acid
        (D) TOPOLOGY: Linear (i i) MOLECULE TYPE: Peptide (i i i) HYPOTHETICAL: No (i v) FRAGMENT TYPE: N-terminal (v) SEQUENCE DESCRIPTION: SEQ ID NO:12:

Ile Leu Pro Val Arg
            5

(2) INFORMATION FOR SEQ ID NO:13:

(i) SEQUENCE CHARACTERISTICS:
        (A) LENGTH: 6 amino acids
        (B) TYPE: Amino acid
        (D) TOPOLOGY: Linear (i i) MOLECULE TYPE: Peptide (i i i) HYPOTHETICAL: No (i v) FRAGMENT TYPE: N-terminal (v) SEQUENCE DESCRIPTION: SEQ ID NO:13:

Glu Val Asn Xaa Glu Lys
                5

(2) INFORMATION FOR SEQ ID NO:14:

(i) SEQUENCE CHARACTERISTICS:
        (A) LENGTH: 5 amino acids
        (B) TYPE: Amino acid
        (D) TOPOLOGY: Linear (i i) MOLECULE TYPE: Peptide (i i i) HYPOTHETICAL: No (i v) FRAGMENT TYPE: N-terminal (v) SEQUENCE DESCRIPTION: SEQ ID NO:14:

Phe Tyr Asp Xaa Xaa
      5

( 2 ) INFORMATION FOR SEQ ID NO:15:

( i ) SEQUENCE CHARACTERISTICS:
        ( A ) LENGTH: 13 amino acids
        ( B ) TYPE: Amino acid
        ( D ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION: SEQ ID NO:15:

Leu Xaa Ala Met Glu Val Phe Leu Asn Glu Xaa Pro Glu
              5                           10

( 2 ) INFORMATION FOR SEQ ID NO:16:

( i ) SEQUENCE CHARACTERISTICS:
        ( A ) LENGTH: 14 amino acids
        ( B ) TYPE: Amino acid
        ( D ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION: SEQ ID NO:16:

Tyr Thr Ser Ala Phe Trp Gly Glu Asn Phe Val Xaa Glu Leu
              5                           10

( 2 ) INFORMATION FOR SEQ ID NO:17:

( i ) SEQUENCE CHARACTERISTICS:
        ( A ) LENGTH: 9 amino acids
        ( B ) TYPE: Amino acid
        ( D ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION: SEQ ID NO:17:

Phe Gly Xaa Pro Gly Leu Glu Ile Pro
              5

( 2 ) INFORMATION FOR SEQ ID NO:18:

( i ) SEQUENCE CHARACTERISTICS:
        ( A ) LENGTH: 6 amino acids
        ( B ) TYPE: Amino acid
        ( D ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION: SEQ ID NO:18:

Xaa Gly Ser Val Met Gln
              5

( 2 ) INFORMATION FOR SEQ ID NO:19:

( i ) SEQUENCE CHARACTERISTICS:
  ( A ) LENGTH: 7 amino acids
  ( B ) TYPE: Amino acid
  ( D ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION: SEQ ID NO:19:

Leu Pro Gly Ser Tyr Tyr Lys
                  5

( 2 ) INFORMATION FOR SEQ ID NO:20:

( i ) SEQUENCE CHARACTERISTICS:
    ( A ) LENGTH: 12 amino acids
    ( B ) TYPE: Amino acid
    ( D ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION: SEQ ID NO:20:

Asp Ala Ile Val Val Asn Pro Met Asp Ser Val Ala
                  5                   10

( 2 ) INFORMATION FOR SEQ ID NO:21:

( i ) SEQUENCE CHARACTERISTICS:
    ( A ) LENGTH: 5 amino acids
    ( B ) TYPE: Amino acid
    ( D ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION: SEQ ID NO:21:

Met Ile Ser Ile Leu
              5

( 2 ) INFORMATION FOR SEQ ID NO:22:

( i ) SEQUENCE CHARACTERISTICS:
    ( A ) LENGTH: 6 amino acids
    ( B ) TYPE: Amino acid
    ( D ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION: SEQ ID NO:22:

Arg Arg Pro Gln Trp Lys
                  5

( 2 ) INFORMATION FOR SEQ ID NO:23:

( i ) SEQUENCE CHARACTERISTICS:
    ( A ) LENGTH: 5 amino acids
    ( B ) TYPE: Amino acid
    ( D ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION: SEQ ID NO:23:

Ser Xaa Pro Gln Lys
                  5

( 2 ) INFORMATION FOR SEQ ID NO:24:

( i ) SEQUENCE CHARACTERISTICS:
          ( A ) LENGTH: 15 amino acids
          ( B ) TYPE: Amino acid
          ( D ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION: SEQ ID NO:24:

Phe Tyr Arg Asn Leu Asn Gln Arg Phe Ala Asp Ala Ile Val Lys
                  5                   10                  15

( 2 ) INFORMATION FOR SEQ ID NO:25:

( i ) SEQUENCE CHARACTERISTICS:
          ( A ) LENGTH: 11 amino acids
          ( B ) TYPE: Amino acid
          ( D ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION: SEQ ID NO:25:

Asp Gly Ser Val Met Gln Xaa Xaa Gln Leu Xaa
                  5                   10

( 2 ) INFORMATION FOR SEQ ID NO:26:

( i ) SEQUENCE CHARACTERISTICS:
          ( A ) LENGTH: 18 amino acids
          ( B ) TYPE: Amino acid
          ( D ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION: SEQ ID NO:26:

Asn Ala Ile Asn Thr Ala Val Leu Glu Asn Ile Ile Pro Xaa Xaa
                  5                   10                  15

Xaa Val Lys ( 2 ) INFORMATION FOR SEQ ID NO:27:

( i ) SEQUENCE CHARACTERISTICS:
          ( A ) LENGTH: 12 amino acids
          ( B ) TYPE: Amino acid
          ( D ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION: SEQ ID NO:27:

Leu Val Asn Asp Glu Ala Ser Glu Gly Gln Val Lys
                 5                       10

( 2 ) INFORMATION FOR SEQ ID NO:28:

( i ) SEQUENCE CHARACTERISTICS:
        ( A ) LENGTH: 11 amino acids
        ( B ) TYPE: Amino acid
        ( D ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION: SEQ ID NO:28:

Xaa Gln Asp Ile Leu Leu Asn Asn Thr Phe Xaa
                 5                       10

( 2 ) INFORMATION FOR SEQ ID NO:29:

( i ) SEQUENCE CHARACTERISTICS:
        ( A ) LENGTH: 14 amino acids
        ( B ) TYPE: Amino acid
        ( D ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION: SEQ ID NO:29:

Asp Thr Thr Gln Thr Ala Pro Val Xaa Asn Asn Val Xaa Pro
                 5                       10

( 2 ) INFORMATION FOR SEQ ID NO:30:

( i ) SEQUENCE CHARACTERISTICS:
        ( A ) LENGTH: 11 amino acids
        ( B ) TYPE: Amino acid
        ( D ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION: SEQ ID NO:30:

Asn Gln Leu Asp Ala Xaa Asn Tyr Ala Glu Val
                 5                       10

( 2 ) INFORMATION FOR SEQ ID NO:31:

( i ) SEQUENCE CHARACTERISTICS:
        ( A ) LENGTH: 10 amino acids
        ( B ) TYPE: Amino acid
        ( D ) TOPOLOGY: Linear ( i i ) MOLECULE TYPE: Peptide ( i i i ) HYPOTHETICAL: Yes ( i v ) FRAGMENT TYPE: N-terminal ( v ) SEQUENCE DESCRIPTION: SEQ ID NO:31:

Asn Leu Ser Arg Trp Arg Asn Tyr Ala Glu
                 5                   10

( 2 ) INFORMATION FOR SEQ ID NO:32:

( i ) SEQUENCE CHARACTERISTICS:
        ( A ) LENGTH: 4 amino acids
        ( B ) TYPE: Amino acid
        ( D ) TOPOLOGY: Linear ( i i ) MOLECULE TYPE: Peptide ( i i i ) HYPOTHETICAL: 32

( i v ) FRAGMENT TYPE: N-terminal ( v ) SEQUENCE DESCRIPTION: SEQ ID NO:32:

Trp Gln Gly Lys ( 2 ) INFORMATION FOR SEQ ID NO:33:

( i ) SEQUENCE CHARACTERISTICS:
        ( A ) LENGTH: 11 amino acids
        ( B ) TYPE: Amino acid
        ( D ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION: SEQ ID NO:33:

Ile Gln Leu Gly Glu Ser Asn Asp Asp Xaa Xaa
                5                          10

( 2 ) INFORMATION FOR SEQ ID NO:34:

( i ) SEQUENCE CHARACTERISTICS:
        ( A ) LENGTH: 11 amino acids
        ( B ) TYPE: Amino acid
        ( D ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION: SEQ ID NO:34:

Gln Val Pro Thr Ile Gln Asp Xaa Thr Asn Lys
                5                          10

( 2 ) INFORMATION FOR SEQ ID NO:35:

( i ) SEQUENCE CHARACTERISTICS:
        ( A ) LENGTH: 6 amino acids
        ( B ) TYPE: Amino acid
        ( D ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION: SEQ ID NO:35:

Ile Tyr Xaa Tyr Val Lys
               5

( 2 ) INFORMATION FOR SEQ ID NO:36:

( i ) SEQUENCE CHARACTERISTICS:
        ( A ) LENGTH: 6 amino acids
        ( B ) TYPE: Amino acid (D) TOPOLOGY: Linear (ii) MOLECULE TYPE: Peptide (iii) HYPOTHETICAL: Yes (iv) FRAGMENT TYPE: N-terminal (v) SEQUENCE DESCRIPTION: SEQ ID NO:36:

Asn Gln Leu Thr Asn Tyr
                      5

(2) INFORMATION FOR SEQ ID NO:37:

(i) SEQUENCE CHARACTERISTICS:
        (A) LENGTH: 4 amino acids
        (B) TYPE: Amino acid
        (C) TOPOLOGY: Linear (ii) MOLECULE TYPE: Peptide (iii) HYPOTHETICAL: Yes (iv) FRAGMENT TYPE: N-terminal (v) SEQUENCE DESCRIPTION:37:

Val Ala Leu Gly (2) INFORMATION FOR SEQ ID NO:38:

(i) SEQUENCE CHARACTERISTICS:
        (A) LENGTH: 12 amino acids
        (B) TYPE: Amino acid
        (C) TOPOLOGY: Linear (ii) MOLECULE TYPE: Peptide (iii) HYPOTHETICAL: No (iv) FRAGMENT TYPE: N-terminal (v) SEQUENCE DESCRIPTION:38:

Asp Ala Ile Val Val Asn Pro Xaa Asp Ser Val Ala
                      5                      10

(2) INFORMATION FOR SEQ ID NO:39:

(i) SEQUENCE CHARACTERISTICS:
        (A) LENGTH: 9 amino acids
        (B) TYPE: Amino acid
        (C) TOPOLOGY: Linear (ii) MOLECULE TYPE: Peptide (iii) HYPOTHETICAL: No (iv) FRAGMENT TYPE: N-terminal (v) SEQUENCE DESCRIPTION:39:

Thr Phe Thr Asn Tyr Asp Gly Ser Lys
                      5

(2) INFORMATION FOR SEQ ID NO:40:

(i) SEQUENCE CHARACTERISTICS:
        (A) LENGTH: 10 amino acids
        (B) TYPE: Amino acid
        (C) TOPOLOGY: Linear (ii) MOLECULE TYPE: Peptide (iii) HYPOTHETICAL: No (iv) FRAGMENT TYPE: N-terminal (v) SEQUENCE DESCRIPTION:40:

```
Thr Gly Asn Asp Pro Ser His Ile Ala Lys
                  5                      10
```

( 2 ) INFORMATION FOR SEQ ID NO:41:

( i ) SEQUENCE CHARACTERISTICS:
        ( A ) LENGTH: 7 amino acids
        ( B ) TYPE: Amino acid
        ( C ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION:41:

```
Ile Tyr Glu Ser Gln Gly Lys
                5
```

( 2 ) INFORMATION FOR SEQ ID NO:42:

( i ) SEQUENCE CHARACTERISTICS:
        ( A ) LENGTH: 12 amino acids
        ( B ) TYPE: Amino acid
        ( C ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION:42:

```
Ala Glu Gly Ala Thr Gly Gly Leu Val Pro His Lys
                5                       10
```

( 2 ) INFORMATION FOR SEQ ID NO:43:

( i ) SEQUENCE CHARACTERISTICS:
        ( A ) LENGTH: 10 amino acids
        ( B ) TYPE: Amino acid
        ( C ) TOPOLOGY: Linear ( i i ) MOLECULE TYPE: Peptide ( i i i ) HYPOTHETICAL: No ( i v ) FRAGMENT TYPE: N-terminal ( v ) SEQUENCE DESCRIPTION:43:

```
Leu Ala Thr Glu Leu Pro Ala Xaa Ser Lys
                  5                    10
```